US009250172B2

(12) United States Patent
Harris et al.

(10) Patent No.: US 9,250,172 B2
(45) Date of Patent: Feb. 2, 2016

(54) SYSTEMS AND METHODS FOR PREDICTING METABOLIC AND BARIATRIC SURGERY OUTCOMES

(71) Applicants: Jason L. Harris, Lebanon, OH (US); Christopher J. Hess, Blue Ash, OH (US); Nitin Kumar Jain, Mason, OH (US); Diane M. Francis, Brooklyn, NY (US); Thomas E. Albrecht, Campbell, CA (US); Tina Denise Hunter, Cincinnati, OH (US)

(72) Inventors: Jason L. Harris, Lebanon, OH (US); Christopher J. Hess, Blue Ash, OH (US); Nitin Kumar Jain, Mason, OH (US); Diane M. Francis, Brooklyn, NY (US); Thomas E. Albrecht, Campbell, CA (US); Tina Denise Hunter, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 14/429,706

(22) PCT Filed: Sep. 20, 2013

(86) PCT No.: PCT/US2013/060825
§ 371 (c)(1),
(2) Date: Mar. 19, 2015

(87) PCT Pub. No.: WO2014/047388
PCT Pub. Date: Mar. 27, 2014

(65) Prior Publication Data
US 2015/0248613 A1  Sep. 3, 2015

Related U.S. Application Data

(60) Provisional application No. 61/704,077, filed on Sep. 21, 2012.

(51) Int. Cl.
*G06F 19/00* (2011.01)
*G01N 5/04* (2006.01)

(52) U.S. Cl.
CPC .............. *G01N 5/04* (2013.01); *G06F 19/3443* (2013.01); *G06F 19/3481* (2013.01); *G06F 19/3475* (2013.01)

(58) Field of Classification Search
CPC ....................................................... G06N 5/04
See application file for complete search history.

(56) References Cited

U.S. PATENT DOCUMENTS 7,194,301 B2    3/2007   Jenkins et al.
7,901,885 B2    3/2011   Salonen et al.
(Continued)

FOREIGN PATENT DOCUMENTS

EP         2192196 A1      6/2010
WO      WO-0050639 A2      8/2000
(Continued)

OTHER PUBLICATIONS

Bold Overview. Surgical Review Corporation. Retrieved from <http://www.surgicalreview.org/bold/overview>, 1 page, Date unknown, but believed to be no later than Feb. 1, 2012.
(Continued)

*Primary Examiner* — Alan Chen
(74) *Attorney, Agent, or Firm* — Mintz Levin Cohn Ferris Glovsky and Popeo, P.C.

(57) ABSTRACT

Various systems and methods for predicting metabolic and bariatric surgery outcomes are provided. The systems and methods can also provide predictions for non-surgical metabolic and bariatric treatments. In general, a user can receive predictive outcomes of multiple bariatric procedures that could be performed on a patient. In one embodiment, a user can electronically access a metabolic and bariatric surgery outcome prediction system, e.g., using one or more web pages. The system can provide predictive outcomes of one or more different bariatric surgeries for the patient based on data gathered from the user and on historical data regarding outcomes of the different bariatric surgeries. The system can additionally provide predictive outcomes for not having any treatment and/or a comparison of the predictive outcomes of the one or more different bariatric surgeries to the predictive outcomes for not having any treatment.

21 Claims, 32 Drawing Sheets

(56) References Cited

U.S. PATENT DOCUMENTS

| | | | |
|---|---|---|---|
| 8,036,912 | B2 | 10/2011 | Jensen et al. |
| 8,156,166 | B2 | 4/2012 | LeClair et al. |
| 2005/0220710 | A1 | 10/2005 | Seeley |
| 2006/0040293 | A1 | 2/2006 | Salonen et al. |
| 2006/0062859 | A1 | 3/2006 | Blum et al. |
| 2006/0252050 | A1 | 11/2006 | Ordovas et al. |
| 2007/0054278 | A1 | 3/2007 | Cargill |
| 2007/0059722 | A1 | 3/2007 | Salonen et al. |
| 2007/0072798 | A1 | 3/2007 | Salonen et al. |
| 2009/0018031 | A1 | 1/2009 | Trinklein et al. |
| 2009/0024144 | A1 | 1/2009 | Zeiner et al. |
| 2010/0098809 | A1 | 4/2010 | Bender et al. |
| 2010/0105038 | A1 | 4/2010 | Draper et al. |
| 2010/0112570 | A1 | 5/2010 | Aziz et al. |
| 2010/0113580 | A1 | 5/2010 | Aronne |
| 2010/0136561 | A1 | 6/2010 | Draper et al. |
| 2010/0209350 | A1 | 8/2010 | Pfuetzner et al. |
| 2010/0210541 | A1 | 8/2010 | Pfuetzner |
| 2011/0008906 | A1 | 1/2011 | Aziz et al. |
| 2011/0111404 | A1 | 5/2011 | Salonen et al. |
| 2011/0111405 | A1 | 5/2011 | Salonen et al. |
| 2011/0123981 | A1 | 5/2011 | Dina et al. |
| 2011/0263490 | A1 | 10/2011 | Kaplan et al. |
| 2011/0270360 | A1 | 11/2011 | Harris et al. |
| 2011/0282683 | A1 | 11/2011 | Jensen et al. |
| 2012/0040342 | A1 | 2/2012 | Gerhard et al. |
| 2014/0087999 | A1 | 3/2014 | Kaplan et al. |

FOREIGN PATENT DOCUMENTS

| | | |
|---|---|---|
| WO | WO-2009117415 A2 | 9/2009 |
| WO | WO-2010024852 A1 | 3/2010 |
| WO | WO-2011058232 A1 | 5/2011 |
| WO | WO-2011090765 A1 | 7/2011 |
| WO | WO-2011144818 A1 | 11/2011 |
| WO | WO-2012092049 A2 | 7/2012 |
| WO | WO-2012092056 A1 | 7/2012 |
| WO | WO-2012092057 A1 | 7/2012 |
| WO | WO-2013115756 A2 | 8/2013 |

OTHER PUBLICATIONS

Find out if you're a candidate for bariatric surgery. Surgeon/Seminar Finder. Realize. Ethicon Endo-Surgery. 2012, 4 pages. Retrieved from <http://www.realize.com/bariatric-surgery-eligibility>.

Find out if you're a candidate for bariatric (with results. Surgeon/Seminar Finder. Realize. Ethicon Endo-Surgery. 2012, 6 pages. Retrieved from <http://www.realize.com/bariatric-surgery-eligibility>.

Find weight loss surgeons and information seminars. Surgeon/Seminar Finder. Realize. Ethicon Endo-Surgery. 2012, 2 pages. Retrieved from <http://www.realize.com/find-surgeons-seminars>.

Frequently Asked Questions. Surgeon/Seminar Finder. Realize. Ethicon Endo-Surgery. 2012, 10 pages. Retrieved from<http://realize.com/faqs.html>.

Patient Guide. Realize. Ethicon Endo-Surgery. 2010, 56 pages.

Seminar Results. Surgeon/Seminar Finder. Realize. Ethicon Endo-Surgery. 2012, 3 pages. Retrieved from <http://realize.com/seminar-finder-results?zipcode=&state=OH&f>.

Obesity treatment guide: A reference for assessing and treating overweight and obese patients Bariatric times. Physician handout. 2011, 2 pages. Last accessed Sep. 19, 2012 from <http://bariatrictimes.com/about>.

Insight for better healthcare. Overview of Marketscan database. Thomson Reuters. 2010, 2 pages. Retrieved from <http://web.archive.org/web/20110309003451/http:/marketscan.thomsonreuters.com/marketscanportal/>.

Aslan, I.R. et al., "Weight loss after Roux-en-Y gastric bypass in obese patients heterozygous for MC4R mutations," Obesity Surgery, vol. 21.7 (2011):930-934.

Averbukh, Y. et al., "Depression score predicts weight loss following Roux-en-Y gastric bypass," Obesity Surgery, vol. 13.6 (2003):833-836.

Baltasar, A. et al., "Weight loss reporting," Obesity Surgery, vol. 18.6 (2008):761-762.

Branson, Ruth et al., "Binge eating as a major phenotype of melanocortin 4 receptor gene mutations," The New England Journal of Medicine, vol. 348.12 (2003):1096-1103.

Bray, G.A., "Medications for weight reduction," Endocrinology and metabolism clinics of North America, vol. 37.4 (2008):923-942.

Bray, G.A. et al., "Is it time to change the way we report and discuss weight loss?" Obesity (Silver Spring), vol. 17.4 (2009):619-621.

Bray, M.S., "Implications of gene-behavior interactions: prevention and intervention for obesity," Obesity (Silver Spring), vol. 16.Suppl. 3 (2008):S72-S78.

Buchwald, H. et al., "Bariatric surgery: a systemic review and meta-analysis," JAMA, vol. 292.14 (2004):1724-1737.

Busetto, L. et al., "Outcome predictors in morbidly obese recipients of an adjustable gastric band," Obesity Surgery, vol. 12.1 (2002):83-92.

Cawley, John et al., "The medical care costs of obesity: an instrumental variables approach," The Journal of Health Economics, vol. 31.1 (2012):219-230.

Chambers, A.P. et al., "Weight-independent changes in blood glucose homeostasis after gastric bypass or vertical sleeve gastrectomy in rats," Gastroenterology, vol. 141.3 (2011):950-958.

Chen, H.H. et al., "Ala55Val polymorphism on UCP2 gene predicts greater weight loss in morbidly obese patients undergoing gastric banding," Obesity Surgery, vol. 17.7 (2007):926-933.

Chobanian, Aram et al., "The Seventh Report on the Joint National Committee on Prevention, Detection, Evaluation, and Treatment of High Blood Pressure: the JNC 7 report," JAMA, vol. 289.19 (2003):2560-2572.

Chu, X. et al., "Association of morbid obesity with FTO and INSIG2 allelic variants," Arch. Surg., vol. 143.3 (2008):235-240.

Corella, D. et al., "Obese subjects carrying the 11482G>A polymorphism at the perilipin locus are resistant to weight loss after dietary energy restrictions," J. Clin. Endocrinol. Metab., vol. 90.9 (2005):5121-5126.

Cushman, W.C. et al., "Success and predictors of blood pressure control in diverse North American settings: the antihypertensive and lipid-lowering treatment to prevent heart attack trial (ALLHAT)," J. Clin. Hypertens. (Greenwich), vol. 4.6 (2002):393-404.

De Luis, D.A. et al., "Influence of ALA54THR polymorphism of fatty acid binding protein 2 on lifestyle modification response in obese subjects," Ann. Nutr. Metab., vol. 50.4 (2006):354-360.

De Luis, D.A. et al., "Influence of -55CT polymorphism of UCP3 gene on surgical results of biliopancreatic diversion," Obesity Surgery, vol. 20.7 (2010):895-899.

De Luis, D.A. et al., "Influence of Ala54Thr polymorphism of fatty acid-binding protein-2 on clinical results of biliopancreatic diversion," Nutrition, vol. 24.4 (2008):300-304.

De Luis, D.A. et al., "Influence of Ala54Thr polymorphism of fatty acid-binding protein 2 on weight loss and insulin levels secondary to two hypocaloric diets: a randomized clinical trial," Diabetes Res. Clin. Pract., vol. 82.1 (2008):113-118.

De Luis, D.A. et al., "Effects of C358A missense polymorphism of the endocannabinoid degrading enzyme fatty acid amide hydrolase on weight loss and cardiovascular risk factors 1 year after bilopancreatic diversion surgery," Surg. Obes. Relat. Dis., vol. 6.5 (2010):516-520.

De Luis, D.A. et al., "G1359A polmorphism of the cannabinoid receptor gene (CNR1) and clinical results of biliopancreatic diversion," Eur. Rev. Med. Pharmacol. Sci., vol. 14.3 (2010):197-201.

De Luis, D.A. et al., "Influence of G308A polymorphism of tumor necrosis factor alpha gene on surgical results of biliopancreatic diversion," Obesity Surgery, vol. 20.2 (2010):221-225.

De Luis, D.A. et al., "Influence of lys656asn polymorphism of leptin receptor gene on surgical results of biliopancreatic diversion," J. Gastrointest. Surg., vol. 14.5 (2010):899-903.

Deitel, Mervyn et al., "Recommendations for reporting weight loss," Obesity Surgery, vol. 13.2 (2003):159-160.

Deitel, Mervyn et al., "Reporting weight loss 2007," Obesity Surgery, vol. 17.5 (2007):565-568.

(56) References Cited

OTHER PUBLICATIONS

Deram, S. et al., "Effects of perilipin (PLIN) gene variation on metabolic syndrome risk and weight loss in obese children and adolescents," J. Clin. Endocrinol. Metab., vol. 93.12 (2008):4933-4940.
Deram, S. et al., "Genetic variants influencing effectiveness of weight loss strategies," Arq. Bras. Endocrinol. Metabl., vol. 53.3 (2009):129-138.
Di Renzo et al., "Body composition changes after laparoscopic adjustable gastric banding: what is the role of -174G>C interleukin-6 promoter gene polymorphism in the therapeutic strategy?" Int. J. Obes. (Lond). vol. 36.3 (2012):369-378.
Dixon, J.B. et al., "Pre-operative predictors of weight loss at 1-year after Lap-Band surgery," Obesity Surgery, vol. 11.2 (2001):200-207.
Dixon, J.B. et al., "Minimal reporting requirements for weight loss: current methods not ideal," Obesity Surgery, vol. 15.7 (2005):1034-1039.
Drazen, D.L. et al., "Peripheral signals in the control of satiety and hunger," Curr. Opin. Clin. Nutr. Metab. Care, vol. 6.6 (2003):621-629.
Gardner, Christopher D. et al., "Comparison of the Atkins, Zone, Ornish, and LEARN diets for change in weight and related risk factors among overweight premenopausal women: the A to Z Weight Loss Study: a randomized trial," JAMA, vol. 297.9 (2007):969-977.
Garaulet, M. et al., "Clock gene is implicated in weight reduction in obese patients participating in a dietary programme based on the Mediterranean diet," Int. J. Obes. (Lond), vol. 34.3 (2010):516-523.
Geloneze, S.R. et al., "PGC1alpha gene Gly482Ser polymorphism predicts improved metabolic, inflammatory and vascular outcomes following bariatric surgery," International Journal of Obesity, vol. 36 (2012):363-368.
GenBank Accession No. NM_028320, 6 pages Jun. 29, 2012.
Gerhard, Glenn S. et al., "The influence of iron status and genetic polymorphisms in the HFE gene on the risk for postoperative complications after bariatric surgery: a prospective cohort study in 1,064 patients," Patient Safety in Surgery, vol. 5.1 (2011), 9 pages.
Gomez-Ambrosi, Javier et al., "Gene expression profile of omental adipose tissue in human obesity," The FASEB Journal, doi: 10.1096/fj.03-0591fje, 25 pages (2003).
Goyenechea et al., "The—11391 G/A polymorphism of the adiponectin gene promoter is associated with metabolic syndrome traits and the outcome of an energy-restricted diet in obese subjects," Horm. Metab. Res., vol. 41.1 (2009):55-61.
Greenawait, D.M. et al., "A survey of the genetics of stomach, liver, and adipose gene expression from a morbidly obese cohort," Genome Res., vol. 21.7 (2011):1008-1016.
Hainer, V. et al., "Role of hereditary factors in weight loss and its maintenance," Physiological Research, vol. 57.Suppl. 1 (2008):S1-S15.
Hatoum, I.J. et al., "Capacity for physical activity predicts weight loss after Roux-en-Y gastric bypass," Obesity (Silver Spring), vol. 17.1 (2009):92-99.
Hatoum, I.J. et al., "Heritability of the weight loss response to gastric bypass surgery," J. Clin. Endocrinol. Metabl., vol. 96.10 (2011):E1630-E1633.
Hatoum, I.J. et al., "Melanocortin-4 receptor signaling is required for weight loss after gastric bypass surgery," J. Clin. Endocrinol. Metabl., vol. 97.6, (2012):E1023-E1031.
Hatoum, Ida J. et al., "Weight Loss after Gastric Bypass is Associated With a Variant at 15q26.1," The American Journal of Human Genetics, vol. 92 (2013):827-834.
Haupt, A. et al., "Impact of variation in the FTO gene on whole body fat distribution, ectopic fat, and weight loss," Obesity (Silver Spring), vol. 16.8 (2008):1969-1972.
Haupt, A. et al., "Impact of variation near MC4R on whole-body fat distribution, liver fat, and weight loss," Obesity (Silver Spring), vol. 17.10 (2009):1942-1945.
Hirsch, Andy, "Considering weight loss surgery? There's an app for that," Bucknell University, retrieved at http://www.bucknell.edu/x78968.xml, Sep. 10, 2012, 2 pages.

Kaplan, L.M. et al., "Pharmacologic therapies for obesity," Gastroenterology Clinics of North America, vol. 34.1 (2005):91-104.
Karamanakos, S.N. et al., "Weight loss, appetite suppression, and changes in fasting and postprandial ghrelin and peptide-YY levels after Roux-en-Y gastric bypass and sleeve gastrectomy: a prospective, double blind study," Ann. Surg., vol. 247.3 (2008):401-407.
Karmali, Shahzeer et al., "Is it time to abandon excess weigh loss in reporting surgical weight loss?" Surgery for Obesity and Related Diseases, vol. 5.4 (2009):503-506.
Kral, John G. et al., "Melanocortin-4 receptor gene variants affect results of gastric banding," Digestive Disease Week 2004, 45th Annual Meeting, Gastroenterology, vol. 126.Suppl. 2 (2004):A-768.
Lappalainen, T.J. et al., "The common variant in the FTO gene did not modify the effect of lifestyle changes on body weight: the Finnish Diabetes Prevention Study," Obesity (Silver Spring), vol. 17.4 (2009:832-836.
Lee, W.J. et al., "Bariatric surgery: Asia-Pacific perspective," Obesity Surgery, vol. 15.6 (2005):751-757.
Lee, Y.C. et al., "Prediction of successful weight reduction after laparoscopic adjustable gastric banding," Hepatogastroenterology, vol. 56.93 (2009):1222-1226.
Li, Y. et al., "MaCH: using sequence and genotype data to estimate haplotypes and unobserved genotypes," Genet. Epidemiol., vol. 34.8 (2010):816-834.
Libra et al., "Molecular determinants in the transport of a bile acid-derived diagnostic agent in tumoral and nontumoral cell lines of human liver," J. Pharmacol. Exp. Ther., vol. 319.2 (2006):809-817.
Liou, T.H. et al., "ESR1, FTO, and UCP2 genes interact with bariatric surgery affecting weight loss and glycemic control in severely obese patients," Obesity Surgery, vol. 21.11 (2011):1758-1765.
Lindi, V.I. et al., "Association of the Pro12Ala polymorphism in the PPAR-gamma2 gene with 3-year incidence of type 2 diabetes and body weight change in the Finnish Diabetes Prevention Study," Diabetes, vol. 51.8 (2002):2581-2586.
Lutfi, R. et al., "Predictors of success after laparoscopic gastric bypass: a multivariate analysis of socioeconomic factors," Surg. Endosc., vol. 20.6 (2006):864-867.
Luyckx, F.H. et al., "Influence of the A-->G (-3826) uncoupling gene (UCP1)variant on the dynamics of body weight before and after gastroplasty in morbidly obese subjects," International Journal of Obesity and Related Metabolic Disorders, vol. 22.12 (1998):1244-1245.
Ma, Y. et al., "Predictors of weight status following laparoscopic gastric bypass," Obesity Surgery, vol. 16.9 (2006):1227-1231.
Masuo, K. et al., "Rebond weight gain as associated with high plasma norepinephrine levels that are mediated through polymorphisms in the beta2-adrenoceptor," Am. J. Hypertens., vol. 18.11 (2005):1508-1516.
Matsuo, T. et al., "PPARG genotype accounts for part of individual variation in body weight reduction in response to calorie restriction," Obesity (Silver Spring), vol. 17.10 (2009):1924-1931.
McAuley, Erica Z. et al., "Identification of sialyltransferase 8B as a generalized susceptibility gene for psychotic and mood disorders on chromosomes," PLoS One, vol. 7.5 (2012):e38172, 10 pages.
McMinn, J.E. et al., "Neuroendocrine mechanisms regulating food intake and body weight," Obes. Rev., vol. 1.1 (2000):37-46.
Mirshahi, U.L. et al., "The MC4R(I251L) allele is associated with better metabolic status and more weight loss after gastric bypass surgery," J. Clin. Endocrinol. Metab., vol. 93.12 (2011):E2088-E2096.
Montasser, M.E. et al., "Gene by smoking interaction in hypertension: identification of a major quantitative trait locus on chromosome 15q for systolic blood pressure in Mexican-Americans," J. Hypertens., vol. 27.3 (2009):491-501.
Moreno-Aliaga, M.J. et al., "Does weight loss prognosis depend on genetic make-up?" Obes. Rev., vol. 6.2 (2005):155-168.
Moschen, A.R. et al., "Effects of weight loss induced by bariatric surgery on hepatic adipocytokine expression," J. Hepatol., vol. 51.4 (2009):765-777.
Muller, Timo D. et al., "'Fat mass and obesity associated' gene (FTO): no significant association of variant rs9939609 with weight loss in a lifestyle intervention and lipid metabolism markers in Ger-

(56) References Cited

OTHER PUBLICATIONS man obese children and adolescents," BMC Medical Genetics, vol. 9.85 (2008), doi:10.1186/1471-2350-9-85, 6 pages.
Nicklas et al., "Genetic variation in the peroxisome proliferator-activated receptor-gamma2gene (Pro12Ala) affects metabolic responses to weight loss and subsequent weight regain," Diabetes, vol. 50.9 (2001):2172-2176.
Ochner, C.N. et al., "Selective reduction in neural responses to high calorie foods following gastric bypass surgery," Ann. Surg., vol. 253.3 (2011):502-507.
Ogden, Cynthia L. et al., "Prevalence of overweight and obesity in the United States," JAMA, vol. 295.13 (2006):1549-1555.
Peterli, R. et al., "Melancortin-4 receptor gene and complications after gastric banding," Obes. Surg., vol. 16.2 (2006):189-195.
Peterli, R. et al., "Improvement in glucose metabolism after bariatric surgery: comparison of laparoscopic Roux-en-Y gastric bypass and laparoscopic sleeve gastrectomy: a prospective randomized trial," Ann. Surg., vol. 250.2 (2009):234-241.
Potoczna, Natascha et al., "G protein polymorphisms do not predict weight loss and improvement of hypertension in severely obese patients," Journal of Gastrointestinal Surgery, vol. 8.7 (2004):862-868.
Potoczna, Natascha et al., "Gene variants and binge eating as predictors of comorbidity and outcome of treatment in severe obesity," Journal of Gastrointestinal Surgery, vol. 8.8 (2004):971-982.
Price, Alkes L. et al., "Principal components analysis corrects for stratification in genome-wide association studies," Nature Genetics, vol. 38(2006):904-909.
Purcell, S. et al., "PLINK: a tool set for whole-genome association and population-based linkage analyses," Am. J. Hum. Genet., vol. 81.3 (2007):559-575.
Rankinen, Tuomo et al., "FTO genotype is associated with exercise training-induced changes in body composition," Obesity (Silver Spring), vol. 18.2 (2010):322-326.
Rankinen, Tuomo et al., "The Human Obesity Gene Map: The 2005 Update," Obesity, vol. 14.4 (2006):529-644.
Reinehr, T. et al., "Aggravating effect of INSIG2 and FTO on overweight reduction in one-year lifestyle intervention," Arch. Dis. Child, vol. 94 (2009):965-967.
Ryden et al., "Weight Loss After Vertical Banded Gastroplasty can be Predicted: A Prospective Psychological Study," Obesity Surgery, vol. 6.3 (1996):237-243.
Sakane, N. et al., "Effects of Trp64Arg mutation in the beta 3-adrenergic receptor gene on weight loss, body fat distribution, glycemic control, and insulin resistance in obese type 2 diabetic patients," Diabetes Care, vol. 20.12 (1997):1887-1890.
Santos, J.L. et al., "Allelic variants of melanocortin 3 receptor gene (MC3R) and weight loss in obesity: a randomised trial of hypo-energetic high- versus low-fat diets," PLoS One, vol. 6.3 (2011):e19934, 8 pages.
Sarahan, Kari A. et al., "Four out of eight genes in a mouse chromosome 7 congenic donor region are candidate obesity genes," Physiological Genomics, vol. 43.18 (2011):1049-1055.
Sarzynski et al., "Associations of markers in 11 obesity candidate genes with maximal weight loss and weight regain in the SOs bariatric surgery cases," International Journal of Obesity, vol. 35.5 (2011):676-683.
Schauer, Philip R. et al., "Bariatric surgery versus intensive medical therapy in obese patients with diabetes," The New England Journal of Medicine, vol. 366.17 (2012):1567-1576.
Sesti, Giorgio et al., "Impact of common polymorphisms in candidate genes for insulin resistance and obesity on weight loss of morbidly obese subjects after laparoscopic adjustable gastric banding and hypocaloric diet," J. Clin. Endocrinol. Metab., vol. 90.9 (2005):5064-2069.
Sharma, Arya M. et al., "Reporting weight loss: is simple better?" Obesity (Silver Spring), vol. 18.2 (2010):219.
Shin, A.C. et al., "Roux-en-Y gastric bypass surgery changes food reward in rats," Int. J. Obes. (Lond), vol. 35.5 (2011):642-651.
Sjostrom, Lars et al., "Effects of bariatric surgery on mortality in Swedish obese subjects," The New England Journal of Medicine, vol. 357 (2007):741-752.
Sorensen, Thorkild I.A. et al., "Genetic polymorphisms and weight loss in obesity: a randomised trial of hypo-energetic high- versus low-fat diets," PLoS Clin. Trials, vol. 1.2 (2006):e12, 14 pages.
Spalova, J. et al., "Neuromedin beta: P73T polymorphism in overweight and obese subjects," Physiol. Res., vol. 57.Suppl. 1 (2008):S39-S48.
Speliotes, Elizabeth K. et al., "Association analyses of 249,796 individuals reveal 18 new loci associated with body mass index," Nat. Genet., vol. 42.11 (2010):937-948.
Still, C.D. et al., "High allelic burden of four obesity SNPs is associated with poorer weight loss outcomes following gastric bypass surgery," Obesity (Silver Spring), vol. 19.8 (2011):1676-1683.
Stylopoulos, N. et al., "Roux-en-Y gastric bypass enhances energy expenditure and extends lifespan in diet-induced obese rats," Obesity (Silver Spring), vol. 17.10 (2009):1839-1847.
Suchanek, P. et al., "Actigenetic of ACE gene polymorphism in Czech obese sedentary females," Physiological Research, vol. 58.Suppl. 1 (2009):S47-S52.
Wang, K.S. et al., "ANAPC1 and SLCO3A1 are associated with nicotine dependence: meta-analysis of genome-wide association studies," Drug Alcohol Depend., vol. 124.3 (2012):325-332.
Wing et al., "Long-term effects of a lifestyle intervention on weight and cardiovascular risk factors in individuals with type 2 diabetes mellitus: four-year results of the Look AHEAD trial," Arch Intern. Med., vol. 170.17 (2010):1566-1575.
Yixin, S. et al., "The impact of obesity on oxygen desaturatino in patients with sleep apnea/hypopnea syndrome," Nihon Kokyuki Gakkai Zasshi, vol. 39.9 (2001):650-655.
International Search Report and Written Opinion for Application No. PCT/US2013/60825, 17 pages, dated Dec. 13, 2013.
International Search Report for Application No. PCT/US13/60901, 6 pages, dated Jan. 30, 2014.
[No Author Listed] Surgeon/Seminar Finder Results. Surgeon/Seminar Finder. Realize. Ethicon Endo-Surgery. 2012, 4 pages. Retrieved from <http://realize.com/surgeons-seminars-results?zipcode=&state=OH&f>.

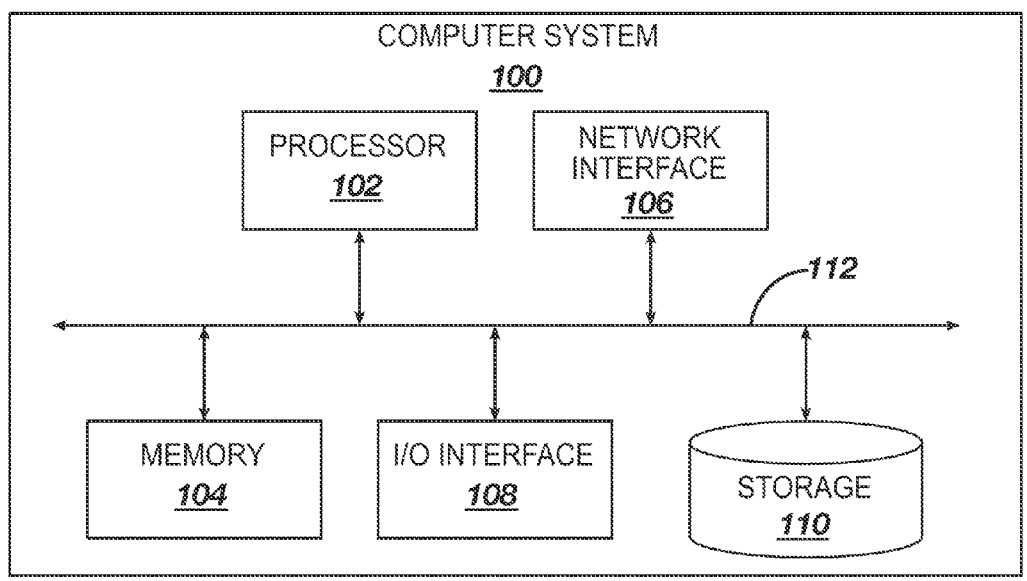
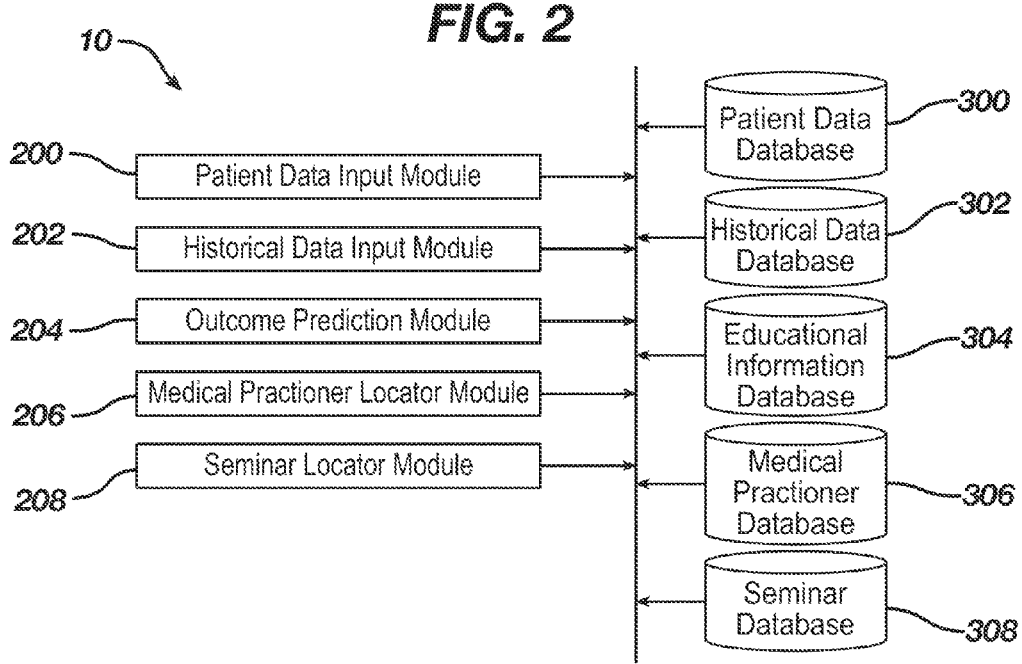

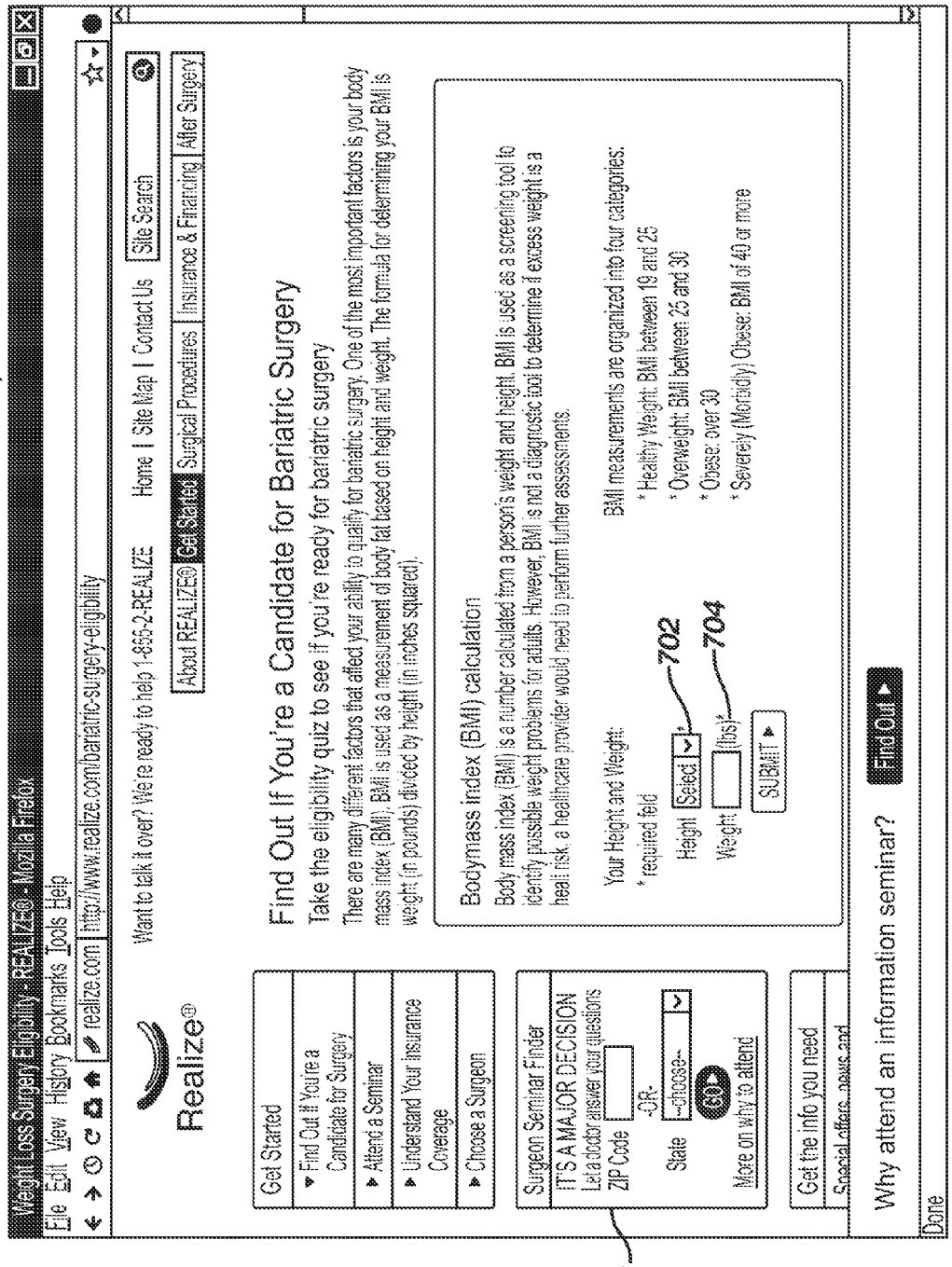

FIG. 8

Explore the Impact of Weight Loss Surgery on Patients Like You

An educational application that enables you to learn more about the potential outcomes of bariatric surgery based on the experience of more than 30,000 patients in the U.S.

Personal Information
* Required Information

- Age: ___ yrs    BMI --
- Gender: ○ Female  ○ Male
- Height: ___ ft ___ in ___ cm
- Weight: ___ lbs ___ kg
- Race: [▼]
- Ethnicity: [▼]

[GO]

Current Conditions

| | | |
|---|---|---|
| Asthma/COPD ▲ | ○ Yes | ⊙ No |
| Depression ▲ | ○ Yes | ⊙ No |
| Diabetes (Type 2) ▲ | ○ Yes | ⊙ No |
| GERD/Hiatal Hernia ▲ | ○ Yes | ⊙ No |
| Hyperlipidemia ▲ | ○ Yes | ⊙ No |
| Hypertension ▲ | ○ Yes | ⊙ No |
| Knee/Hip/Back Surgery ▲ | ○ Yes | ⊙ No |
| Liver Disease ▲ | ○ Yes | ⊙ No |
| Obst. Sleep Apnea ▲ | ○ Yes | ⊙ No |
| Other Breathing Difficulties ▲ | ○ Yes | ⊙ No |

Current Medications

| | |
|---|---|
| Depression: ▲ | [None ▼] |
| Diabetes (Type 2) ▲ | [None ▼] |
| Hyperlipidemia ▲ | [No Meds ▼] |
| Hypertension | |
| Diuretics ▲ | ○ Yes ⊙ No |
| Alpha Blockers ▲ | ○ Yes ⊙ No |
| Beta Blockers ▲ | ○ Yes ⊙ No |
| C-Channel Blockers ▲ | ○ Yes ⊙ No |

FIG. 9

Explore the Impact of Weight Loss Surgery on Patients Like You

An educational application that enables you to learn more about the potential outcomes of bariatric surgery based on the experience of more than 30,000 patients in the U.S.

Personal Information
* Required Information

* Age: [45] yrs    BMI 41
* Gender: ● Female  ○ Male
* Height: [5] ft [2] in  [157] cm
* Weight: [225] lbs  [102] kg
* Race: [White ▼]
* Ethnicity: [Other ▼]

[GO]

Current Conditions

| | | |
|---|---|---|
| Asthma/COPD | ○ Yes | ● No |
| Depression | ○ Yes | ● No |
| Diabetes (Type 2) | ● Yes | ○ No |
| GERD Hiatal Hernia | ○ Yes | ● No |
| Hyperlipidemia | ● Yes | ○ No |
| Hypertension | ○ Yes | ● No |
| Knee/Hip/Back Surgery | ○ Yes | ● No |
| Liver Disease | ○ Yes | ● No |
| Obst. Sleep Apnea | ○ Yes | ● No |
| Other Breathing Difficulties | ○ Yes | ● No |

Current Medications

| | | |
|---|---|---|
| Depression | [None ▼] | |
| Diabetes (Type 2) | [Non-Insulin Only ▼] | |
| Hyperlipidemia | [No Meds ▼] | |
| Hypertension | | |
| Diuretics | ● Yes | ○ No |
| Alpha Blockers | ○ Yes | ● No |
| Beta Blockers | ○ Yes | ● No |
| C-Channel Blockers | ○ Yes | ● No |

New Patient | Logout

Home | Logout

Explore the Impact of Weight Loss Surgery on Patients Like You
An educational application that enables you to learn more about the potential outcomes of bariatric surgery based on the experience of more than 30,000 patients in the U.S.

Personal Information
* Required Information

* Age  [35] yrs   BMI 49
* Gender  ○ Female  ● Male
* Height  [5] ft [6] in  [167] cm
* Weight  [305] lbs  [138] kg
* Race  [White ▼]
* Ethnicity  [Hispanic/Latino ▼]

[ GO ]

Current Conditions

| Condition | Yes | No |
|---|---|---|
| Asthma/COPD | ○ Yes | ● No |
| Depression | ○ Yes | ● No |
| Diabetes (Type 2) | ○ Yes | ● No |
| GERD Hiatal Hernia | ○ Yes | ● No |
| Hyperlipidemia | ● Yes | ○ No |
| Hypertension | ○ Yes | ● No |
| Knee/Hip/Back Surgery | ○ Yes | ● No |
| Liver Disease | ○ Yes | ● No |
| Obst. Sleep Apnea | ● Yes | ○ No |
| Other Breathing Difficulties | ○ Yes | ● No |

Current Medications

Depression [None ▼]
Diabetes (Type 2) [None ▼]
Hyperlipidemia [One or More Meds ▼]
Hypertension

| Med | Yes | No |
|---|---|---|
| Diuretics | ○ Yes | ● No |
| Alpha Blockers | ○ Yes | ● No |
| Beta Blockers | ○ Yes | ● No |
| C-Channel Blockers | ○ Yes | ● No |

Scout - Mozilla Firefox
File Edit View History Bookmarks Tools Help
http://www.webaddress.com Bypass Risks  Gastric Sleeve Risks The following is general information about potential risk and complications and is not based on the patient sample used to show potential weight loss or comorbidity change post weight loss surgery.

Complications
- Gastric perforation
- Reservoir leakage or twisting
- Lack of satiety
- Reflux
- Nausea and vomiting
- Outlet obstruction
- Pouch dilation
- Band slippage

- Iron deficiency
- Chronic anemia
- Heightened bone calcium loss
- Anastomotic leak
- Fistula
- Metabolic bone disease
- Vitamin B12 deficiency
- Dumping syndrome
- Intestinal irritation and ulcers
- Difficulty visualizing under X-ray or endoscopy  1.48%
  0.14%

- Tissue separation
- Gastric leakage
- Ulcers
- Fistula
- Dyspepsia
- Esophageal dysmotility 1.42%
  0.18%

Reported Rates
Mortality*    0.91%
        0.03%

* Mortality means death within 30 days of procedure
** Estimated based on data collected from published literature

Disclaimer:
The information contained on this site is to help you learn more about the benefits of bariatric surgery. It is provided for educational purposes only and represents no statement, promise or guarantee by Ethicon Endo-Surgery concerning the your eligibility, experience or potential outcomes. Ask your doctor if bariatric surgery is right for you and for guidance on expected outcomes, benefits and risks.

The weight loss, medication and diagnosis information on this site is derived from statistical analysis of historical claims and clinical databases as well as research published in peer reviewed journals. While predictive modeling techniques were used, the results cannot predict the specific outcomes of any individual and may vary.

This site published by Ethicon Endo-Surgery, Inc., which is solely responsible for its contents, and is intended for U.S. participants in the Scout pilot. This site is not intended as a substitute for professional medical care. Only your physician can diagnose and appropriately treat your symptoms.

Home | Logout

2500

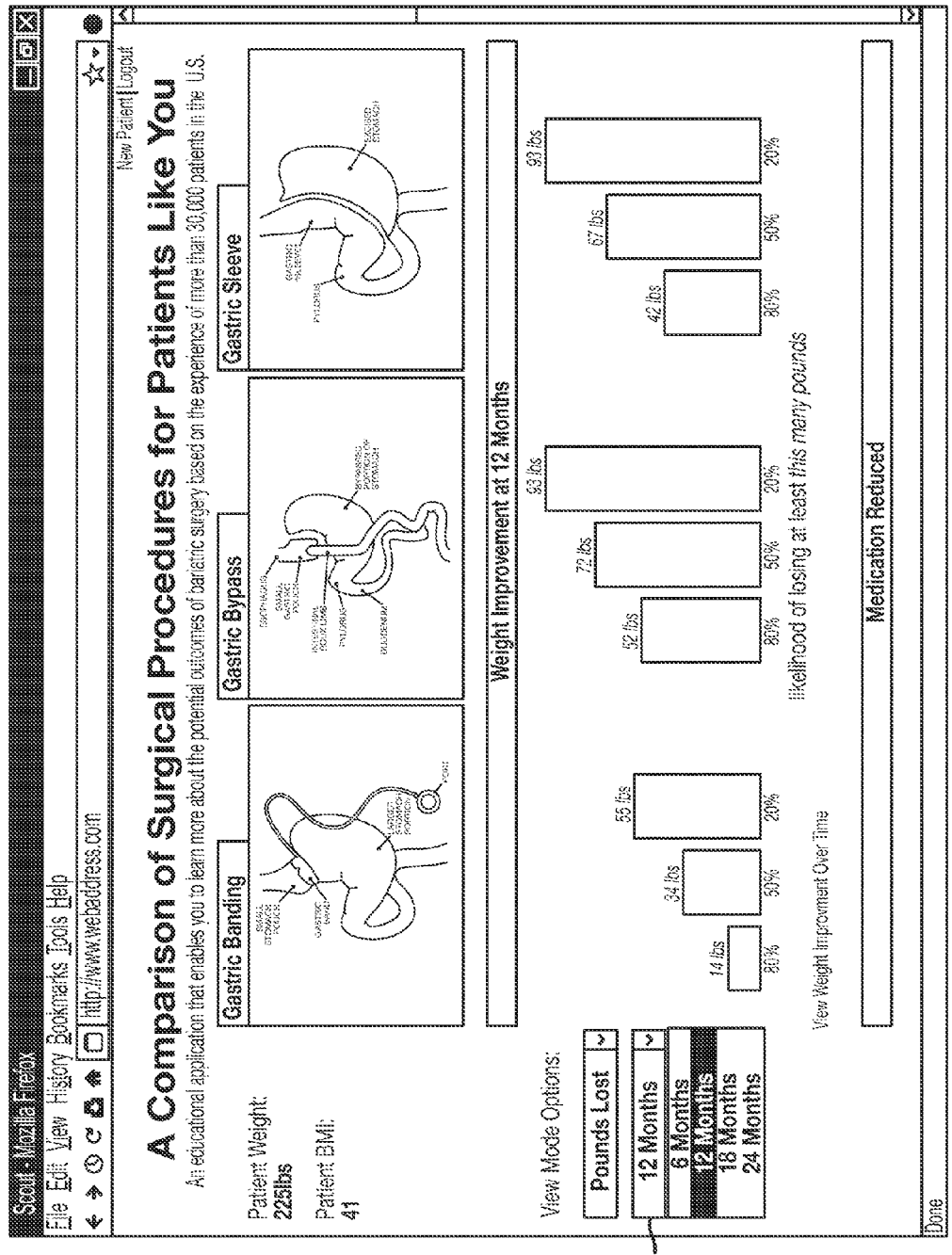

FIG. 34

*Scout - Mozilla Firefox*
File  Edit  View  History  Bookmarks  Tools  Help
http://www.webaddress.com

3200

Bypass Risks   Gastric Sleeve Risks

The following is general information about potential risk and complications and is not based on the patient sample used to show potential weight loss or comorbidity change post weight loss surgery.

Complications

- Gastric perforation
- Reservoir leakage or twisting
- Lack of satiety
- Reflux
- Nausea and vomiting
- Outlet obstruction
- Pouch dilation
- Band slippage

- Iron deficiency
- Chronic anemia
- Heightened bone calcium loss
- Anastomotic leak
- Fistula
- Metabolic bone disease
- Vitamin B12 deficiency
- Dumping syndrome
- Intestinal irritation and ulcers
- Difficulty visualizing under X-ray or endoscopy   1.48%   1.42%
                                                    0.14%   0.18%

- Tissue separation
- Gastric leakage
- Ulcers
- Fistula
- Dyspepsia
- Esophageal dysmotility

Reported Rates
Mortality*    0.91%
                  0.03%

* Mortality means death within 30 days of procedure
** Estimated based on data collected from published literature

Disclaimer:
The information contained on this site is to help you learn more about the benefits of bariatric surgery. It is provided for educational purposes only and represents no statement, promise or guarantee by Ethicon Endo-Surgery concerning the your eligibility, experience or potential outcomes. Ask your doctor if bariatric surgery is right for you and for guidance on expected outcomes, benefits and risks.

The weight loss, medication and diagnosis information on this site is derived from statistical analysis of historical claims and clinical databases as well as research published in peer reviewed journals. While predictive modeling techniques were used, the results cannot predict the specific outcomes of any individual and may vary.

This site published by Ethicon Endo-Surgery, Inc., which is solely responsible for its contents, and is intended for U.S. participants in the Scout pilot. This site is not intended as a substitutes for professional medical care. Only your physician can diagnose and appropriately treat your symptoms.

Home | Logout

©2012 Ethicon Endo-Surgery, Inc. All rights reserved. EES confidential. For authorized user only.
Do not distribute or share without written permission
Done

FIG. 37

SYSTEMS AND METHODS FOR PREDICTING METABOLIC AND BARIATRIC SURGERY OUTCOMES

CROSS REFERENCE TO RELATED APPLICATIONS

The present application claims priority to International Application No. PCT/US2013/060825 entitled "Systems And Methods For Predicting Metabolic And Bariatric Surgery Outcomes" filed Sep. 20, 2013, which claims priority to U.S. Provisional Patent Application No. 61/704,077 entitled "Systems And Methods For Predicting Metabolic And Bariatric Surgery Outcomes" filed Sep. 21, 2012, which are hereby incorporated by reference in their entireties.

FIELD

The present disclosure relates generally to systems and methods for predicting metabolic and bariatric surgery outcomes.

BACKGROUND

It is estimated that 34% of adults in the United States are overweight and an additional 32% have obesity. The myriad metabolic, inflammatory, degenerative, cognitive, and neoplastic sequealae of obesity together cost more than $168 billion annually and account for nearly 10% of all healthcare expenditures in the United States.

Behavioral and pharmacotherapeutic treatments for severe obesity have been met with limited long-term success. In contrast, metabolic and bariatric surgeries such as Roux-en-Y gastric bypass (RYGB) leads to significant and sustained weight loss. Because of its excellent clinical outcomes, RYGB is currently the most commonly used surgical therapy for obesity. Metabolic and bariatric surgical procedures have increasingly been performed laparoscopically. Reduced post-operative recovery time, markedly decreased post operative pain and wound infection, and improved cosmetic outcome are well established benefits of laparoscopic surgery, derived mainly from the ability of laparoscopic surgeons to perform an operation utilizing smaller incisions of the body cavity wall.

Despite the various metabolic and bariatric surgical procedures each providing chances for weight loss and associated improvements in comorbid conditions, there is wide variability in outcomes (e.g., weight loss, diabetes improvements, etc.) among individual patients who receive such surgeries. Several clinical, demographic, psychological, and surgical predictors of weight loss have been reported, but these factors explain only a small fraction of the variation in weight loss after surgery. The identification of novel predictors of outcomes after metabolic and bariatric surgical procedures can both provide insight into the biological mechanisms of action of this procedure, as well as provide predictive markers that may be used to substratify those patients who may respond best to surgery or alternative treatments. Additionally, because numerous factors can affect a patient's outcomes following bariatric surgery, and because some factors may be more relevant for some patients more than others depending on an individual's overall health, it can be difficult for medical professionals to consider and balance the factors to arrive at an accurate prediction as to how the surgery will affect a particular patient. It can be even more difficult, and likely impossible, for non-medical professionals, e.g., patients, to consider and balance such factors.

Accordingly, there remains a need for improved systems and methods for predicting metabolic and bariatric surgery outcomes.

SUMMARY

The present invention generally provides systems and methods for predicting bariatric surgery outcomes. In one aspect, a system is provided that in one embodiment includes a patient data input module and an outcome prediction module. The patient data input module can be configured to receive data regarding a patient from a client terminal via a network. The data can include two or more of a height of the patient, a weight of the patient, a gender of the patient, an age of the patient, a medical history of the patient, a medical status of the patient, a body mass index (BMI) of the patient, an ethnicity of the patient, a medical prescription history of the patient, a medical prescription status of the patient, types of medical treatments for obesity previously received by the patient, types of medical treatments for health issues other than obesity previously received by the patient, insurance information for the patient, diet information for the patient, psychological history of the patient, and a genetic indicator of the patient. The outcome prediction module can be configured to predict an outcome of each of a plurality of different types of bariatric surgery for the patient based at least on the received data regarding the patient and on historical data regarding outcomes of a plurality of bariatric surgery procedures performed on a plurality of patients. The outcomes of the plurality of bariatric surgery procedures performed on the plurality of patients can include at least one of an amount of BMI reduction and an amount of weight loss. The predicted outcome of each of the plurality of bariatric surgery procedures can include at least one of a predicted amount of BMI reduction and a predicted amount of weight loss.

The different types of bariatric surgery can include sleeve gastrectomy, gastric banding, and gastric bypass.

The predicted amount of BMI reduction can be presented as a range of possible BMI reduction, and the predicted amount of weight loss can be presented as a range of possible amount of weight loss.

When the outcomes of the plurality of bariatric surgery procedures performed on the plurality of patients includes at least the amount of BMI reduction, the predicted amount of BMI reduction can be presented as a range of possible BMI reduction. When the outcomes of the plurality of bariatric surgery procedures performed on the plurality of patients includes at least the amount of weight loss, the predicted amount of weight loss can be presented as a range of possible amount of weight loss.

The system can include a medical practitioner locator module configured to provide a recommended medical practitioner for the patient from among a plurality of medical practitioners stored in a medical practitioner database based at least on a geographic location of the patient. The plurality of medical practitioners can each be marked in the medical practitioner database as having experience with at least one of the plurality of different types of bariatric surgery. The medical practitioner locator module can be configured to provide the recommended medical practitioner for the patient based at least on a selection of one of the different types of bariatric surgery received from the client terminal.

The system can include a seminar locator module configured to provide a recommended seminar for the patient from among a plurality of seminars stored in a seminar database based at least on a geographic location of the patient. The plurality of seminars can each be marked in the seminar database as being related to at least one of the plurality of different types of bariatric surgery. The seminar locator module can be configured to provide the recommended seminar for the patient based at least on a selection of one of the different types of bariatric surgery received from the client terminal.

The outcome prediction module can have any number of variations. For example, the outcome prediction module can be configured to communicate the predicted outcome of each of the plurality of bariatric surgery procedures to the client terminal via the network. For another example, the outcome prediction module can be configured to compare the received data regarding the patient with corresponding data regarding the plurality of patients, determine, based on the comparison, a subset of the plurality of patients with which the patient most closely correlates, and determine the predicted outcomes of each of the plurality of bariatric surgery procedures using the outcomes for the subset of the plurality of patients. For yet another example, the outcome prediction module can be configured, after the patient has had performed thereon one the plurality of different types of bariatric surgeries, to predict an outcome of the one of the plurality of different types of bariatric surgery for a second patient based at least on an actual outcome of the one of the plurality of different types of bariatric surgery performed on the patient. For still another example, the outcome prediction module can be configured to predict the outcome using at least one of univariate analysis, multivariable regression analysis, advanced regression analysis, fully saturated regression analysis, stepwise regression analysis, and least angle regression analysis. For another example, the outcome prediction module can be configured to cause the client terminal to graphically display the predicted outcome of each of the plurality of bariatric surgery procedures. The outcome prediction module can be configured to cause the client terminal to graphically display the predicted outcome of each of the plurality of bariatric surgery procedures on a same web page such that a user viewing the client terminal can view all the predicted outcomes at once, thereby facilitating user comparison of the predicted outcomes. For yet another example, the outcome prediction module can be configured to provide educational information from an educational information database storing a plurality of educational materials related to the different types of bariatric surgery. For another example, the outcome prediction module can include one or more web pages. For still another example, the outcome prediction module can be configured to predict an outcome of one or more non-surgical treatments for the patient based at least on the received data regarding the patient and on historical data regarding outcomes of a plurality of non-surgical treatments received by a plurality of patients. The outcomes of the plurality of non-surgical treatments received by the plurality of patients can include at least one of an amount of BMI reduction and an amount of weight loss, and the predicted outcome of each of the one or more non-surgical treatments can include at least one of a predicted amount of BMI reduction and a predicted amount of weight loss. The outcome prediction module can be configured to communicate the predicted outcome of each of the plurality of bariatric surgery procedures and the predicted outcome of each of the one or more non-surgical treatments to the client terminal via the network. For yet another example, the outcome prediction module can be configured to predict an outcome of the patient receiving no obesity treatment based at least on the received data regarding the patient and on historical data regarding outcomes of a plurality of patients who did not receive obesity treatment. The outcomes of the plurality of patients who did not receive obesity treatment received by the plurality of patients can include at least one of an amount of BMI change, a change in weight, and a change in one or more comorbidities. The predicted outcome of non-treatment for the patient can include at least one of an amount of BMI change, a change in weight, and a change in the one or more comorbidities. The outcome prediction module can be configured to communicate the predicted outcome of each of the plurality of bariatric surgery procedures and the predicted outcome of each the non-treatment for the patient to the client terminal via the network.

The patient data input module can have any number of variations. For example, the patient data input module can include one or more web pages.

In another embodiment, a system is provided that in one embodiment includes a computer system configured to communicate with a client terminal via a network. The computer system can include a processor configured to predict an outcome of each of a plurality of different types of bariatric surgery for a patient. Each of the outcomes can be based at least on patient data and on historical data regarding outcomes of a plurality of bariatric surgery procedures performed on a plurality of patients. The patient data can include at least two or more of a height of the patient, a weight of the patient, a gender of the patient, an age of the patient, a medical history of the patient, a medical status of the patient, a BMI of the patient, an ethnicity of the patient, a medical prescription history of the patient, a medical prescription status of the patient, types of medical treatments for obesity previously received by the patient, types of medical treatments for health issues other than obesity previously received by the patient, insurance information for the patient, diet information for the patient, psychological history of the patient, and a genetic indicator of the patient. The outcomes of the plurality of bariatric surgery procedures performed on the plurality of patients can include at least one of an amount of BMI reduction and an amount of weight loss. The predicted outcome of each of the plurality of bariatric surgery procedures can include at least one of a predicted amount of BMI reduction and a predicted amount of weight loss. The processor can be configured to communicate each of the predicted outcomes to the client terminal via the network.

The processor can be configured to receive the patient data from the client terminal via the network.

The processor can be configured to retrieve the historical data from a historical data database. The processor can be configured to add an actual outcome of one the plurality of different types of bariatric surgeries performed on the patient to the historical data database such that the processor is configured to predict an outcome of the one of the plurality of different types of bariatric surgery for a second patient actual based at least on the historical data including the actual outcome. The processor can be configured to predict the outcome for the second patient based at least on data regarding the second patient received from a second client terminal via the network.

The processor can be configured, after the patient has had performed thereon one the plurality of different types of bariatric surgeries, to predict an outcome of the one of the plurality of different types of bariatric surgery for a second patient based at least on an actual outcome of the one of the plurality of different types of bariatric surgery performed on the patient.

The processor can be configured to predict the outcome using at least one of univariate analysis, multivariable regression analysis, advanced regression analysis, fully saturated regression analysis, stepwise regression analysis, and least angle regression analysis.

The processor can be configured to cause the client terminal to graphically display the predicted outcome of each of the plurality of bariatric surgery procedures. The processor can be configured to cause the client terminal to graphically display the predicted outcome of each of the plurality of bariatric surgery procedures on a same web page such that a user viewing the client terminal can view all the predicted outcomes at once, thereby facilitating user comparison of the predicted outcomes.

The computer system can be configured to predict an outcome of one or more non-surgical treatments for the patient based at least on the received data regarding the patient and on historical data regarding outcomes of a plurality of non-surgical treatments received by a plurality of patients. The outcomes of the plurality of non-surgical treatments received by the plurality of patients can include at least one of an amount of BMI reduction and an amount of weight loss. The predicted outcome of each of the one or more non-surgical treatments can include at least one of a predicted amount of BMI reduction and a predicted amount of weight loss. The computer system can be configured to communicate the predicted outcome of each of the plurality of bariatric surgery procedures and the predicted outcome of each of the one or more non-surgical treatments to the client terminal via the network.

The computer system can be configured to predict an outcome of the patient receiving no obesity treatment based at least on the received data regarding the patient and on historical data regarding outcomes of a plurality of patients who did not receive obesity treatment. The outcomes of the plurality of patients who did not receive obesity treatment received by the plurality of patients can include at least one of an amount of BMI change, a change in weight, and a change in one or more comorbidities. The predicted outcome of non-treatment for the patient can include at least one of an amount of BMI change, a change in weight, and a change in the one or more comorbidities. The computer system can be configured to communicate the predicted outcome of each of the plurality of bariatric surgery procedures and the predicted outcome of each the non-treatment for the patient to the client terminal via the network.

In another example, a system is provided that in one embodiment includes a patient data input module and an outcome prediction module. The patient data input module can be configured to receive data regarding a patient from a client terminal via a network. The data can include two or more of a height of the patient, a weight of the patient, a gender of the patient, an age of the patient, a medical history of the patient, a medical status of the patient, a BMI of the patient, an ethnicity of the patient, a medical prescription history of the patient, a medical prescription status of the patient, types of medical treatments for obesity previously received by the patient, types of medical treatments for health issues other than obesity previously received by the patient, insurance information for the patient, diet information for the patient, psychological history of the patient, and a genetic indicator of the patient. The outcome prediction module can be configured to predict an outcome of each of a plurality of different types of bariatric surgery for the patient based at least on the received data regarding the patient and on historical data regarding outcomes of a plurality of bariatric surgery procedures performed on a plurality of patients. The outcomes of the plurality of bariatric surgery procedures performed on the plurality of patients can include a change in at least one comorbidity. The predicted outcome of each of the plurality of bariatric surgery procedures can include change in the at least one comorbidity.

The different types of bariatric surgery can include sleeve gastrectomy, gastric banding, and gastric bypass.

The predicted amount of BMI reduction can be presented as a range of possible change in the at least one comorbidity.

The system can include a medical practitioner locator module configured to provide a recommended medical practitioner for the patient from among a plurality of medical practitioners stored in a medical practitioner database based at least on a geographic location of the patient. The plurality of medical practitioners can each be marked in the medical practitioner database as having experience with at least one of the plurality of different types of bariatric surgery. The medical practitioner locator module can be configured to provide the recommended medical practitioner for the patient based at least on a selection of one of the different types of bariatric surgery received from the client terminal.

The system can include a seminar locator module configured to provide a recommended seminar for the patient from among a plurality of seminars stored in a seminar database based at least on a geographic location of the patient. The plurality of seminars can each be marked in the seminar database as being related to at least one of the plurality of different types of bariatric surgery. The seminar locator module can be configured to provide the recommended seminar for the patient based at least on a selection of one of the different types of bariatric surgery received from the client terminal.

The outcome prediction module can have any number of variations. For example, the outcome prediction module can be configured to communicate the predicted outcome of each of the plurality of bariatric surgery procedures to the client terminal via the network. For another example, the outcome prediction module can be configured to compare the received data regarding the patient with corresponding data regarding the plurality of patients, determine, based on the comparison, a subset of the plurality of patients with which the patient most closely correlates, and determine the predicted outcomes of each of the plurality of bariatric surgery procedures using the outcomes for the subset of the plurality of patients. For yet another example, the outcome prediction module can be configured, after the patient has had performed thereon one the plurality of different types of bariatric surgeries, to predict an outcome of the one of the plurality of different types of bariatric surgery for a second patient based at least on an actual outcome of the one of the plurality of different types of bariatric surgery performed on the patient. For still another example, the outcome prediction module can be configured to predict the outcome using at least one of univariate analysis, multivariable regression analysis, advanced regression analysis, fully saturated regression analysis, stepwise regression analysis, and least angle regression analysis. For another example, the outcome prediction module can be configured to cause the client terminal to graphically display the predicted outcome of each of the plurality of bariatric surgery procedures. The outcome prediction module can be configured to cause the client terminal to graphically display the predicted outcome of each of the plurality of bariatric surgery procedures on a same web page such that a user viewing the client terminal can view all the predicted outcomes at once, thereby facilitating user comparison of the predicted outcomes. For still another example, the outcome prediction module can be configured to provide educational information from an educational information database storing a plurality of educational materials related to the different types of bariatric surgery. For yet another example, the outcome prediction module can include one or more web pages. For another example, the outcome prediction module can be configured to predict an outcome of one or more non-surgical treatments for the patient based at least on the received data regarding the patient and on historical data regarding outcomes of a plurality of non-surgical treatments received by a plurality of patients. The outcomes of the plurality of non-surgical treatments received by the plurality of patients can include a change in at least one comorbidity. The predicted outcome of each of the one or more non-surgical treatments can include a change in the at least one comorbidity. The outcome prediction module can be configured to communicate the predicted outcome of each of the plurality of bariatric surgery procedures and the predicted outcome of each of the one or more non-surgical treatments to the client terminal via the network. For yet another example, the outcome prediction module can be configured to predict an outcome of the patient receiving no obesity treatment based at least on the received data regarding the patient and on historical data regarding outcomes of a plurality of patients who did not receive obesity treatment. The outcomes of the plurality of patients who did not receive obesity treatment received by the plurality of patients can include at least one of an amount of BMI change, a change in weight, and a change in one or more comorbidities. The predicted outcome of non-treatment for the patient can include at least one of an amount of BMI change, a change in weight, and a change in the one or more comorbidities. The outcome prediction module can be configured to communicate the predicted outcome of each of the plurality of bariatric surgery procedures and the predicted outcome of each the non-treatment for the patient to the client terminal via the network.

The patient data input module can have any number of variations. For example, the patient data input module can include one or more web pages.

In another embodiment, a system is provided that in one embodiment includes a computer system configured to communicate with a client terminal via a network. The computer system can include a processor configured to predict an outcome of each of a plurality of different types of bariatric surgery for a patient. Each of the outcomes can be based at least on patient data and on historical data regarding outcomes of a plurality of bariatric surgery procedures performed on a plurality of patients. The patient data can include at least two or more of a height of the patient, a weight of the patient, a gender of the patient, an age of the patient, a medical history of the patient, a medical status of the patient, a BMI of the patient, an ethnicity of the patient, a medical prescription history of the patient, a medical prescription status of the patient, types of medical treatments for obesity previously received by the patient, types of medical treatments for health issues other than obesity previously received by the patient, insurance information for the patient, diet information for the patient, psychological history of the patient, and a genetic indicator of the patient. The outcomes of the plurality of bariatric surgery procedures performed on the plurality of patients can include a change in at least one comorbidity. The predicted outcome of each of the plurality of bariatric surgery procedures can include a change in at least one comorbidity. The processor can be configured to communicate each of the predicted outcomes to the client terminal via the network.

In another aspect, a computer-readable medium is provided that can have stored thereon a program that when executed can cause a computer to perform a method. The method can include the functions performed by a patient data input module and an outcome prediction module. The computer-readable medium can be a non-transitory medium.

In another aspect, a surgical method is provided that can include the functions performed by a patient data input module and an outcome prediction module.

BRIEF DESCRIPTION OF DRAWINGS

This invention will be more fully understood from the following detailed description taken in conjunction with the accompanying drawings, in which:

FIG. 1 is a schematic diagram of an embodiment of a computer system;

FIG. 2 is a schematic diagram of a metabolic and bariatric surgery outcome predictive system;

FIG. 7 is a schematic diagram of an embodiment of a patient data, medical practitioner, and seminar web interface of the metabolic and bariatric surgery outcome predictive system of FIG. 2;

FIG. 8 is a schematic diagram of another embodiment of a patient data web interface of the bariatric surgery outcome predictive system of FIG. 2;

FIG. 9 is a schematic diagram of the patient data web interface of FIG. 8 having patient data input thereto for a first patient;

FIG. 10 is a schematic diagram of the patient data web interface of FIG. 8 having patient data input thereto for a second patient;

FIG. 27 is a continuation of the schematic diagram of FIG. 26;

FIG. 28 is a schematic diagram of the patient data and predicted outcome web interface of FIG. 25 with post-surgery time field options being displayed;

FIG. 34 is a continuation of the schematic diagram of FIG. 33;

FIG. 37 is a continuation of the schematic diagram of FIG. 36;

DETAILED DESCRIPTION

Figure 3:
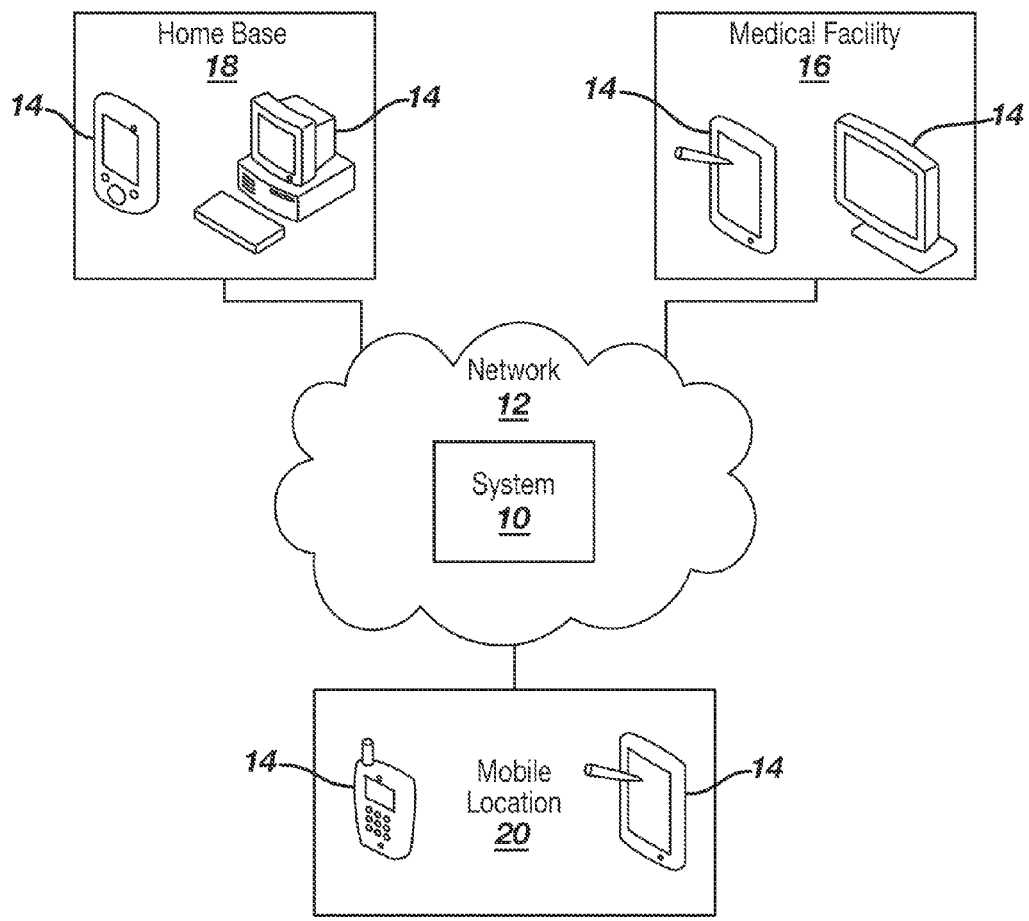
FIG. 3 is a schematic diagram of an embodiment of a network system including the bariatric surgery outcome predictive system of FIG. 2.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Overview of Predicting Metabolic and Bariatric Surgery Outcomes

Various systems and methods are provided for predicting metabolic and bariatric surgery outcomes. The systems and methods can also provide predictions for non-surgical metabolic and bariatric treatments. In general, a user, e.g., a patient, a medical professional involved with treating a patient, a medical student, a hospital administrator, a health insurance administrator, etc., can receive predictive outcomes of multiple bariatric procedures that could be performed on a patient. The collection of therapies for the treatment of obesity and metabolic disease (e.g., diet and exercise, pharmaceutical therapy, medically supervised therapy, metabolic surgery (open, laparoscopic, natural orifice, etc.), bariatric surgery (open, laparoscopic, natural orifice, etc.), etc.) are collectively defined herein as bariatric surgery. In one embodiment, a user can electronically access a metabolic and bariatric surgery outcome prediction system, e.g., using one or more web pages. The system can provide predictive outcomes of one or more different bariatric surgeries for the patient based on data gathered from the user and on historical data regarding outcomes of the different bariatric surgeries. The system can additionally provide predictive outcomes for not having any treatment and/or a comparison of the predictive outcomes of the one or more different bariatric surgeries to the predictive outcomes for not having any treatment. Generally, the predictive outcomes provided by the system can include a potential clinical metabolic outcome of each of the different bariatric surgeries, e.g., a predicted amount of weight loss, a predicted amount of body mass index (BMI) reduction, an improvement in a health condition associated with a metabolic disease, an associated risk of complications from the treatment, and/or an associated cost of the surgery and post-operative care. The predictive outcomes can be based on a plurality of patient-specific characteristics, e.g., age, weight, height, BMI, ethnicity, medical prescription history and/or status, genetic data (e.g., a genetic indicator), types of previously received medical treatments for obesity (e.g., gastric banding, gastric bypass, sleeve gastrectomy, etc), medical history and/or status, gender, etc. The predictive outcomes can also be based on historic results of the different types of bariatric surgeries on other patients. The predictive outcomes can thus be based at least in part on data specific to the patient and not just on historical data, e.g., data gathered by the user from previous personal experience, friends or colleagues, journal articles, Internet research, clinical data, etc. The outputs can thus be personalized to the patient. The system can help the user be more informed about which of the bariatric surgeries would be most effective if performed on the patient, help specifically compare and contrast the different bariatric surgeries, and help the user decide which of the different bariatric surgeries, if any, to pursue for the patient. The system can therefore help maximize effectiveness of treatment for the patient by allowing a most effective option to be identified and pursued by the patient and/or by medical practitioner(s) treating the patient. The system can also help inform the user about bariatric surgery options that they might not have been aware of at all, e.g., new procedures, and/or deepen understanding of bariatric surgery procedures previously known to the user. The system can be configured to allow the user to save the predictive outcomes, which can then be accessed at a later date/time by the user and/or one or more other users, e.g., the user's surgeon, the user's endocrinologist, the user's primary care physician, etc., to which the user grants access to the saved data.

In addition to providing predictive outcomes, the system can optionally provide educational information regarding each of the different bariatric surgeries and/or other types of information related to bariatric surgery such as estimated patient monetary cost (based on one or more factors such as the patient's insurance carrier, similar procedures performed in the patient's geographic location, etc.), estimated insurance reimbursement (based on one or more factors such as the patient's insurance carrier, similar procedures performed in the patient's geographic location, etc.), estimated length of post-surgery hospital stay (based on one or more factors such as similar procedures performed in the patient's geographic location, the patient's age, the patient's other health conditions or disorders, etc.) The system can therefore help the user be more fully informed about the various risks and benefits of the various bariatric surgeries before deciding which of the bariatric surgeries to pursue, if any. Applying similar modeling techniques, personalized predictions can be provided for one or more of the preceding educational and/or other information.

Obesity and Weight-Related Disorders

As used herein, the term "obesity" or "obese" refers to an individual having a BMI of 25 kg/m$^2$ or more. BMI is a measure expressing the relationship (or ratio) of weight-to-height based on a mathematical formula in which a person's body weight in kilograms is divided by the square of his or her height in meters (i.e., wt/(ht)$^2$).

Weight loss can be characterized using a number of different metrics, including an absolute number of pounds or BMI points lost, weight or BMI achieved after weight loss, a percent of baseline weight or BMI lost (% weight change (WC)), and percent excess body weight lost (% EBWL).

The term "weight-related disorder" as used herein refers to disorders, diseases, and conditions that are caused or characterized by abnormal energy use or consumption leading to excessive weight gain or loss, altered responses to ingested or endogenous nutrients, energy sources, hormones or other signaling molecules within the body or altered metabolism of carbohydrates, lipids, proteins, nucleic acids or a combination thereof. A weight-related disorder can be associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain) or the like. Non-limiting examples of weight-related disorders (comorbidities) include obesity, diabetes, including type II diabetes, insulin-deficiency, insulin-resistance, insulin-resistance related disorders, glucose intolerance, syndrome X, inflammatory and immune disorders, dyslipidemia, metabolic syndrome, non-alcoholic fatty liver, abnormal lipid metabolism, obstructive sleep apnea, asthma, cancer, depression, infertility, polycystic ovarian syndrome, neurodegenerative disorders, hypertension, high cholesterol, anxiety, congestive heart failure, ischemic heart disease, GERD, atherogenic dyslipidemia, hyperlipidemic conditions such as atherosclerosis, hypercholesterolemia, and other coronary artery diseases in mammals, and other disorders of metabolism.

Disorders also included are conditions that occur or cluster together, and increase the risk for heart disease, stroke, diabetes, and obesity. Having just one of these conditions such as increased blood pressure, elevated insulin levels, excess body fat around the waist or abnormal cholesterol levels can increase the risk of the above mentioned diseases. In combination, the risk for coronary heart disease, stroke, insulin-resistance syndrome, and diabetes is even greater.

The increasing prevalence of obesity in the population has led to a parallel rise in surgical procedures, like bariatric surgery, as a treatment for obesity and related comorbid conditions. Surgical procedures can achieve a sustained weight reduction of up to 50% of excess body weight in the majority of patients, and are more effective than nonsurgical approaches.

Bariatric Surgery and Alternative Treatments

Surgical procedures to treat severe obesity have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Such surgical procedures have increasingly been performed laparoscopically. Reduced postoperative recovery time, markedly decreased post operative pain and wound infection, and improved cosmetic outcome are well established benefits of laparoscopic surgery, derived mainly from the ability of laparoscopic surgeons to perform an operation utilizing smaller incisions of the body cavity wall.

As used herein, "bariatric surgery" generally refers to a variety of procedures performed in a subject to achieve weight loss. Bariatric surgery refers to a surgical procedure to alter gastrointestinal structure or function so as to affect body weight, body composition, or energy balance regulation or otherwise alter metabolic function. Some non-limiting examples can be any form of gastric bypass, Roux-en-Y gastric bypass (RYGB), biliopancreatic diversion, vertical sleeve gastrectomy, adjustable gastric banding, vertical banded gastroplasty, intragastric balloon therapy, gastric plication and other forms of gastric volume reduction (see also US Pat. Pub. No. 2009/0024144 entitled "Hybrid Endoscopic/Laparoscopic Device For Forming Serosa To Serosa Plications In A Gastric Cavity" filed Jul. 18, 2007, which is hereby incorporated by reference in its entirety), Magenstrasse and Mill, small bowel transposition, biliary diversion, procedures involving an anastomotic connection of the gastrointestinal tract (e.g., jejunoileostomy, etc.), duodenal endoluminal barrier and variations of the procedures above as well as other methods known by those skilled in the art.

Some non-surgical examples of alternative treatments to bariatric surgery can include hormone and neuropeptide therapy, receptor agonists, activation of brown adipose tissue and the use of duodenal endoluminal barrier. (See US Pat. Pub. No. 2011/0263490 entitled "Diagnostic Methods And Combination Therapies Involving MC4R" filed Dec. 29, 2010, which is hereby incorporated by reference in its entirety.) The treatments can be temporary. By temporarily performing the treatments, assessment of the efficacy of the treatment can be made. Moreover, as the treatment can be temporary, and possibly reversible, evaluating the efficacy of the treatment can influence whether additional treatments need to be performed or if the treatment alone is sufficient to attain the desired weight loss result.

Hormone and neuropeptide therapy can also be used to regulate or suppress appetite, increase body energy expenditure, and/or decrease fat mass accumulation (McMinn, J. E., Baskin, D. G. & Schwartz, M. W., Obes Rev 2000; 1:37-46; Drazen, D. L. & Woods, S. C., Curr. Opin. Clin. Nutr. Metab. Care 2003; 6:621-629).

Activation of brown adipose tissue (BAT) can further lead to mobilization of fat stores within brown adipocytes to increase fat metabolism. The controlled activation of BAT can be optimized, leading to weight loss by reducing the stores of triglycerides in white adipose tissue (WAT).

BAT activation can occur either directly or transcutaneously. Either can stimulate the sympathetic nervous system to physiologically activate BAT. Whether BAT is activated directly and/or transcutaneously, target areas for BAT stimulation can include areas in the vicinity of BAT depots, e.g., the nape of the neck, over the scapula, alongside the spinal cord, and around the kidneys. Any BAT depot can be selected for activation. In the course of treating a patient, BAT nerves can be stimulated at any one or more BAT depots and can be stimulated simultaneously, e.g., two or more BAT depots being concurrently stimulated, or stimulated sequentially, e.g., different BAT depots being stimulated at different times. Simultaneous stimulation of BAT can help encourage more and/or faster energy expenditure. Sequential stimulation of BAT can help prevent the "burning out" of target nerves and can help stimulate the creation of new BAT cells. Sequential nerve stimulation can include stimulating the same BAT depot more than once, with at least one other BAT depot being activated before activating a previously activated BAT depot.

Generally, direct activation of BAT can include implanting a device below the skin surface proximate to a BAT depot, e.g., within a BAT depot, and activating the device to deliver an electrical signal to the nerves innervating the BAT depot and/or to brown adipocytes directly. BAT itself is densely innervated, with each brown adipocyte being associated with its own nerve ending, which suggests that stimulating the BAT directly can target many if not all brown adipocytes and depolarize the nerves, leading to activation of BAT. The sympathetic nerves that innervate BAT can be accessed directly through standard surgical techniques, as will be appreciated by a person skilled in the art.

The electrical signal, whether transcutaneously or directly delivered to BAT, can be configured in a variety of ways. The stimulation "on" time amplitude can be higher for shorter periods and increased or decreased for longer periods of application. The electrical signal can have any "geometry" of the applied voltage, e.g., square waves, ramp waves, sine waves, triangular waves, and waveforms that contain multiple geometries. A transcutaneous device can be used to transcutaneously activate BAT through a variety of sizes, shapes, and configurations. Generally, the device can be configured to generate and/or deliver an electrical signal to tissue at predetermined intervals, in response to a manual trigger by the patient or other human, in response to a predetermined trigger event, or any combination thereof. In an exemplary embodiment, the transcutaneous device can include an electrical stimulation patch configured to be applied to an external skin surface and to deliver an electrical signal to tissue below the skin surface, e.g., to underlying BAT.

Stimulation of BAT using an electrical signal is described in further detail in US Pat. Pub. No. 2011/0270360 entitled "Methods And Devices For Activating Brown Adipose Tissue Using Electrical Energy" filed Dec. 29, 2010, and stimulation of BAT using other exemplary modes of stimulation are described in further detail in PCT Pat. App. No. PCT/US11/66399 entitled "Methods And Devices For Activating Brown Adipose Tissue With Targeted Substance Delivery" filed Dec. 21, 2011, PCT Pat. App. No. PCT/US11/66358 entitled "Brown Adipocyte Modification" filed Dec. 21, 2011, PCT Pat. App. No. PCT/US11/66409 entitled "Methods And Devices For Activating Brown Adipose Tissue With Light" filed Dec. 21, 2011, and PCT Pat. App. No. PCT/US11/66415 entitled "Methods And Devices For Activating Brown Adipose Tissue With Cooling" filed Dec. 21, 2011.

Genetic Indicators

As mentioned above, genetic indicators are one of the factors that can be used in predicting outcomes for different bariatric surgeries for a patient. It has been discovered that subjects with certain diagnostic markers respond to therapeutic interventions, such as gastric bypass surgery. A sample with DNA can be obtained from the subject, and the DNA can be evaluated for the presence or absence of one or more genetic indicators. The one or more genetic indicators can be considered in predicting outcomes for different bariatric surgeries, as discussed further below. Evaluating, identifying, obtaining, and using genetic indicators in connection with treating obesity is described in more detail in U.S. patent application Ser. No. 13/828,809 entitled "Clinical Predictors Of Weight Loss" filed on Mar. 14, 2013, which is incorporated herein by reference in its entirety.

Additional Indicators

Additional indicators can also be measured and used in predicting outcomes for different bariatric surgeries for a patient. Such indicators can include clinical measurements obtained from the patient. Examples of clinical measurements can include, but are not limited to, pre-operative BMI, a glucose tolerance, bile acid profile, and body composition/fat distribution of the subject. Pre-operative BMI can be greater than 25 kg/m$^2$.

Additional non-limiting examples of indicators include but are not limited to height, weight, gender, age, medical history and/or status, BMI, ethnicity, medical prescription history and/or status, types of previously received medical treatments for obesity (e.g., medications, BAT stimulation, gastric banding, gastric bypass, sleeve gastrectomy, etc), types of medical treatments previously received for health issues other than obesity (e.g., medications, surgical treatments, and non-surgical treatments), insurance information, diet information for the patient, and psychological history of the patient.

Computer System

The systems and methods disclosed herein can be implemented using one or more computer systems, which are also referred to herein as digital data processing systems. Various exemplary embodiments of computer systems are described in U.S. Pat. No. 8,036,912 entitled "Interactive Web Based System In Support Of Bariatric Procedures" issued Oct. 11, 2011, which is hereby incorporated by reference in its entirety.

FIG. 1 illustrates one exemplary embodiment of a computer system 100. As shown, the computer system 100 can include one or more processors 102 which can control the operation of the computer system 100. The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (I/O) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The I/O interface(s) 108 can include one or more interface components to connect the computer system 100 with other electronic equipment. For non-limiting example, the I/O interface(s) 108 can include high speed data ports, such as universal serial bus (USB) ports, 1394 ports, etc. Additionally, the computer system 100 can be accessible to a human user, and thus the I/O interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value is retained despite interruption of power to the computer system 100. The storage device(s) 110 can include one or more hard disk drives, flash drives, USB drives, optical drives, various media cards, and/or any combination thereof and can be directly connected to the computer system 100 or remotely connected thereto, such as over a network. The elements illustrated in FIG. 1 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing Hypertext Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

While some embodiments are described herein in the context of web pages, a person skilled in the art will appreciate that in other embodiments, one or more of the described functions can be performed without the use of web pages and/or by other than web browser software. A computer system can also include any of a variety of other software and/or hardware components, including by way of non-limiting example, operating systems and database management systems with or without access to a network. Although an exemplary computer system is depicted and described herein, it will be appreciated that this is for sake of generality and convenience. In other embodiments, the computer system may differ in architecture and operation from that shown and described here.

Bariatric Surgery Outcome Prediction System Generally

FIG. 2 is a schematic block diagram of one exemplary embodiment of a bariatric surgery outcome prediction system 10. The system 10 can include a plurality of modules, discussed further below, which can each be implemented using one or more digital data processing systems of the type described above, and in particular using one or more web pages which can be viewed, manipulated, and/or interacted with using such digital data processing systems. The system 10 can thus be implemented on a single computer system, or can be distributed across a plurality of computer systems. The system 10 also includes a plurality of databases, which can be stored on and accessed by computer systems. It will be appreciated that any of the modules or databases disclosed herein can be subdivided or can be combined with other modules or databases. The system 10 can be a computer-based system configured similar to embodiments described in previously mentioned U.S. Pat. No. 8,036,912 entitled "Interactive Web Based System In Support Of Bariatric Procedures" issued Oct. 11, 2011.

Any of a variety of parties can access, interact with, control, etc. the system 10 from any of a variety of locations. For non-limiting example, as shown in an embodiment illustrated in FIG. 3, the system 10 can be accessible over a network 12 (e.g., over the Internet via cloud computing) from any number of client stations 14 in any number of locations such as a medical facility 16 (e.g., a hospital, a medical clinic, a doctor's office, a mobile medical facility, etc.), a home base 18 (e.g., a patient's home or office, a doctor's home or office, etc.), a mobile location 20, and so forth. The client station(s) 14 can access the system 10 through a wired and/or wireless connection to the network 12. The system 10 can allow the client station(s) 14 to upload data to the system 10 over the network 12 and download data from the system 10 over the network 12. In an exemplary embodiment, at least some of the client terminal(s) 14 can access the system 10 wirelessly, e.g., through Wi-Fi connection(s), 3G connections, 4G connections, etc., which can facilitate accessibility of the system 10 from almost any location in the world. As shown in FIG. 3, the medical facility 16 includes client stations 14 in the form of a tablet and a computer touch screen, the home base 18 includes client stations 14 in the form of a mobile phone having a touch screen and a desktop computer, and the mobile location 20 includes client stations 14 in the form of a tablet and a mobile phone, but the medical facility 16, the home base 18, and the mobile location 20 can include any number and any type of client stations. In an exemplary embodiment, the system 10 can be accessible by a client terminal via a web address and/or a client application (generally referred to as an "app").

A person skilled in the art will appreciate that the system 10 can include security features such that the aspects of the system 10 available to any particular user can be determined based on the identity of the user and/or the location from which the user is accessing the system. To that end, each user can have a unique username, password, and/or other security credentials to facilitate access to the system 10. The received security parameter information can be checked against a database of authorized users to determine whether the user is authorized and to what extent the user is permitted to interact with the system, view information stored in the system, and so forth. Exemplary, non-limiting examples of parties who can be permitted to access the system 10 include patients, potential patients, surgical technicians, surgeons, nurses, general medical practitioners, and medical students.

The system 10 can include a patient data input module 200, a historical data input module 202, an outcome prediction module 204, and a medical practitioner locator module 206, and a seminar locator module 208. Any of the patient data input module 200, the historical data input module 202, the outcome prediction module 204, the medical practitioner locator module 206, and the seminar locator module 208 can be used independently from one another and can be used in combination with any one or more of the other modules 200, 202, 204, 206, 208. Each of the modules 200, 202, 204, 206, 208 is discussed further below in turn. Although each of the modules 200, 202, 204, 206, 208 is illustrated in FIG. 2 as a single-component module, each of the modules 200, 202, 204, 206, 208 can include any number of component modules, e.g., one, two, three, etc., the same or different from any of the other modules 200, 202, 204, 206, 208. Further, as mentioned above, it will be appreciated that any of the modules 200, 202, 204, 206, 208, and any of their various component modules, can be subdivided or can be combined with other modules, including modules illustrated in FIG. 2 as being in different ones of the modules 200, 202, 204, 206, 208.

The system 10 can also include a patient data database 300 configured to be accessible by the patient data input module 200 and to store patient data, a historical data database 302 configured to be accessible by the historical data input module 202 and to store historical data, an educational information database 304 configured to be accessible by the outcome prediction module 204 and to store educational data, a medical practitioner database 306 configured to be accessible by the medical practitioner locator module 206 and to store medical practitioner data, and a seminar database 308 configured to be accessible by the seminar locator module 208 and to store seminar data. Each of the databases 300, 302, 304, 306, 308 is discussed further below in turn with respect to their associated modules 200, 202, 204, 206, 208. Each of the databases 300, 302, 304, 306, 308 can include any number of component databases, e.g., one, two, three, etc., the same or different from any of the other databases 300, 302, 304, 306, 308. As mentioned above, a person skilled in the art will appreciate that any of the databases 300, 302, 304, 306, 308, and any of their various component databases (if any), can be subdivided or can be combined with other databases, including databases illustrated in FIG. 2 as being in different ones of the databases 300, 302, 304, 306, 308. Any portion of any of the databases 300, 302, 304, 306, 308 can be configured to be accessed, e.g., read from and/or written to, by any one or more of the modules 200, 202, 204, 206, 208 and any additional module(s) (if any). Although the system 10 in the illustrated embodiment stores data in database(s), any of the systems disclosed herein can store data in database(s) and/or in other data organization structure(s).

Users of the system 10 can include patients and medical practitioners involved with treating one or more of the patients. In some embodiments, the system 10 can be accessible by users other than patients and medical practitioners, such as by medical students, family members of patients, etc. Different users can have access to different portions of the system 10, as mentioned above regarding security features. For non-limiting example, the system 10 can be configured to allow patients to access the patient data input module 200, the outcome prediction module 204, the medical practitioner locator module 206, and the seminar locator module 208, to allow medical administrators to access only the historical data input module 202, and to allow medical professionals and medical students to access all of the modules 200, 202, 204, 206, 208. A user can have access to only a portion of a module, e.g., to only a subset of component modules within any one or more of the modules 200, 202, 204, 206, 208.

Figure 4:
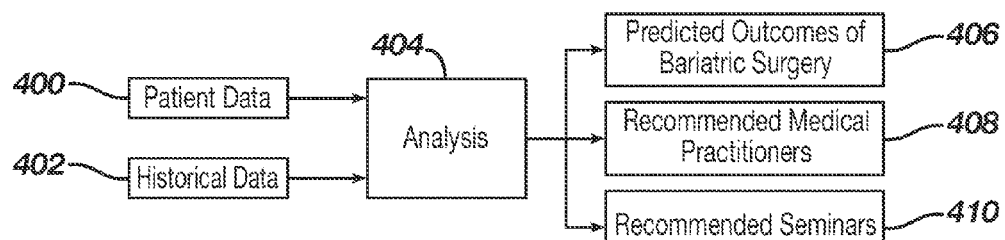
FIG. 4 is a schematic diagram of the metabolic and bariatric surgery outcome predictive system of FIG. 2.

Generally, as illustrated in FIG. 4, and as discussed in further detail below, the system 10 can be configured to allow patient data 400 to be input via the patient data input module 200 and historical data 402 to be input via the historical data input module 202. The outcome prediction module 204 can be configured to analyze 404 the input patient data 400 and the input historical data 402 so as to output one or more predicted outcomes of bariatric surgery 406. Optionally, the medical practitioner locator module 206 can be configured to analyze 404 the input patient data 400 and the input historical data 402 so as to output one or more recommended medical practitioners 408 for the patient, and/or the seminar locator module 208 can be configured to analyze 404 the input patient data 400 and the input historical data 402 so as to output one or more recommended seminars 410 for the patient.

Patient Data Input Module

The patient data input module 200 can generally provide users of the system 10 with an interface for entering data regarding patients and submitting the data to the system 10. The submitted patient data can then be used by the outcome prediction module 204 to predict bariatric surgery outcomes for the patient, as discussed further below.

As mentioned above, the patient data input module 200 can be configured to read information from and/or write information to the patient data database 300. Thus, the patient data input module 200 can be configured to write submitted patient data to the patient data database 300. The patient data can be organized in any way in the patient data database 300 and/or in one or more other storage areas accessible by the system 10. In an exemplary embodiment, patient data can be stored in a table in the patient data database 300 such that each patient has his/her own row or column of data populated with data related to that patient. However, as will be appreciated by a person skilled in the art, patient data can be stored in any way.

The patient data input module 200 can be configured to automatically gather patient data and/or can be configured to receive manually input patient data, e.g., receive patient data submitted thereto. In an exemplary embodiment, the patient data input module 200 can be configured to automatically gather data and to manually receive data, thereby maximizing an amount of data that the system 10 can consider in evaluating bariatric surgery outcomes for patients. By automatically gathering patient data, the patient data input module 200 can help ensure that the most recent and comprehensive patient data is available for analysis by the system 10, help account for accidental omission of manual patient data entry to the system 10, and/or help ensure that accurate patient data is received by the system 10. By allowing manual patient data entry, the patient data input module 200 can help allow data to be input and considered that is more current than data available in a storage unit automatically accessible by the patient data input module 200 and help allow input and consideration of data not accessible through automatic data gathering.

The patient data input module 200 can be configured to automatically gather patient data in a variety of ways. In an exemplary embodiment, the patient data input module 200 can be configured to transmit a request for patient data information to one or more storage units storing patient data, e.g., patient medical records stored at a medical facility such as a hospital, doctor's office, clinic, etc., patient insurance information stored at a medical facility, insurance carrier office, etc., and other types of patient data. In response to the request, the one or more storage units can transmit the requested patient data to the patient input data module 200. To help ensure confidentiality of patient data, any one or more security measures can be taken in requesting and/or transmitting the data, such as encrypting the patient data request, encrypting the transmitted patient data, authenticating the patient data input module 200 via one or more authentication mechanisms (e.g., passwords, keys, etc.), temporarily storing the patient data for a single user session (e.g., storing the patient data until the user who requested automatic gathering of the patient data logs off the system 10), etc.

The patient data input module 200 can be configured to automatically gather patient data at predetermined time intervals and/or on demand (e.g., by user request after user login to the system 10 over the network 12). The predetermined time intervals can be preset, and can be any time interval, e.g., every thirty days, every six months, every day, etc. The predetermined time intervals can be the same for all patients or different for different patients. For non-limiting example, the patient data input module 200 can be configured to automatically gather patient data from certain medical facilities (e.g., hospitals) more frequently than other medical facilities (e.g., clinics) because patients visiting the certain medical facilities which provide specialized medical care can be considered to be more likely candidates for bariatric surgery than patients visiting the other medical facilities which provide more generalized medical care, and hence more likely users of the system 10.

The patient data input module 200 can be configured to receive patient data manually submitted thereto in a variety of ways. In one embodiment, the patient data input module 200 can be implemented using one or more web pages which are configured to receive user input and present information to a user. In an exemplary embodiment, both patients and medical practitioners can access at least a portion of the patient data input module 200. In an exemplary embodiment, the patient data input module 200 can be accessed by users via a web interface, e.g., by connecting to the Internet via a client terminal and accessing a specific web address, by launching an app on a client terminal that accesses the system 10, etc. As mentioned above, the users can wirelessly access the system 10, including the patient data input module 200, and can submit the data to the system 10 via the web, e.g., by clicking on a "submit" button on a web page.

The patient data input module 200 can be configured to receive a variety of different types of data regarding a patient. Non-limiting examples of patient data that can be received (automatically and/or manually) by the patient data input module 200 include identification data, clinical data, and genetic data. Non-limiting examples of identification data include a unique patient identifier (e.g., a name, a social security number, an insurance identification code, a system logon name, a hospital identification code), a geographic location of the patient (e.g., country, zip code, etc.), etc. Non-limiting examples of clinical data include a height of the patient, a weight of the patient, a waist circumference of the patient, a waist to hip ration of the patient, a gender of the patient, an age of the patient, a medical history of the patient, a medical status of the patient (e.g., a diabetes status of the patient, a hypertension status of the patient, etc.), a patient's family medical history, a BMI of the patient (e.g., a current or pre-operative BMI of the patient), medical images (e.g., x-ray, computed tomography (CT) scan, magnetic resonance imaging (MRI), positron emission tomography (PET), etc.) previously taken of the patient, an ethnicity of the patient, a medical prescription history of the patient, a medical prescription status of the patient, types of medical treatments for obesity previously received by the patient, types of medical treatments for health issues other than obesity previously received by the patient, insurance information for the patient, diet information (e.g., caloric intake, food preferences, cravings, etc.) for the patient, appetitive drive (e.g., hunger, satiety, satiation, hedonic, etc.) of the patient, body composition of the patient, fat distribution in the patient, provocative data (e.g., data regarding patient response to Melanocortin receptor 4 (MC4R) therapy (e.g., as described in previously mentioned US Pat. Pub. No. 2011/0263490 entitled "Diagnostic Methods And Combination Therapies Involving MC4R" filed Dec. 29, 2010), an endoluminal barrier, BAT stimulation, hormone and neuropeptide therapy, etc.) for the patient, physiologic data (e.g., bile acids, Glucagon-like peptide-1 (GLP-1), Peptide YY (PYY) levels, gene expression, metabolite panels, proteomic results, testosterone levels, etc.) for the patient, factors associated with surgical risk (e.g., airway risks, smoking history, prior surgical procedures in the abdomen, etc.), and psychological history of the patient. As will be appreciated by a person skilled in the art, patient clinical data can be collected in a variety of ways, such as being sampled, provoked, etc. Non-limiting examples of genetic data include a genetic indicator of the patient. In an exemplary embodiment, the genetic indicator can include one or more of the genetic indicators discussed in previously mentioned U.S. patent application Ser. No. 13/828,809 entitled "Clinical Predictors Of Weight Loss" filed on Mar. 14, 2013.

The web interface configured to allow users to access the patient data input module 200 can have a variety of configurations. Users who access the system 10 may or may not be the same person as the patient for whom the user is inputting patient data and/or requesting predicted outcomes of bariatric surgery. The web interface can be configured to be displayed on a client terminal, as can any of the various web interfaces described herein.

Figure 5:
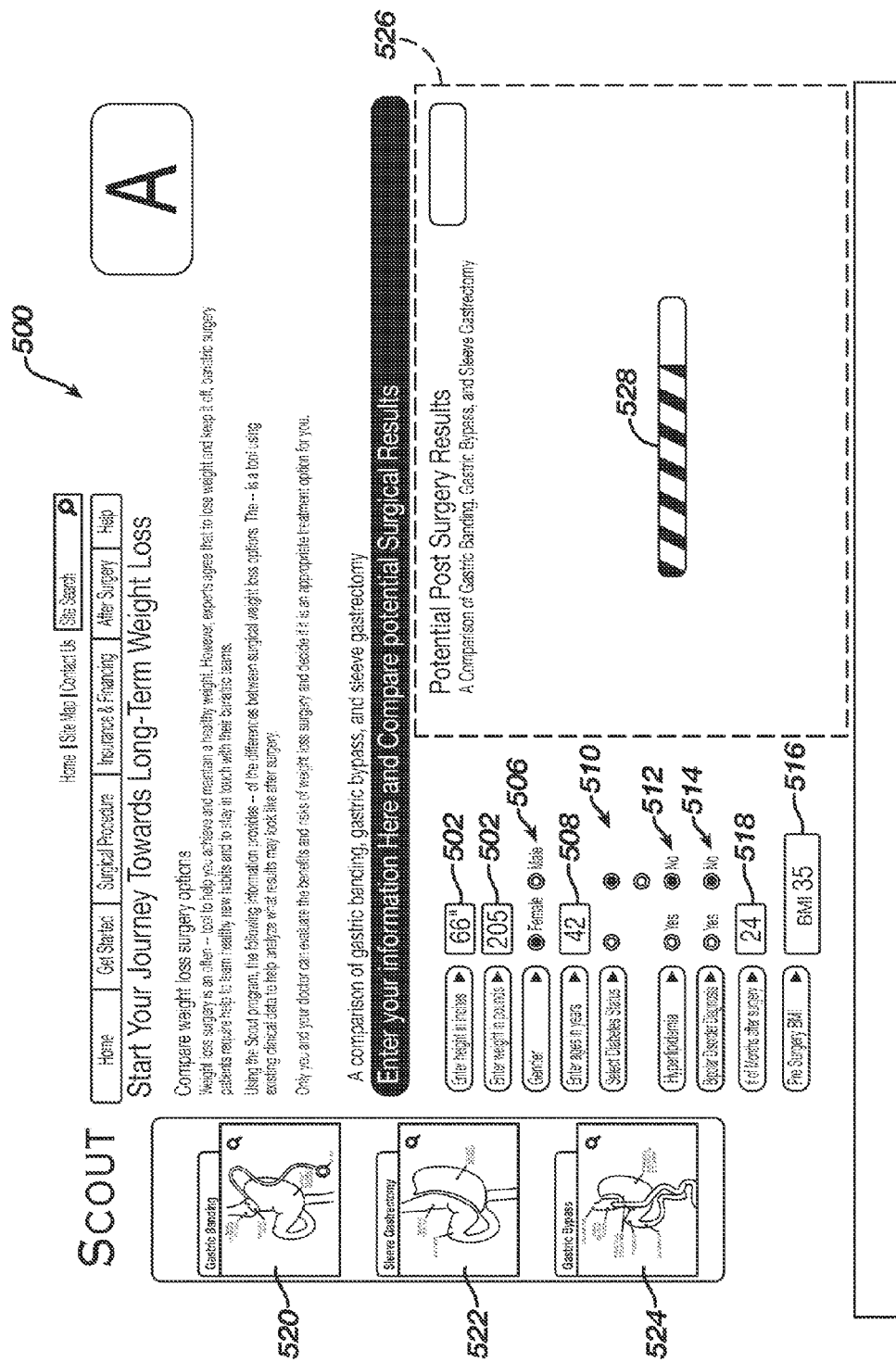
FIG. 5 is a schematic diagram of an embodiment of a patient data and predicted outcome web interface of the metabolic and bariatric surgery outcome predictive system of FIG. 2; metabolic

FIG. 5 illustrates one embodiment of a patient data web interface 500 configured to be displayed on a client terminal and to allow input of patient data thereto. The patient data web interface 500 can identify one or more bariatric surgical procedures for which the input patient data can be analyzed, as discussed further below, to predict an outcome for the patient if the patient had that bariatric procedure performed on him/her. In the illustrated embodiment, the identified bariatric surgical procedures are gastric banding, sleeve gastrectomy, and gastric bypass. Gastric banding, sleeve gastrectomy, and gastric bypass are the most common bariatric surgical procedures performed and are thus the bariatric surgical procedures for which the most historical data can be collected. Thus, in an exemplary embodiment, the system 10 can be configured to predict outcomes for at least gastric banding, sleeve gastrectomy, and gastric bypass. The system 10 can thus allow predicted outcomes for multiple bariatric surgical procedures, e.g., gastric banding, sleeve gastrectomy, and gastric bypass, to be directly compared against one another, which can help allow users such as patients and medical practitioners to make better, more informed decisions as to which bariatric procedure may be most effective for a particular patient and thus the bariatric procedure to pursue, at least initially, for the particular patient. Although the bariatric surgical procedures are pre-selected in the illustrated embodiment of FIG. 5, in some embodiments, the system 10 can be configured to allow the user to select which one or more bariatric surgical procedures to analyze for the particular patient whose data is input to the system 10 and/or be configured to allow the user to select which one or more non-surgical treatments (e.g., doing nothing, diet, exercise, pharmaceutical therapy, etc.) to analyze for the particular patient whose data is input to the system 10. By allowing the user to select both surgical and non-surgical treatments, the system 10 can allow the user to more fully evaluate different treatment options. Historical data regarding non-surgical treatments can be gathered, stored, and analyzed similar to that discussed herein for surgical treatments.

In the illustrated embodiment, the patient data web interface 500 includes patient data entry fields including a height field 502 (asking for height to be entered in inches, although entry in any length unit can be requested or provided on any patient data web interface), a weight field 504 (asking for weight to be entered in pounds, although entry in any weight unit can be requested or provided on any patient data web interface), a gender field 506, an age field 508 (asking for age to be entered in years, although entry in any time unit can be requested or provided on any patient data web interface), a diabetes status field 510, a hyperlipidemia (high blood cholesterol level) status field 512, a bipolar disorder diagnosis field 514, and a pre-surgery BMI field 516. Diabetes is often a disease afflicting obese patients and is also a disease which has a causal treatment or cure relationship with at least some bariatric surgical procedures, as discussed in, e.g., U.S. patent application Ser. No. 13/828,809 entitled "Clinical Predictors Of Weight Loss" filed on Mar. 14, 2013, and in Schauer et al. "Bariatric Surgery versus Intensive Medical Therapy in Obese Patients with Diabetes." *New England Journal of Medicine* 2012; 366(17):1567-1576. Thus, requesting and receiving information regarding a patient's diabetes status can allow the system 10 to provide predicted outcomes for the patient's diabetes, in addition to at least predicted outcomes for weight loss and/or BMI reduction, following one or more bariatric procedure(s).

The patient data web interface 500 also includes a post-surgery time field 518 (asking for time to be entered in months, although entry in any time unit can be requested or provided) in which a user can enter a length of time post-surgery at which the system 10 provides a predicted patient outcome. In some embodiments, a post-surgery time is not requested from a user because the system 10 can be configured to provide analysis at one or more predetermined post-surgery times, e.g., 1 month, 3 months, 6 months, 9 months, 12 months, 18 months, 24 months, 36 months, 48 months, 60 months, 72 months, 84 months, 96 months, 108 months, 120 months, etc. Having predetermined post-surgery time(s) can help the system 10 analyze data faster, which can improve a user experience by reducing a wait time for predicted outcome results, and/or can facilitate consideration of historical surgical outcome data, which is typically gathered at predetermined time intervals that can correspond to the system's predetermined post-surgery times. In an exemplary embodiment, the system 10 can be configured to provide analysis at a plurality of predetermined post-surgery times, such as at each of 1 month, 3 months, 6 months, 9 months, 12 months, 18 months, 24 months, 36 months, 48 months, 60 months, 72 months, 84 months, 96 months, 108 months, 120 months, and one or more 12 month increments thereafter, which can allow both short term and long term predicted bariatric surgery results to be available for analysis by the system 10 and display to the user.

Any one or more of the fields 502, 504, 506, 508, 510, 512, 514, 516, 518 of the patient data web interface 500 can, as can any field of any web interface provided by the system 10, allow data entry thereto in any number of ways, as will be appreciated by a person skilled in the art, such as by text box, radio button, push button, drop-down menu, list box, check box, cycle button, etc. Similarly, any web interface provided by the system 10 can allow data entry thereto in any number of ways.

Any one or more of the fields 502, 504, 506, 508, 510, 512, 514, 516, 518 can, as can any field of any web interface provided by the system 10, be configured to be exclusively automatically populated with patient data (such as if the patient data input module 200 is configured to automatically retrieve patient data from the patient data database 300 (e.g., retrieve patient data previously entered by the user into the system 10 and saved in the patient data database 300, retrieve patient data from one or more remote storage units, retrieve patient data from the patient data database 300 previously automatically retrieved by the patient data input module 200 according to a predetermined data retrieval schedule, etc.)), exclusively manually populated with patient data (such as if the patient data input module 200 is not configured to automatically retrieve patient data or to conserve processing resources), or to be manually or automatically populated.

The patient data web interface 500 can, as can any web interface provided by the system 10, be configured to allow user access to one or more educational materials stored in the educational information database 304 in any number of ways. In the illustrated embodiment, the patient data web interface 500 is configured to allow a user to select, e.g., scroll over, click on an hourglass icon thereon, etc., one or more of a gastric banding information box 520, a sleeve gastrectomy information box 522, and a gastric bypass information box 524. The information boxes 520, 522, 524 each identify its associated procedure by name and show an image of the procedure's manipulation of a stomach, which can help the user easily, visually distinguish between the different surgical procedures. However, the information boxes 520, 522, 524 can each include more or less information, same or different from one another. In response to the user selecting one or more of the boxes 520, 522, 524, the patient data input module 200 can be configured to retrieve one or more educational materials related to the selected procedure(s) from the educational information database 304 and cause the educational materials and/or links thereto to be displayed on the patient data web interface 500 directly, on the patient data web interface 500 in a pop-up box, on another web interface, etc. The system 10 can therefore be configured to help educate the user about different bariatric surgery options. Non-limiting examples of educational materials include links to informational web pages stored in the system 10 (e.g., in the educational information database 304), links to third party educational websites, lists of or links to journal articles or books, educational video of a surgical procedure that is stored in the system 10 (e.g., in the educational information database 304), links to and/or copies of medical device product brochures (e.g., brochures stored electronically in the system 10), statistics regarding a number of bariatric procedures performed over a last "X" amount of time and/or in a certain geographic region, brief description (text, audio, and/or video) of typical steps of a bariatric surgical procedure, brief description (text, audio, and/or video) of typical post-surgery recovery and treatment following a bariatric surgical procedure, etc.

Figure 6:
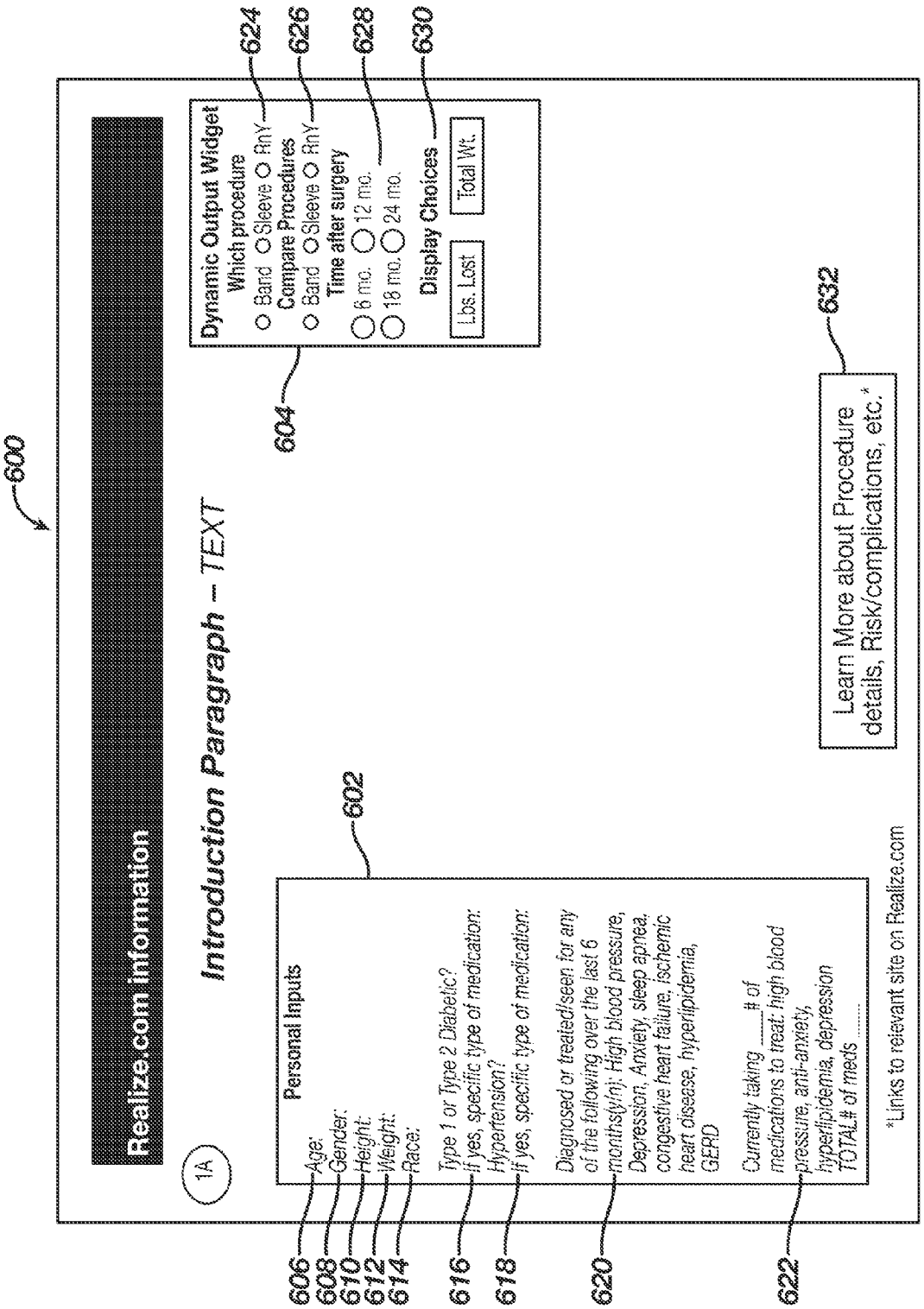
FIG. 6 is a schematic diagram of an embodiment of a patient data web interface of the metabolic and bariatric surgery outcome predictive system of FIG. 2.

FIG. 6 illustrates another embodiment of a patient data web interface 600 configured to be displayed on a client terminal and to allow input of patient data thereto. The patient data web interface 600 can include a patient data input area 602 and a surgical procedure data input area 604. The patient data input area 602 can allow user input thereto of data related to a patient. In the illustrated embodiment, the patient data input area 602 includes patient data entry fields including an age field 606, a gender field 608, a height field 610, a weight field 612, a race field 614, a diabetic status field 616, a hypertension status field 618, a medical diagnosis/treatment field 620, and a medication status field 622. The diabetic status field 616 can allow the user to indicate whether the patient has Type 1 or Type 2 diabetes and, if so, indicate any medications the patient is taking for the diabetes. Various types of medications may affect which bariatric surgical procedures are appropriate for a patient because some medications, diabetes-related medications as well as other medications such as psychiatric/neurological medications, steroid hormones, progestational steroids, antihyperactive agents, and antihistamines, may have adverse effects if taken in conjunction with medications typically taken by patients who will or have had a certain type of bariatric surgical procedure. See, e.g., "Obesity Treatment Guide: A reference for assessing and treating overweight and obese patients," Physician Handout available from *Bariatric Times* website at <http://bariatrictimes.com/about/> (accessed Sep. 19, 2012). The hypertension status field 618 can allow the user to indicate whether the patient has hypertension and, if so, indicate any medications the patient is taking for the hypertension. Hypertension is often a disease afflicting obese patients and is also a disease which has a causal treatment or cure relationship with at least some bariatric surgical procedures. See, e.g., Buchwald et al., "Bariatric surgery: a systematic review and meta-analysis." *JAMA*. 2004. 292(14):1724-37. Thus, requesting and receiving information regarding a patient's hypertension status can allow the system 10 to provide predicted outcomes for the patient's hypertension, in addition to at least predicted outcomes for weight loss and/or BMI reduction, following one or more bariatric procedure(s).

The surgical procedure data input area 604 can allow user input thereto of data related to bariatric surgical procedure(s) for which the user desired to see predicted outcome(s). The surgical procedure data input area 604 can allow user input thereto of data related to bariatric surgical procedures. In the illustrated embodiment, the surgical procedure data input area 604 includes bariatric surgery data entry fields including a bariatric procedure selection field 624, a bariatric procedure comparison selection field 626, a post-surgery time field 628, and a post-surgery weight outcome selection field 630. The bariatric procedure selection field 624 and the bariatric procedure comparison selection field 626 can allow the user to select one or more bariatric surgical procedures of particular interest to the user, which can help provide more meaningful information to the user and/or can help reduce processing time in predicting surgical outcomes for the patient because fewer surgical procedures may be considered than a maximum number of procedures available for analysis. The post-surgery weight outcome selection field 630 can allow a user to select whether patient weight lost, e.g., pounds lost, and/or total patient weight are predicted by the system 10, e.g., by the outcome prediction module 204, and displayed to the user.

The patient data web interface 600 can be configured to allow user access to one or more educational materials stored in the educational information database 304 by providing an educational information box 632 configured to be clicked or otherwise selected by the user to access educational materials. In the illustrated embodiment, the user clicking or otherwise selecting the educational information box 632 causes the user to access via link another portion of the system 10, although as mentioned above, educational materials can be provided in any way.

FIG. 7 illustrates another embodiment of a patient data web interface 700 configured to be displayed on a client terminal and to allow input of patient data thereto. In the illustrated embodiment, the patient data web interface 700 includes patient data entry fields including a height field 702 in drop-down menu form and a weight field 704 in text box form.

FIGS. 8-10 illustrate another embodiment of a patient data web interface 800 configured to be displayed on a client terminal and to allow input of patient data thereto. FIG. 9 illustrates the patient data web interface 800 having patient data input thereto for a first patient, and FIG. 10 illustrates the patient data web interface 800 having patient data input thereto for a second patient. The input patient data in FIGS. 9 and 10 are non-limiting examples and do not correspond to any particular actual patient.

The patient data web interface 800 can include a personal information input area 802 in which a user can input personal information regarding a patient, a current (medical) conditions area 804 in which a user can input current (medical) conditions of a patient, and a current medications area 806 in which a user can input current medications being taken by and/or prescribed to a patient. The different areas 802, 804, 806 can each be configured to include a plurality of data entry fields. In the illustrated embodiment, the personal information input area 802 includes personal information data entry fields including an age field 808, a gender field 810, a height field 812, a weight field 814, a race field 816, and an ethnicity field 818; the current (medical) conditions area 804 includes a list 820 of medical conditions (asthma/COPD, depression, diabetes (Type 2), GERD/histal hernia, hyperlipidemia, hypertension, knee/hip/back surgery, liver disease, obst sleep apnea, other breathing difficulties, etc.) that the user can indicate (e.g., by Yes/No radio button selection, by drop-down menu selection, etc.) as being a medical condition of the patient or not; and the current medications area 806 includes a list 822 of medical conditions (depression, diabetes (Type 2), hyperlipidemia, hypertension (e.g., diuretics, alpha blockers, beta blockers, c-channel blockers, etc.) which can be treated by medication that the user can indicate (e.g., by Yes/No radio button selection, by drop-down menu selection, etc.) as being treated by a medication currently being taken and/or prescribed to the patient. All of the medical conditions in the list 820 can be medical conditions that bariatric surgery can affect, e.g., improve a diagnosis thereof, and that can have predicted outcomes calculated and displayed therefor. Alternatively, one or more of the medical conditions in the list 820 can be medical conditions that bariatric surgery is not known to affect, e.g., is not known to affect a diagnosis thereof, and/or is not known to have a strong correlation with, e.g., is not known to affect a diagnosis thereof, and that does not have predicted outcomes calculated and displayed therefor. In an exemplary embodiment, the list 820 can include one or more medical conditions that bariatric surgery can affect and one or more of the medical conditions that bariatric surgery is not known to affect and/or is not known to have a strong correlation with. By including one or more medical conditions that bariatric surgery is not known to affect and/or is not known to have a strong correlation with along with one or more medical conditions that bariatric surgery can affect, the list 820 itself can help improve a user's understanding of the different medical conditions in the list 820, thereby helping to improve accuracy of the user's selections in the list 820 and accordant analysis thereof. For non-limiting example, asthma is not known to have a strong correlation with bariatric surgery, but by including asthma in the list 820 along with breathing difficulties, which is known to be affected by bariatric surgery, a user will be less likely to select "breathing difficulties" as a problem of a patient if asthma is the patient's only breathing problem. The system 10 can thus not calculate and present predicted "breathing difficulty" outcomes if "asthma," but not "breathing difficulties," is selected.

Fields having numerical inputs can be configured to accept data in one or more units and be configured to automatically convert the data input in one of the units to the other units. If input values are outside of a range for the system 10 (e.g., a height entered beyond a predetermined threshold indicating an upper height limit which adult humans do not presently exceed, etc.), the system 10 can be configured to display an error message indicating an appropriate corrective action, e.g., entering a new number, removing a decimal point, etc. For non-limiting example, weight entered in pounds in a pounds data field in the weight field 814 can be automatically converted to weight in kilograms, and a kilograms data field in the weight field 814 can be automatically populated. For another non-limiting example, height entered in feet and inches in feet and inches data fields in the height field 812 can be automatically converted to height in centimeters, and a centimeters data field in the height field 812 can be automatically populated.

Any of the fields in any of the areas 802, 804, 806 can be configured to accept only predetermined answers thereto, e.g., not be a text box in which a user can enter any text. The input data can therefore be one of a plurality of possible user selections, thereby allowing the system 10 to accurately identify and analyze input data. In the illustrated embodiment, the race field 816, the ethnicity field 818, and selected portions of the list 822 of medical conditions (depression, diabetes (Type 2), and hyperlipidemia) allow predetermined answers by providing drop-down menus of possible answers that can be selected by a user, and the gender field 810, the list 820 of medical conditions, and selected portions of the list 822 of medical conditions being treated by a medication allow predetermined answers by providing radio buttons in which a user can only select one for each field 810 and above-identified list 820, 822 item.

The patient data web interface 800 can include a submitter 824 configured to allow user inputs to the areas 802, 804, 808 to be submitted to the system 10. The submitter 824 in the illustrated embodiment includes a clickable button marked "GO," but any text (e.g., "OK," "submit," "calculate," etc.) can be on the button. Further, the submitter need not be a clickable button, as will be appreciated by a person skilled in the art, but can be any submission mechanism, such as a check box, an audio command receiver, a user movement detector for a touch pad or touch screen, etc.

In some embodiments, a user's selection of a predetermined answer, e.g., "yes" from "yes/no," inputting a check box next to a particular medical condition, etc., can be configured to trigger display and/or activation of one or more additional fields for the user to complete. For non-limiting example, selecting a particular medical condition as being an affliction of a patient can trigger display and/or activation of a medication field for that particular medical condition in which the user can indicate any medications being taken to treat the particular medical condition. For another non-limiting example, indicating that a patient is currently taking a medication can trigger display and/or activation of a time field in which the user is prompted to enter how long (e.g., number of days, weeks, months, years, etc.) the patient has been taking the medication. Similarly, in some embodiments, a user's entry of certain text in a text box can trigger display and/or activation of one or more additional fields for the user to complete. For non-limiting example, a user entering an age in a predetermined range can trigger a first set of one or more questions appropriate for that age range, and a user entering an age in another predetermined range can trigger a second, different set of one or more questions appropriate for that age range.

In some embodiments, a user's selection of a predetermined answer or entry of certain text in a text box can cause predetermined information to be displayed on the patient data web interface. For non-limiting example, user entry of a patient's height and a patient's weight can trigger display of the patient's BMI (i.e., $wt/(ht)^2$) on the patient data web interface. If the patient's weight is not entered in kilograms and/or if the patient's height is not entered in meters, the system 10 can be configured to convert the entered weight and/or height to the appropriate unit for calculation of BMI in which a person's body weight in kilograms is divided by the square of his or her height in meters (i.e., $wt/(ht)^2$). For another non-limiting example, user entry of a patient's height in one unit, e.g., feet/inches, can trigger display of the patient's height in one or more other height units, e.g., centimeters, meters, etc.

Historical Data Input Module

The historical data input module 202 can generally provide users of the system 10 with an interface for entering data regarding previously performed bariatric surgeries and submitting the data to the system 10. The submitted patient data can then be used by the outcome prediction module 206 to predict bariatric surgery outcomes for a patient, as discussed further below.

As mentioned above, the historical data input module 202 can be configured to read information from and/or write information to the historical data database 302. Thus, the historical data input module 202 can be configured to write submitted historical data to the historical data database 302. The historical data can be organized in any way in the historical data database 302 and/or in one or more other storage areas accessible by the system 10.

The historical data input module 202 can be configured to automatically gather historical data and/or can be configured to receive manually input historical data, e.g., receive historical data submitted thereto. In an exemplary embodiment, the historical data input module 202 can be configured to automatically gather data and to manually receive data, thereby maximizing an amount of data that the system 10 can consider in evaluating bariatric surgery outcomes for patients. By automatically gathering patient data, the historical data input module 202 can help ensure that the most recent and comprehensive data is available for analysis by the system 10, help account for accidental omission of manual historical data entry to the system 10, and/or help ensure that accurate historical data is received by the system 10. By allowing manual historical data entry, the historical data input module 202 can help allow data to be input and considered that is more current than data available in a storage unit automatically accessible by the historical data input module 202 and help allow input and consideration of data not accessible through automatic data gathering.

The historical data input module 202 can be configured to automatically gather historical data in a variety of ways. In an exemplary embodiment, the historical data input module 202 can be configured to transmit a request for historical data information to one or more storage units storing historical data, e.g., clinical trial data stored at a medical facility such as a hospital, doctor's office, clinic, etc., insurance reimbursement information stored at a medical facility, insurance carrier office, Thomson Reuters MarketScan®, etc., joint registry data, Longitudinal Assessment of Bariatric Surgery (LABS) data, Bariatric Outcomes Longitudinal Database (BOLD), Premier hospital database, MedAssets data, Ingenix/I3 data, Gesinger data, MedPar data, HCUP data, national health care databases (e.g., databases indexed by the International Society for Pharmacoeconomics and Outcomes Research (ISPOR) such as the National Institute of Statistics and Censuses database of Argentina and the National Health and Wellness Survey database of France) (available at ISPOR website at <http://www.ispor.org/DigestOfintDB/CountryListaspx> (accessed Sep. 19, 2012)), and other types of historical data. Relevant historical data (e.g., data related to specific bariatric surgical procedures, data related to specific post-surgery complications, data related to specific comorbidities, etc.) can be identified in and retrieved from stored historical data, e.g., stored in an external database, in a variety of ways, as will be appreciated by a person skilled in the art, such as by identifying and retrieving data associated with a specific International Classification of Diseases (ICD) code (e.g., a specific ICD-9 code) or a specific Current Procedural Terminology (CPT) code. In response to the request, the one or more storage units can transmit the requested historical data to the historical data input module 202. To help ensure confidentiality of historical data, any one or more security measures can be taken in requesting and/or transmitting the data, such as encrypting the historical data request, encrypting the transmitted historical data, authenticating the historical data input module 202 via one or more authentication mechanisms (e.g., passwords, keys, etc.), storing data in the historical data database 302 without any specific patient identifiers (e.g., data not being associated with a particular patient name, patient identification code, etc.), etc.

The historical data input module 202 can be configured to automatically gather historical data at predetermined time intervals and/or on demand (e.g., by user request after user login to the system 10 over the network 12). The predetermined time intervals can be preset, and can be any time interval, e.g., every thirty days, every six months, every day, etc. The predetermined time intervals can be the same for all types of historical data or different for different types of historical data. For non-limiting example, the historical data input module 202 can be configured to automatically gather historical data from certain medical facilities (e.g., hospitals) more frequently than other medical facilities (e.g., clinics) because patients visiting the certain medical facilities which provide specialized medical care can be considered to be more likely candidates for bariatric surgery than patients visiting the other medical facilities which provide more generalized medical care, and hence more likely users of the system 10.

The historical data input module 202 can be configured to receive historical data manually submitted thereto in a variety of ways. In one embodiment, the historical data input module 202 can be implemented using one or more web pages which are configured to receive user input and present information to a user. In an exemplary embodiment, medical practitioners but not patients can access at least a portion of the historical data input module 202. In an exemplary embodiment, the historical data input module 202 can be accessed by users via a web interface, e.g., by connecting to the Internet via a client terminal and accessing a specific web address, by launching an app on a client terminal that accesses the system 10, etc. As mentioned above, the users can wirelessly access the system 10, including the historical data input module 202, and can submit the data to the system 10 via the web, e.g., by clicking on a "submit" button on a web page. For non-limiting example, historical data can be manually entered by one or more medical professionals performing a check-up on a patient previously having had bariatric surgery performed thereon by entering the patient's check-up data into a computer system maintaining patient data. The computer system can be the system 10 or another system configured to communicate with the system 10. The patient's check-up data can thus be stored in the historical data database 302.

The historical data input module 202 can be configured to receive a variety of different types of historical data regarding previously performed bariatric surgeries. Non-limiting examples of historical data that can be received (automatically and/or manually) by the historical data input module 202 include an amount of weight lost by a patient having had a bariatric surgery performed thereon, a change in one or more medical conditions for a patient having had a bariatric surgery performed thereon, a change in one or more medications being taken by a patient having had a bariatric surgery performed thereon, any follow-up surgical procedures having been performed on a patient having had a bariatric surgery performed thereon, and a genetic indicator of a patient having had a bariatric surgery performed thereon. In an exemplary embodiment, the genetic indicator can include one or more of the genetic indicators associated with obesity discussed in previously mentioned U.S. patent application Ser. No. 13/828,809 entitled "Clinical Predictors Of Weight Loss" filed on Mar. 14, 2013. Historical data can be received as being associated with a specific type of bariatric surgery, thereby allowing the historical data to be analyzed by the outcome prediction module 204 in relation to that specific type of bariatric surgery, and as associated a specific set of patient characteristics, thereby allowing the historical data to be analyzed by the outcome prediction module 204 in relation to other patients having the same or a same subset of those characteristics.

Any of the types of historical data can be received for different time points after a patient has a bariatric surgery performed thereon. In an exemplary embodiment, types of historical data can be received for predetermined times after a patient has a bariatric surgery performed thereon, e.g., six months after, twelve months after, etc. The data can therefore be more effectively analyzed by being more accurately statistically compared against other data. The predetermined times can correspond to typical post-surgery check-up times, which are typically every six months or every twelve months. For non-limiting example, historical data can be collected indicating how much weight patients lost 1 month, 3 months, 6 months, 9 months, 12 months, 18 months, 24 months, 36 months, 48 months, 60 months, 72 months, 84 months, 96 months, 108 months, 120 months, etc. after having has a bariatric procedure performed thereon. In this way, historical data can be collected regarding a plurality of patients each having has the same type of bariatric procedure performed thereon, each of the patients.

The web interface configured to allow users to access the historical data input module 202 can have a variety of configurations and can generally be configured similar to any of the web interfaces discussed above for the patient data input module 200.

Outcome Prediction Module

The outcome prediction module 204 can generally provide users of the system 10 with an interface for receiving one or more predicted outcomes of bariatric surgery for a patient. Various predictive analyses can be performed by the outcome prediction module 204, and various models can be used in performing the predictive analyses.

In general, predictive models require good databases, e.g., collections of reliable data. Non-limiting examples of characteristics of a good database for the outcome prediction module 204 include longitudinal patient data and large data sets. How "large" the data set should be to ensure sound predictions depends on a strength of correlations. Longitudinal data generally includes data both before and after surgery with a sufficient number of points in between, e.g., a statistically significant number of points in between, and includes inputs and outputs in sufficient numbers, e.g., statistically significant numbers, to determine correlations. Non-limiting examples of longitudinal data include clinical measures (e.g., pre-op weight, weight at time of surgery, weight at multiple time points after surgery, etc.), genetic measures, provocative measures, physiological measures, and economic measures (e.g., pre-op costs, surgical cost, length of hospital stay, post-op care, long term follow up, time out of work, etc.). Non-limiting examples of inputs include height, weight, BMI, medication usage, medical history, gender, education level, capacity for physical activity, and labs. Non-limiting examples of outputs include weight change, medication usage, medical history, labs, and costs.

With access to a good database, which can include one or more separate databases, the outcome prediction module 204 can be configured to identify if correlations can be determined between potential inputs and outputs. In an exemplary embodiment, the outcome prediction module 204 can be configured to perform this identification without bias, in an agnostic way to let the data from the database(s) reveal what the correlations are. A non-limiting example of a correlation includes % WC (percent weight change) correlating more strongly to pBMI (patient BMI) than % EBWL (percent excess body weight loss).

The predictive model(s) used by the outcome prediction module 204 can be created in a variety of ways. In general, as will be appreciated by a person skilled in the art, with a known set of variables that have strong correlations, these models can be modeled (e.g., equations can be developed that relate input variables to output variables), and coefficients to these equations can be determined by fitting the models to a set of data set aside to "train" the model. Non-limiting examples of predictive models that can be used by the outcome prediction module 204 include predictive models of weight change outcomes after bariatric surgery, comorbidity changes after bariatric surgery, morbidity and mortality rates after surgery, and monetary cost associated with surgery. A plurality of predictive models (e.g., any two or more of predictive models of weight change outcomes after bariatric surgery, comorbidity changes after bariatric surgery, morbidity and mortality rates after surgery, and monetary cost associated with surgery) can be personalized on a patient by patient basis and can be used to inform treatment decisions between, e.g., health care physician (e.g., surgeon, primary care physician, referring physician (endocrinologist, OB/GYN, etc.), etc.) and patient; hospital and health care physician; and health care physician, patient, and insurance company.

The model(s) used by the outcome prediction module 204 can be validated, as will be appreciated by a person skilled in the art. In general, with a model with a best-fit set of coefficients, a "test" set of data can be used to validate the predictive capabilities of the model. Using the input data from the "test" set as inputs to the models, outputs can be calculated and compared to the actual outputs. A comparison can be made between the predicted outcomes and the actual outcomes in the "test" set to determine how well the models are able to predict outcomes. If they meet a threshold of closeness, the model can be considered validated.

In an exemplary embodiment, the outcome prediction module 204 can be configured to provide a user of the system 10 with at least one predicted outcome for each of a plurality of different bariatric surgical procedures for a patient, thereby facilitating comparison between the different bariatric surgical procedures. In other words, the outcome prediction module 204 can be configured to facilitate comparison between different possible outcomes of different bariatric surgeries for a patient, thereby helping the user determine which, if any, of the bariatric surgeries may be valuable to pursue as a treatment option for the patient.

Non-limiting examples of outcomes that the outcome prediction module 204 can be configured to predict include amount of weight loss after bariatric surgery, weight after bariatric surgery, decreased comorbidities after bariatric surgery, and decreased adverse events after bariatric surgery. In an exemplary embodiment, the one or more predicted outcomes provided by the outcome prediction module 204 indicate predicted outcomes for at least one weight-based factor. Non-limiting examples of weight-based factors include parameterization factors such as weight loss (e.g., pounds lost), target weight (e.g., patient weight in pounds), percent excess weight loss, percent weight change, and percent change in BMI, operationalization factors such as continuous and at various cutoff ranges up to 100% (e.g., achieving 50% weight lost), and time point factors such as time post-surgery (e.g., 1 month, 3 months, 6 months, 9 months, 12 months, 18 months, 24 months, 36 months, 48 months, 60 months, 72 months, 84 months, 96 months, 108 months, 120 months, etc.) and nadir weight. "Nadir weight" as used herein is defined as the lowest weight achieved after at least ten months of surgery without coexisting debilitating illness or use of weight lowering medications. Predicted outcomes for non-weight loss factors, such as predicted outcomes of bariatric surgery on comorbidities, procedure monetary cost (total and/or co-payment), follow-up cost (e.g., gastric band adjustments, etc.), insurance reimbursement, and risks (e.g., intraoperative, perioperative, long term, etc.) and types of complications associated with bariatric surgery, can be provided similarly with parameterization factors, operationalization factors, and/or time point factors, e.g., predicted outcomes for comorbidities as a percent remission or reduction post-surgery, predicted outcomes for comorbidities at each of one or more time points, etc.

As mentioned above, the user of the system 10 can be the patient, a medical practitioner treating the patient, or another user, such as a family member of the patient, a medical student, etc. The outcome prediction module 204 can thus provide information to a variety of people for a variety of different purposes. For non-limiting example, the outcome prediction module 204 can allow a patient to self-evaluate different bariatric surgical procedures, which can help educate the patient about real-world consequences of different bariatric surgical procedures. The patient can therefore ask medical practitioners more informed questions and/or can have more realistic expectations of outcomes of bariatric surgery. The outcome prediction module 204 can allow a patient to evaluate an actual outcome of a bariatric surgical procedure performed on the patient by inputting "before" patient data to the system 10. The patient can then compare the predicted outcome(s) of the bariatric surgery provided by the outcome prediction module 204 with actual results of the patient's bariatric surgery. The patient can thus evaluate whether weight loss and/or other target results are being achieved, which can help the patient modify their post-surgery treatment plan and/or consult their medical practitioner for help in modifying their post-surgery treatment plan, and/or which can help manage the patient's expectations regarding the surgery's outcome. Weight is not always quickly lost after bariatric surgery, but the surgery can nevertheless be an effective treatment for obesity by gradually causing weight loss after the surgery. However, if weight is not quickly lost following bariatric surgery, a patient can sometimes become discouraged and stop following their post-surgery treatment plan as planned by a medical practitioner, which can prevent the patient from realizing a best outcome of the surgery. Thus, the outcome prediction module 204 can help manage patient expectations following surgery and, thus, help the patient lose weight. For another non-limiting example, the outcome prediction module 204 can allow a medical practitioner to evaluate an actual outcome of a bariatric surgical procedure performed on a patient by inputting "before" patient data to the system 10. The medical practitioner can then compare the predicted outcome(s) of the bariatric surgery provided by the outcome prediction module 204 with actual results of the patient's bariatric surgery. The medical practitioner can thus evaluate whether weight loss and/or other target results are being achieved, which can help the medical practitioner determine whether to modify the patient's post-surgery treatment plan to achieve different weight loss results.

The outcome prediction module 204 can be configured to read information from and/or write information to any one or more of the databases 300, 302, 304, 306, 308. In an exemplary embodiment, the outcome prediction module 204 can be configured to write information to the patient data database 300, such as predicted outcome results for patients. In other words, the outcome prediction module 204 can be configured to store predicted outcome results in the system 10, thereby allowing a user to retrieve saved predicted outcome results for future consultation, e.g., to allow a patient and medical practitioner to discuss the predicted outcome results in person, to facilitate comparison of post-surgery results with pre-surgery predicted outcome results, to allow a user to modify some input patient data without having to re-enter data in all patient data input fields, etc.

The outcome prediction module 204 can be configured to generate predicted outcomes of bariatric surgery in a variety of ways. In an exemplary embodiment, the outcome prediction module 204 can be configured to input patient data regarding a patient entered via the patient data input module 200 and/or stored in the patient data database 300 to a model configured to compare the input patient data to arrive at one or more predicted outcomes for each of one or more different bariatric surgical procedures. The model can be based on historical data and include an equation with coefficients based on historical data, with the input patient data being plugged in as input variables in the equation. Development and use of models and equations is also discussed above. As will be appreciated by a person skilled in the art, a model can include any one or more of stratified univariate analysis, multivariable regression models, generalized linear models, and other data mining techniques on multiple data sets. Multivariable models can be based on a variety of variable selection techniques such as forward selection, stepwise selection, backward elimination, least angle regression, all-possible subsets, fully saturated, Bayesian, and any another advanced selection algorithm. Variable selection within these techniques can be based on a variety of statistical measures such as F-tests, the chi-square score statistic, residual mean square error (MSE), coefficient of multiple determination (R2), adjusted coefficient of multiple determination (AdjR2), Akaike's information criterion (AIC), Hannan and Quinn information criterion (HQ), Schwarz criterion (BIC), and Mallow's Cp. In another exemplary embodiment, the outcome prediction module 204 can be configured to input patient data regarding a patient entered via the patient data input module 200 and/or stored in the patient data database 300 and input historical data entered via the historical data input module 201 and/or stored in the historical data database 302 to a model configured to compare the input patient data and the input historical data to arrive at one or more predicted outcomes for each of one or more different bariatric surgical procedures. Inputting historical data can take more time and/or use more processing resources than using an equation based on historical data, but inputting historical data may allow for more recently gathered historical data to be considered in the analysis performed by the outcome prediction module 204.

The web interface configured to allow users to access the outcome prediction module 204 can have a variety of configurations. The web interface providing one or more predicted outcomes can include a graphical display (e.g., image(s) and, optionally, text). The web interface can, however, provide one or more predicted outcomes as a text-only display. In an exemplary embodiment, the predicted outcome(s) can be displayed in one or more graphs, e.g., bar graphs, line graphs, pie graphs, etc., as graphs can typically be easily understood by non-medically trained users as well as by medically trained users.

The web interface providing one or more predicted outcomes can display predicted outcomes for each of a plurality of different types of bariatric surgery on a single web page, thereby facilitating comparison between the different types of bariatric surgery. Each of the predicted outcomes displayed on a single web page can be for a same predetermined time following bariatric surgery (post-surgery time), which can help differences and similarities in predicted outcomes for the different types of surgeries be readily identified.

The web interface providing one or more predicted outcomes can be the same web interface configured to allow input of patient data thereto, e.g., after a user submits patient data such as by clicking a "submit" button on a web interface, predicted outcomes can be displayed on the web interface. The user can thus be able to view a comprehensive collection of data, including the input patient data and the predicted outcomes. In some embodiments, a subset of the input patient data can be displayed on a same web interface as the predicted outcomes. The subset of the input patient data can include at least the patient's input weight and/or the patient's BMI. Being able to view the patient's input weight and/or BMI along with predicted outcomes of the patient's post-surgery weight and/or post-surgery BMI can help make viewing the predicted outcomes more meaningful. Alternatively, the web interface providing one or more predicted outcomes can be a separate web interface from the interface configured to allow input of patient data thereto, e.g., after a user submits patient data such as by clicking a "submit" button on a patient data web interface, a predicted outcomes web interface can be displayed. Providing less information on the web interface, e.g., displaying the predicted outcomes without displaying the input patient data, can help make the web interface less cluttered and thus easier for the user to view.

FIGS. 11-35 illustrate various embodiments of predicted outcome web interfaces configured to be displayed on a client terminal and to indicate one or more predicted outcomes of one or more different types of bariatric surgery. As mentioned above, the predicted outcome web interface can be displayed concurrently with input patient data, such as in a potential post surgery results area 526 of the patient data web interface 500 of FIG. 5. The post surgery results area 526 in the illustrated embodiment has a progress bar 528 therein. As will be appreciated by a person skilled in the art, the progress bar 528 can indicate an amount of outcome prediction analysis undertaken, e.g., the striped portion, and/or an amount remaining, e.g., the unstriped portion, and can be replaced by a predicted outcome web interface when the outcome prediction module 204 finishes the outcome prediction outcome analysis. As will be appreciated by a person skilled in the art, progress can be indicated in other ways, e.g., with a throbber, with a textual display of progress by percent, etc., or progress can not be indicated at all.

Figure 11:
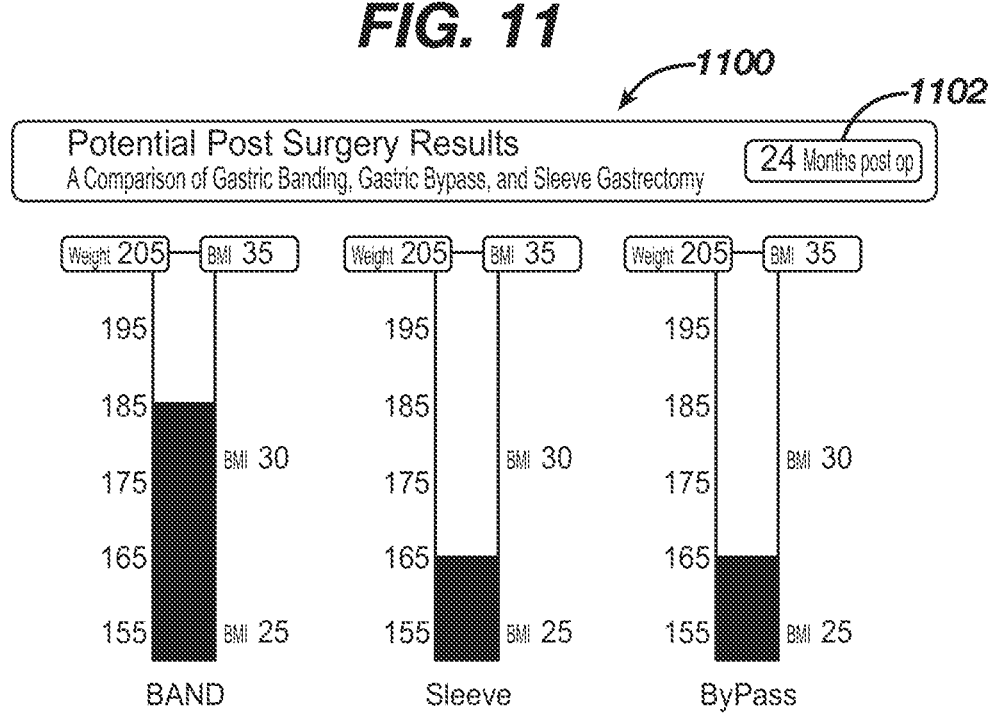
FIG. 11 is a schematic diagram of an embodiment of an outcome prediction portion of the patient data and predicted outcome web interface of FIG. 5.

A predicted outcome web interface 1100 of FIG. 11 illustrates predicted outcomes for a plurality of different types of bariatric surgery (gastric banding, sleeve gastrectomy, and gastric bypass), but as mentioned above, any web interface disclosed herein can display predicted outcomes for any number of different bariatric surgeries and any type of bariatric surgery. The number and types can be predetermined, as in the illustrated embodiment of FIGS. 5 and 8-11 in which gastric banding, sleeve gastrectomy, and gastric bypass are predetermined, or the number and types can be user-selected, such as in the embodiment of FIG. 6 including the surgical procedure data input area 604.

The predicted outcome web interface 1100 of FIG. 11 illustrates predicted outcomes at a user-selected time as entered in the post-surgery time field 518 and as shown in a time legend 1102, which in the illustrated embodiment is twenty-four months. However, as mentioned above, predicted outcomes can be determined and displayed for different time periods post-surgery and can be user-selected time periods or predetermined time periods.

The predicted outcome web interface 1100 of FIG. 11 displays predicted outcomes for weight-based factors including patient weight and patient BMI. Thus, for each of the different types of bariatric surgeries, the predicted outcome web interface 1100 indicates the patient's predicted weight and the patient's predicted BMI at the selected time period. In the illustrated embodiment, the patient's predicted weight and the patient's predicted BMI after 24 months are illustrated graphically as being no more than about 185 lbs. and no more than about 31 for gastric banding, no more than about 165 lbs. and no more than about 32 for sleeve gastrectomy, and no more than about 165 lbs. and no more than about 32 for gastric bypass. For ease of comparison, the patient's weight as entered in the weight field 504 and the patient's BMI as entered in the pre-surgery BMI field 516 are displayed on the predicted outcome web interface 1100 adjacent each predicted weight and BMI, respectively. The user can thus easily visually observe predicted changes in the patient's weight and BMI for each of the different surgical procedures.

Figure 12:
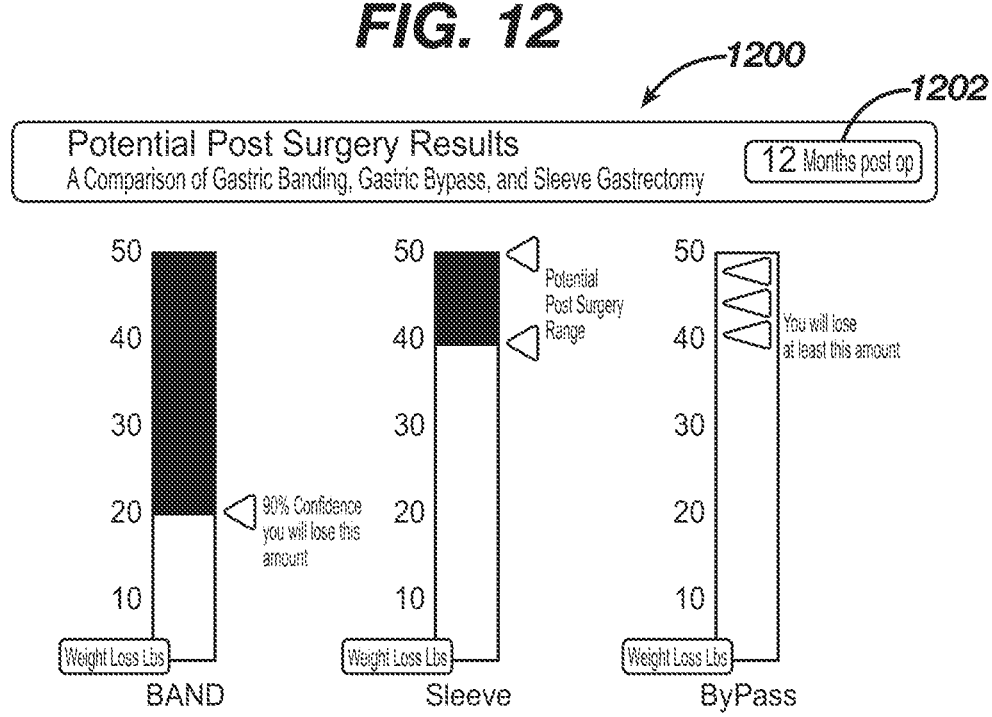
FIG. 12 is a schematic diagram of another embodiment of an outcome prediction portion of the patient data and predicted outcome web interface of FIG. 5.

A predicted outcome web interface 1200 of FIG. 12 illustrates predicted outcomes for a plurality of predetermined different types of bariatric surgery (gastric banding, sleeve gastrectomy, and gastric bypass). The predicted outcome web interface 1200 illustrates predicted outcomes at a user-selected time, e.g., as entered in the post-surgery time field 518 and as shown in a time legend 1202, which in the illustrated embodiment is twelve months.

The predicted outcome web interface 1200 displays predicted outcomes for a weight-based factor including patient weight. The predicted outcome web interface 1200 displays predicted patient weight in different formats than how predicted patient weight is displayed in the predicted outcome web interface 1100 of FIG. 11. In the predicted outcome web interface 1200 of FIG. 12, predicted weight loss for gastric banding is shown as a degree of confidence that the patient will lose at least "X" amount of weight, where the degree of confidence in the illustrated embodiment is 90% and where "X" in the illustrated embodiment is about 20 lbs, predicted weight loss for sleeve gastrectomy is shown as a predicted possible range of weight loss, where the predicted possible range in the illustrated embodiment is about 40-50 pounds, and predicted weight loss for gastric bypass is shown as a predicted minimum amount of weight loss, where the predicted minimum amount is about 40 pounds. Although predicted outcomes for the different types of surgeries are displayed in different ways on the predicted outcome web interface 1200, as for any of the predicted outcome web interfaces disclosed herein, predicted outcomes for different types of surgeries displayed on a same web interface can be displayed in any way, same or different from any of the other types of surgeries on the same web interface.

Figure 13:
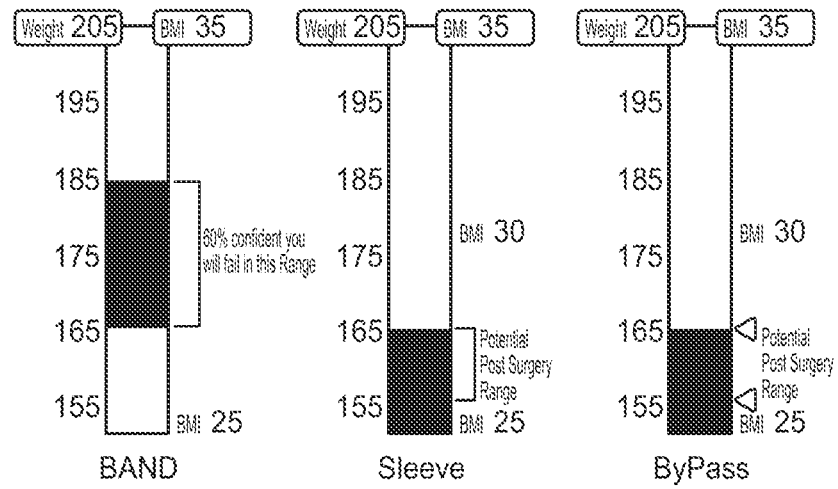
FIG. 13 is a schematic diagram of yet another embodiment of an outcome prediction portion of the patient data and predicted outcome web interface of FIG. 5.

A predicted outcome web interface 1300 of FIG. 13 illustrates predicted outcomes for a plurality of predetermined different types of bariatric surgery (gastric banding, sleeve gastrectomy, and gastric bypass). The predicted outcome web interface 1300 illustrates predicted outcomes at a user-selected time, e.g., as entered in the post-surgery time field 518 and as shown in a time legend 1302, which in the illustrated embodiment is twenty-four months.

The predicted outcome web interface 1300 displays predicted outcomes for weight-based factors including patient weight and patient BMI. The predicted outcome web interface 1300 displays predicted patient weight in a different format than patient weight is displayed in the predicted outcome web interfaces 1100, 1200 of FIGS. 11 and 12. In the predicted outcome web interface 1300 of FIG. 13, predicted weight loss and predicted BMI for each of the different types of surgical procedures is shown, respectively, as a predicted range of weight loss and as a predicted range of BMI. In the illustrated embodiment, the patient's predicted weight and the patient's predicted BMI after 24 months are illustrated graphically as being in a range of about 165-185 lbs. and in a range of about 27-31 for gastric banding, in a range of about 155-165 lbs. and in a range of about 26-27 for sleeve gastrectomy, and in a range of about 155-165 lbs. and in a range of about 26-27 for gastric bypass. Any of the ranges can be indicated as having a certain degree of confidence determined by the outcome prediction module 204, such as the predicted ranges for weight loss and BMI for gastric banding which are indicated in the illustrated embodiment as having a 60% confidence.

Figure 14:
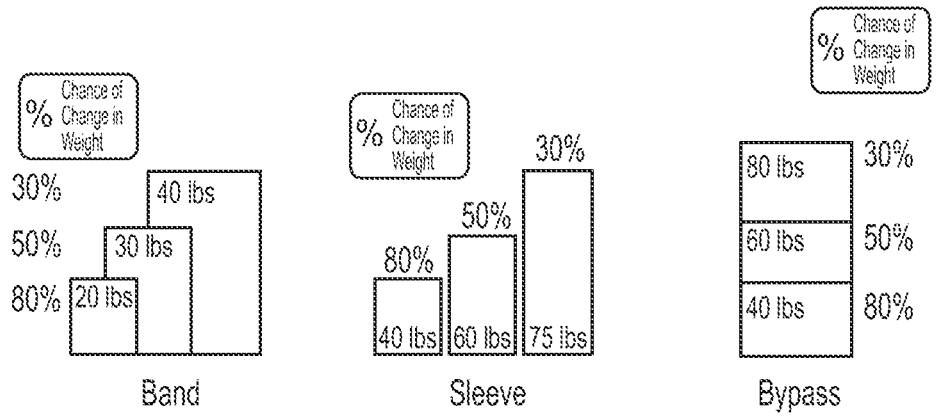
FIG. 14 is a schematic diagram of another embodiment of an outcome prediction portion of the patient data and predicted outcome web interface of FIG. 5.

A predicted outcome web interface 1400 of FIG. 14 illustrates predicted outcomes for a plurality of predetermined different types of bariatric surgery (gastric banding, sleeve gastrectomy, and gastric bypass). The predicted outcome web interface 1400 illustrates predicted outcomes at a user-selected time, e.g., as entered in the post-surgery time field 518 and as shown in a time legend 1402, which in the illustrated embodiment is twenty-four months.

The predicted outcome web interface 1400 displays predicted outcomes for a weight-based factor including patient weight. The predicted outcome web interface 1400 displays predicted patient weight in a different format than patient weight is displayed in the predicted outcome web interfaces 1100, 1200, 1300 of FIGS. 11-13. In the predicted outcome web interface 1400 of FIG. 14, multiple predicted weight losses are shown for each of the different types of surgical procedures, each predicted weight loss being associated with a certain degree of confidence determined by the outcome prediction module 204. In the illustrated embodiment, the patient's predicted weight after 24 months is illustrated graphically for gastric banding as being at least 20 lbs. with an 80% degree of confidence, at least 30 lbs. with a 50% degree of confidence, and at least 40 lbs. with a 30% degree of confidence; for sleeve gastrectomy as being at least 40 lbs. with an 80% degree of confidence, at least 60 lbs. with a 50% degree of confidence, and at least 75 lbs. with a 30% degree of confidence; and for gastric bypass as being at least 40 lbs. with an 80% degree of confidence, at least 60 lbs. with a 50% degree of confidence, and at least 80 lbs. with a 30% degree of confidence.

Figure 15:
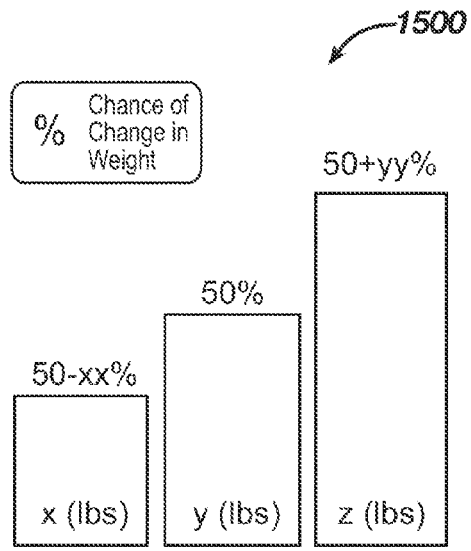
FIG. 15 is a schematic diagram of an embodiment of a predicted outcome web interface of the metabolic and bariatric surgery outcome predictive system of FIG. 2.

A predicted outcome web interface 1500 of FIG. 15 illustrates predicted outcomes for one type of bariatric surgery (which can be any type). The predicted outcome web interface 1500 displays predicted outcomes for a weight-based factor including patient weight loss. In the illustrated embodiment, the patient's predicted weight loss is illustrated graphically as being at least x lbs. with a 50%–xx % degree of confidence, at least y lbs. with a 50% degree of confidence, and at least z lbs. with a 50%+yy % degree of confidence. The weight values x, y, and z can be any values predicted by the outcome prediction module 204, with input patient data including at least the patient's weight. The values "xx %" and "yy %" can each be any percentage value less than 50% such that each confidence level is over 0% and less than 100%. In an exemplary embodiment, xx=yy. Weight loss or other weight-based factor could be display with a 0% confidence or with a 100% confidence, but such extreme confidence levels are typically rare in statistical analyses.

Figure 16:
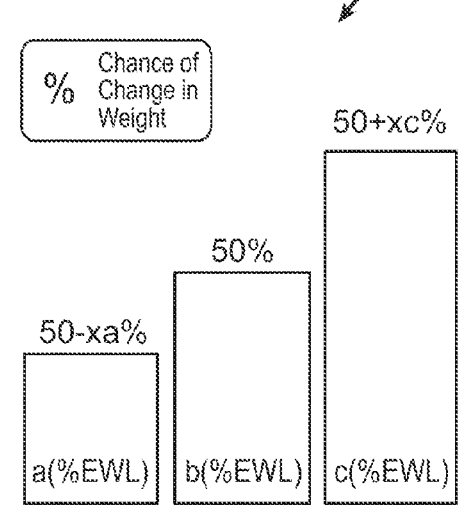
FIG. 16 is a schematic diagram of another embodiment of a predicted outcome web interface of the metabolic and bariatric surgery outcome predictive system of FIG. 2.

A predicted outcome web interface 1600 of FIG. 16 illustrates predicted outcomes for one type of bariatric surgery (which can be any type) similar to the interface 1500 of FIG. 15. However, the predicted outcome web interface 1600 of FIG. 16 displays predicted percentages of excess weight loss (EWL) for the patient post-surgery. As will be appreciated by a person skilled in the art, EWL is a traditional metric used to evaluate outcome of a bariatric surgical procedure. In the illustrated embodiment, the patient's predicted EWL percentage is illustrated graphically as being at least a with a 50%−xa % degree of confidence, at least b with a 50% degree of confidence, and at least c with a 50%+xc % degree of confidence. The EWL values a, b, and c can be any values predicted by the outcome prediction module 204, with input patient data including at least the patient's weight. The values "xa %" and "xc %" can each be any percentage value less than 50% such that each confidence level is over 0% and less than 100%. In an exemplary embodiment, xa=xc.

The embodiments of predicted outcome web interfaces illustrated in FIGS. 11-16 display predicted outcomes for weight-based factors. As mentioned above, web interfaces can additionally or alternatively display predicted outcomes for non-weight-based factors, e.g., bariatric surgery's effect on one or more comorbidities, risks and types of complications during and/or after bariatric surgery, bariatric surgery's effect on one or more medications, bariatric surgery's anticipated monetary cost, monetary cost savings, etc. Each of the comorbidities having a predicted outcome therefor can correspond to comorbidities identified by the patient data input module 200 as being associated with the patient, e.g., by being entered into a patient data web interface as a condition of the patient, by being stored in the patient data database 300 as being a condition of the patient, etc. In this way, only comorbidities relevant to the patient can be analyzed by the outcome prediction module 204 and displayed on the predicted outcome web interface, thereby helping to target information to the patient, helping to reduce the patient's confusion about surgery's effects, and/or reducing processing time of the outcome prediction module 204. Similarly, if the patient data web interface is configured to receive user selection of one or more types of bariatric surgery of interest to the patient, risks and types of complications during and/or after bariatric surgery can be analyzed by the outcome prediction module 204 and displayed on the predicted outcome web interface only for the user-selected type(s) of bariatric surgery. FIGS. 17-35 illustrate various embodiments of predicted outcome web interfaces displaying predicted outcomes for non-weight-based factors.

Figure 17:
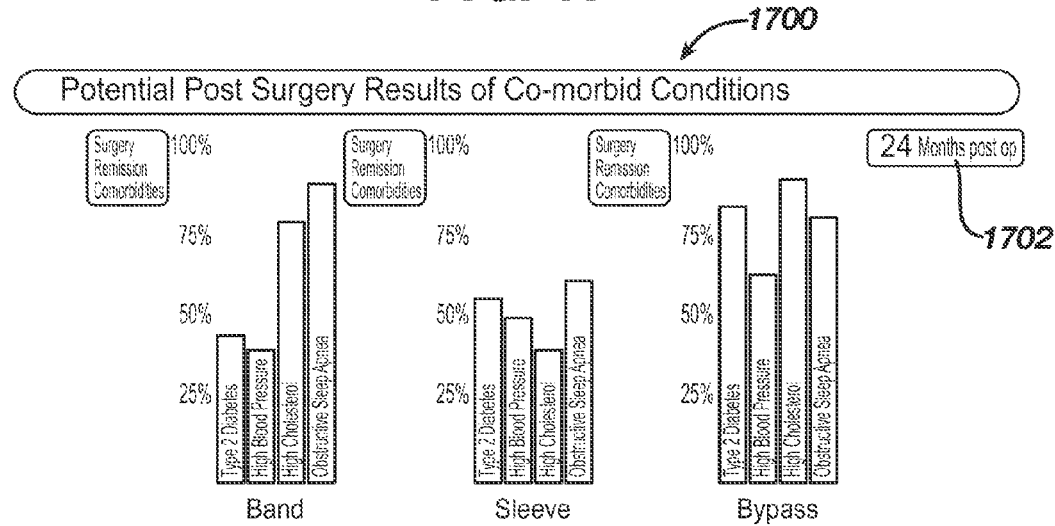
FIG. 17 is a schematic diagram of yet another embodiment of a predicted outcome web interface of the metabolic and bariatric surgery outcome predictive system of FIG. 2.

A predicted outcome web interface 1700 of FIG. 17 illustrates predicted outcomes for a plurality of different types of bariatric surgery (gastric banding, sleeve gastrectomy, and gastric bypass). The predicted outcome web interface 1700 of FIG. 17 illustrates predicted outcomes at a user-selected time as entered in the post-surgery time field 518 and as shown in a time legend 1702, which in the illustrated embodiment is twenty-four months. The predicted outcome web interface 1700 displays predicted outcomes for non-weight-based factors including potential post surgery results on one or more co-morbid conditions. Thus, for each of the different types of bariatric surgeries, the predicted outcome web interface 1700 indicates the patient's predicted remission post surgery for each of at least one comorbidity. In the illustrated embodiment, the patient's predicted comorbidity remissions after 24 months are illustrated graphically for gastric banding as being 47.0% for type 2 diabetes, 43.2% for high blood pressure, 78.5% for high cholesterol, and 91.8% for obstructive sleep apnea; for sleeve gastrectomy as being 56.0% for type 2 diabetes, 46.0% for high blood pressure, 43.2% for high cholesterol, and 60.0% for obstructive sleep apnea; and for gastric bypass as being 83.7% for type 2 diabetes, 67.5% for high blood pressure, 94.9% for high cholesterol, and 80.4% for obstructive sleep apnea.

Figure 18:
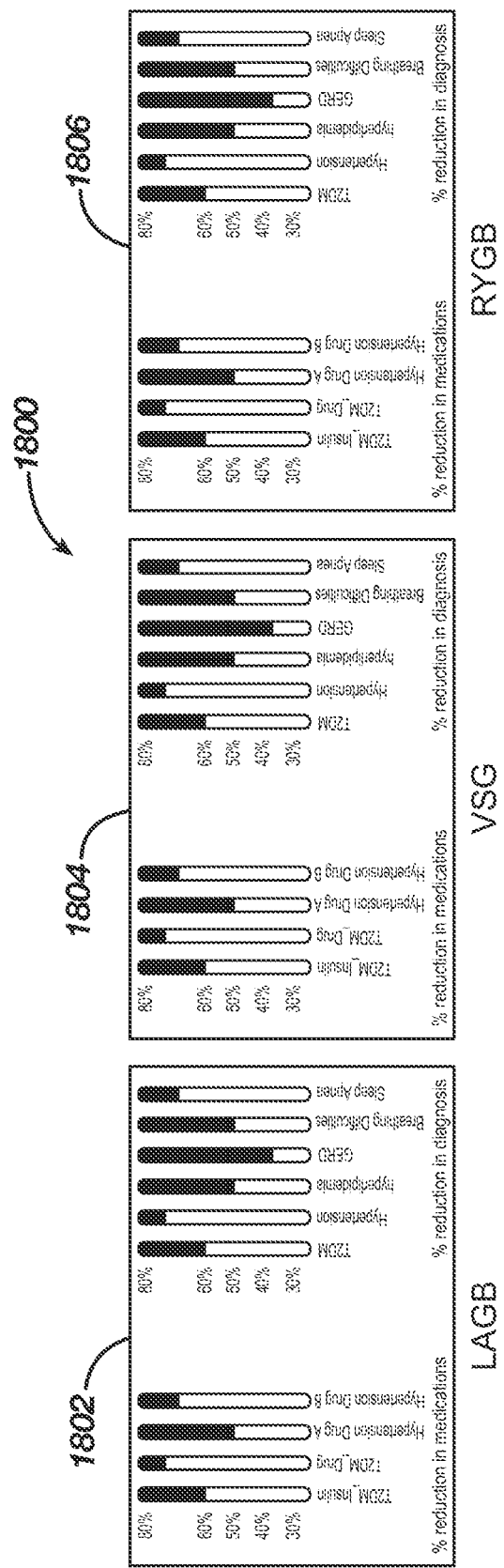
FIG. 18 is a schematic diagram of still another embodiment of a predicted outcome web interface of the metabolic and bariatric surgery outcome predictive system of FIG. 2.
Figure 19:
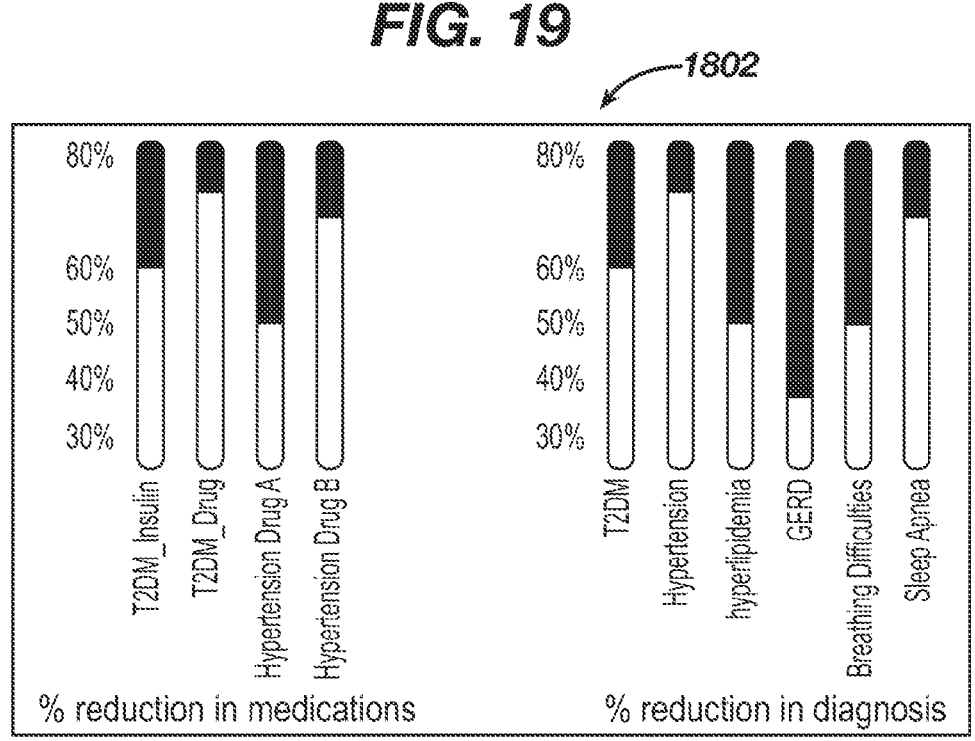
FIG. 19 is a schematic diagram of another embodiment of a predicted outcome web interface of the metabolic and bariatric surgery outcome predictive system of FIG. 2.

A predicted outcome web interface 1800 of FIG. 18 illustrates predicted outcomes for a plurality of different types of bariatric surgery (laparoscopic adjustable gastric banding (LAGB), vertical sleeve gastrectomy (VSG), and Roux en-Y gastric bypass (RYGB)). The predicted outcome web interface 1800 of FIG. 18 displays predicted outcomes for non-weight-based factors including potential post surgery reductions on one or more co-morbid conditions and potential post surgery results on one or more medications. In the illustrated embodiment, the patient's predicted reductions in comorbidities are illustrated graphically (on the right side of each surgery type's respective results area 1802, 1804, 1806) for each of LAGB, VSG, and RYGB as being about 60% for type 2 diabetes mellitus (T2DM), about 70% for hypertension, about 50% for hyperlipidemia, about 38% for gastroesophageal reflux disease (GERD), about 50% for breathing difficulties, and about 67% for sleep apnea. In the illustrated embodiment, the patient's predicted reductions in medications are illustrated graphically (on the left side of each surgery type's boxed-in area) for each of LAGB, VSG, and RYGB as being about 60% for T2DM insulin, about 70% for T2DM drug, about 50% for hypertension drug "A", and about 67% for hypertension drug "B." FIG. 19 illustrates a close-up view of the LAGB results area 1802.

Figure 20:
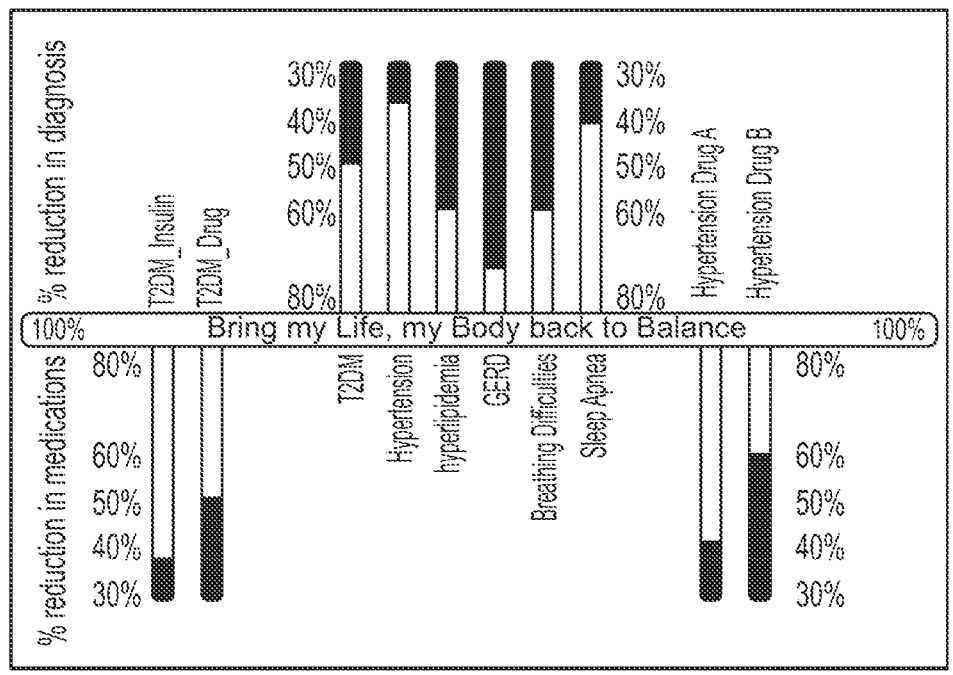
FIG. 20 is a schematic diagram of yet another embodiment of a predicted outcome web interface of the metabolic and bariatric surgery outcome predictive system of FIG. 2.

A predicted outcome web interface 2000 of FIG. 20 illustrates predicted outcomes for one type of bariatric surgery (can be any type). The predicted outcome web interface 2000 of FIG. 20 displays predicted outcomes for non-weight-based factors including potential post surgery reductions on one or more co-morbid conditions and potential post surgery results on one or more medications. In the illustrated embodiment, the patient's predicted reductions in comorbidities are illustrated graphically as being about 50% for T2DM, about 38% for hypertension, about 60% for hyperlipidemia, about 72% for GERD, about 60% for breathing difficulties, and about 40% for sleep apnea; and the patient's predicted reductions in medications are illustrated graphically as being about 40% for T2DM insulin, about 50% for T2DM drug, about 40% for hypertension drug "A", and about 60% for hypertension drug "B."

Figure 21:
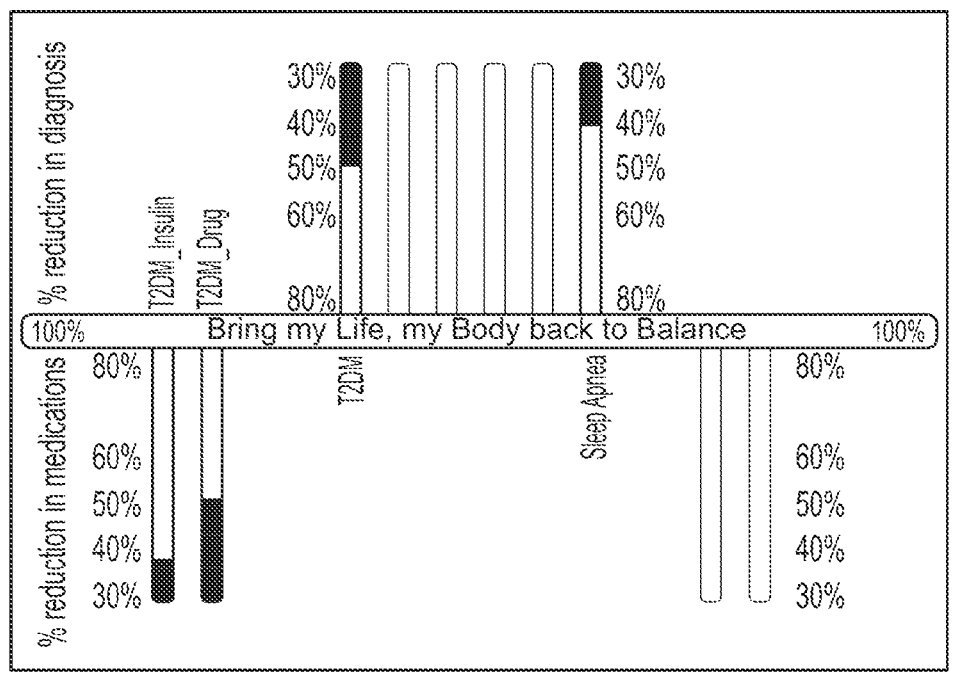
FIG. 21 is a schematic diagram of still another embodiment of a predicted outcome web interface of the bariatric surgery outcome predictive system of FIG. 2.
Figure 22:
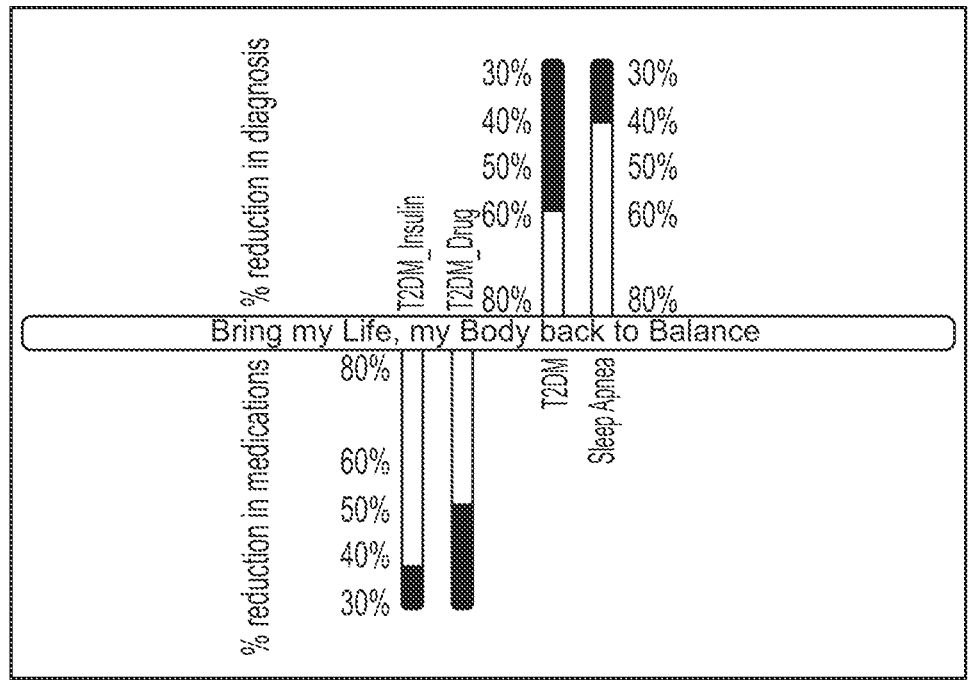
FIG. 22 is a schematic diagram of another embodiment of a predicted outcome web interface of the metabolic and bariatric surgery outcome predictive system of FIG. 2.

A predicted outcome web interface 2100 of FIG. 21 illustrates predicted outcomes for one type of bariatric surgery (can be any type) similar to the predicted outcome web interface 2000 of FIG. 20. The predicted outcome web interface 2100 of FIG. 21, however, greys out one or more comorbidities and/or one or more medications not relevant to the patient, e.g., not selected as being a condition of the patient via a patient data web interface. In the illustrated embodiment of FIG. 21, the patient's predicted reductions in comorbidities are illustrated graphically as being about 50% for T2DM and about 40% for sleep apnea; and the patient's predicted reductions in medications are illustrated graphically as being about 40% for T2DM insulin and about 50% for T2DM drug. Comorbidities hypertension, hyperlipidemia, GERD, and breathing difficulties are greyed out, and medications hypertension drug "A" and hypertension drug "B" are greyed out. As will be appreciated by a person skilled in the art, instead of greying out comorbidities, medications, and/or other factors (weight-based or non-weight-based) not relevant to the patient, a predicted outcome web interface can otherwise obscure them (e.g., blurring, strikethrough, etc.) or can not show those factor(s) at all. FIG. 22 illustrates a predicted outcome web interface 2200 similar to the web interface 2100 of FIG. 21 except that comorbidities and medications not relevant to the patient are not shown at all.

Figure 23:
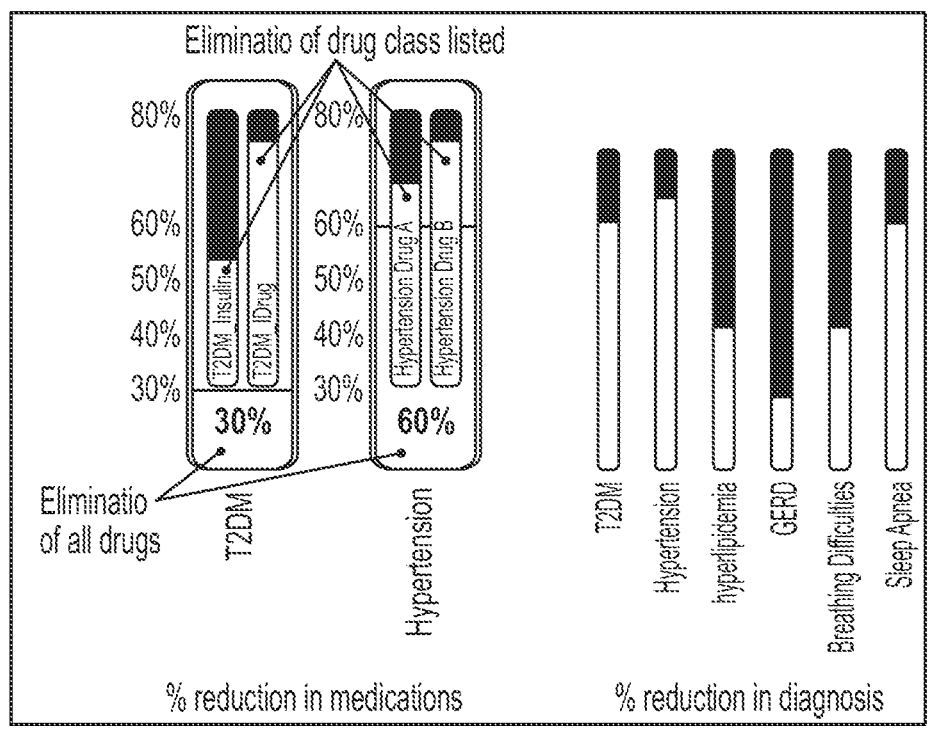
FIG. 23 is a schematic diagram of yet another embodiment of a predicted outcome web interface of the metabolic and bariatric surgery outcome predictive system of FIG. 2.

A predicted outcome web interface 2300 of FIG. 23 illustrates predicted outcomes for one type of bariatric surgery (can be any type). The predicted outcome web interface 2300 of FIG. 23 displays predicted outcomes for non-weight-based factors including potential post surgery reductions on one or more co-morbid conditions and potential post surgery results on one or more medications. In the illustrated embodiment, the patient's predicted reductions in comorbidities are illustrated graphically at the same amounts as in FIG. 20; and the patient's predicted reductions in medications are illustrated graphically as being about 53% for T2DM insulin, about 78% for T2DM drug, about 67% for hypertension drug "A", and about 75% for hypertension drug "B." A predicted outcome web interface can provide an overall prediction as to chances of medication being eliminated entirely post surgery for each ailment for which the patient is taking at least one medication. The predicted outcome web interface 2300 of FIG. 23 indicates a 30% chance that T2DM medications will be eliminated and a 60% chance that hypertension medications will be eliminated.

Figure 24:
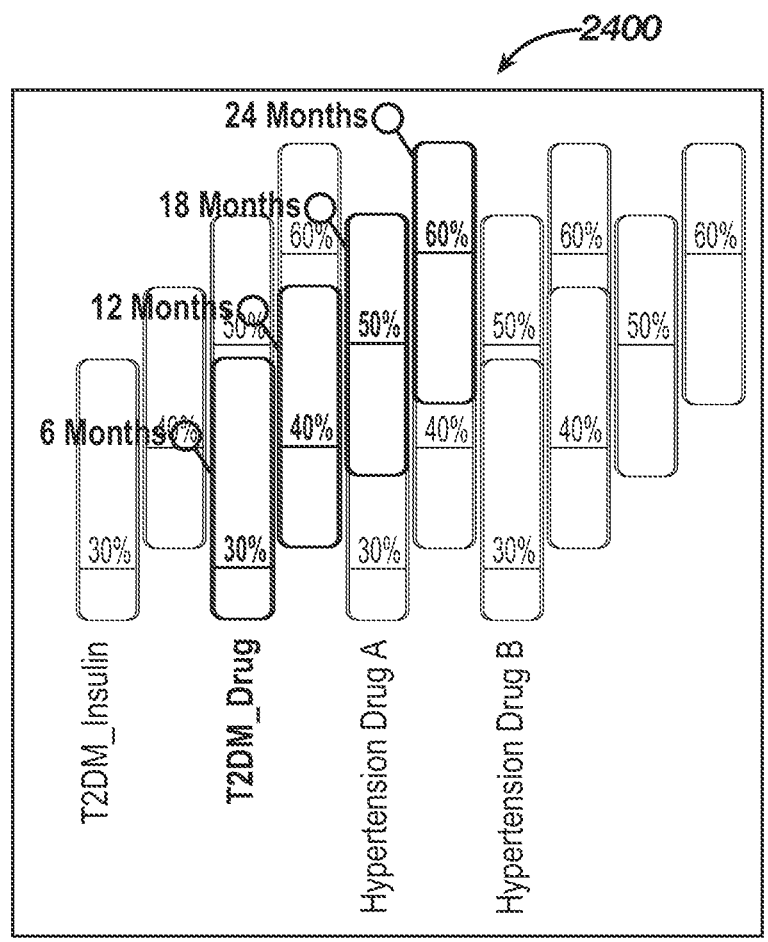
FIG. 24 is a schematic diagram of another embodiment of a predicted outcome web interface of the metabolic and bariatric surgery outcome predictive system of FIG. 2.

A predicted outcome web interface 2400 of FIG. 24 illustrates predicted outcomes for one type of bariatric surgery (can be any type). The predicted outcome web interface 2400 illustrates predicted outcomes at a plurality of times post-surgery. The plurality of times can be predetermined, or the times can be user-selected, e.g., entered in a post-surgery time field of a patient data web interface. Although four post-surgery times are shown in the illustrated embodiment, any number of post-surgery times can be shown. Similarly, although the post-surgery times in the illustrated embodiment are six months, twelve months, eighteen months, and twenty-four months, any post-surgery times can be displayed. The predicted outcome web interface 2400 of FIG. 24 displays predicted outcomes for a non-weight-based factor including potential post surgery results on one or more medications at each of the plurality of post-surgery times. In the illustrated embodiment, the patient's predicted reductions in medications for each of T2DM insulin, T2DM drug, hypertension drug "A," and hypertension drug "B" are illustrated graphically as being 30% after 6 months, 40% after 12 months, 50% after 18 months, and 60% after 24 months. When a pointer, e.g., a cursor, a stylus point, etc., on the predicted outcome web interface 2400 selects one of the medications, such as by hovering over one of the medications, the selected medication data can be made prominent to the user in one or more of color, contrast, transparency, etc. In the illustrated embodiment, T2DM is selected and is made prominent by greying out a remainder of the medications.

Figure 25:
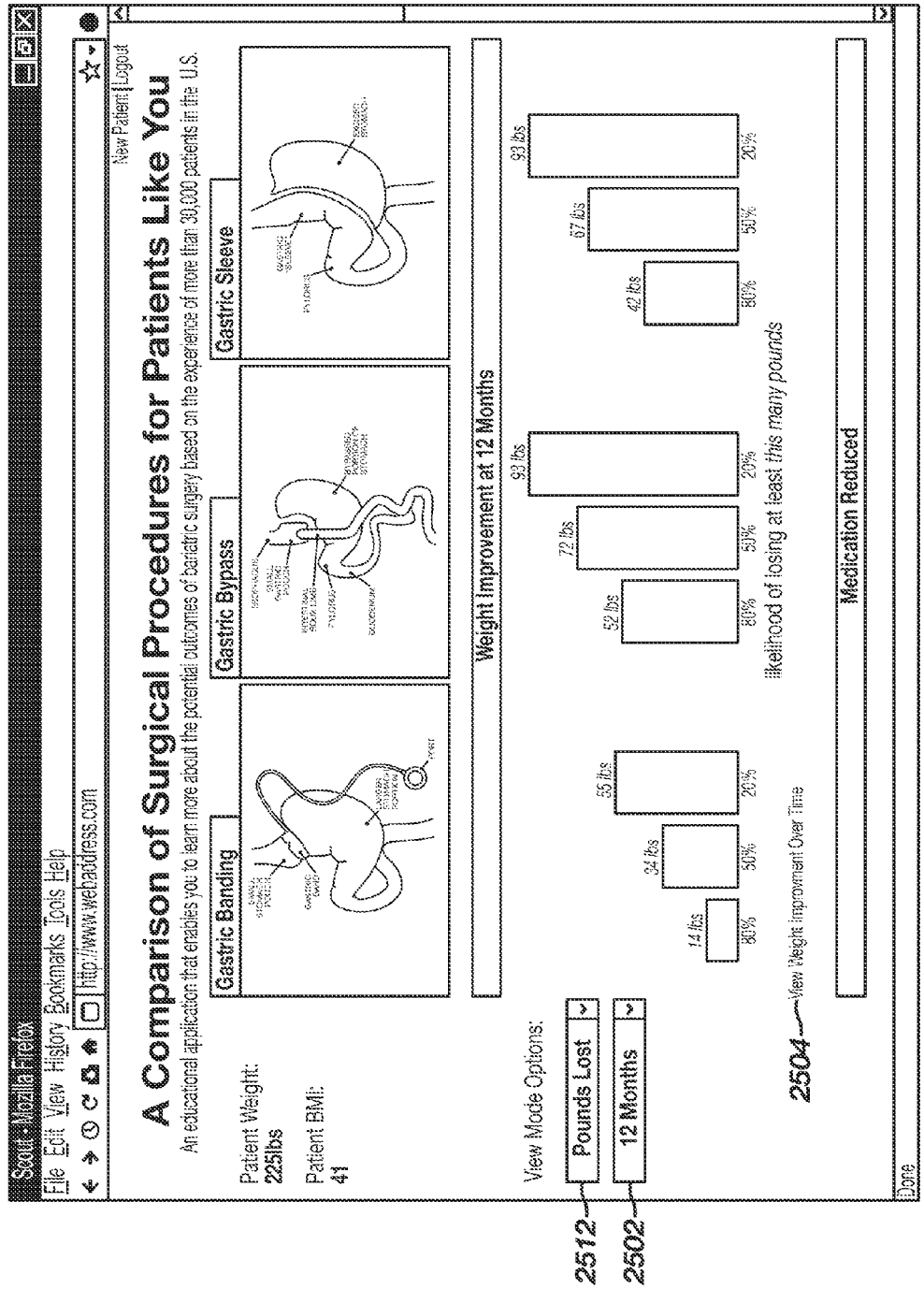
FIG. 25 is a schematic diagram of another embodiment of a patient data and predicted outcome web interface of the metabolic and bariatric surgery outcome predictive system of FIG. 2 for the first patient of FIG. 9.
Figure 26:
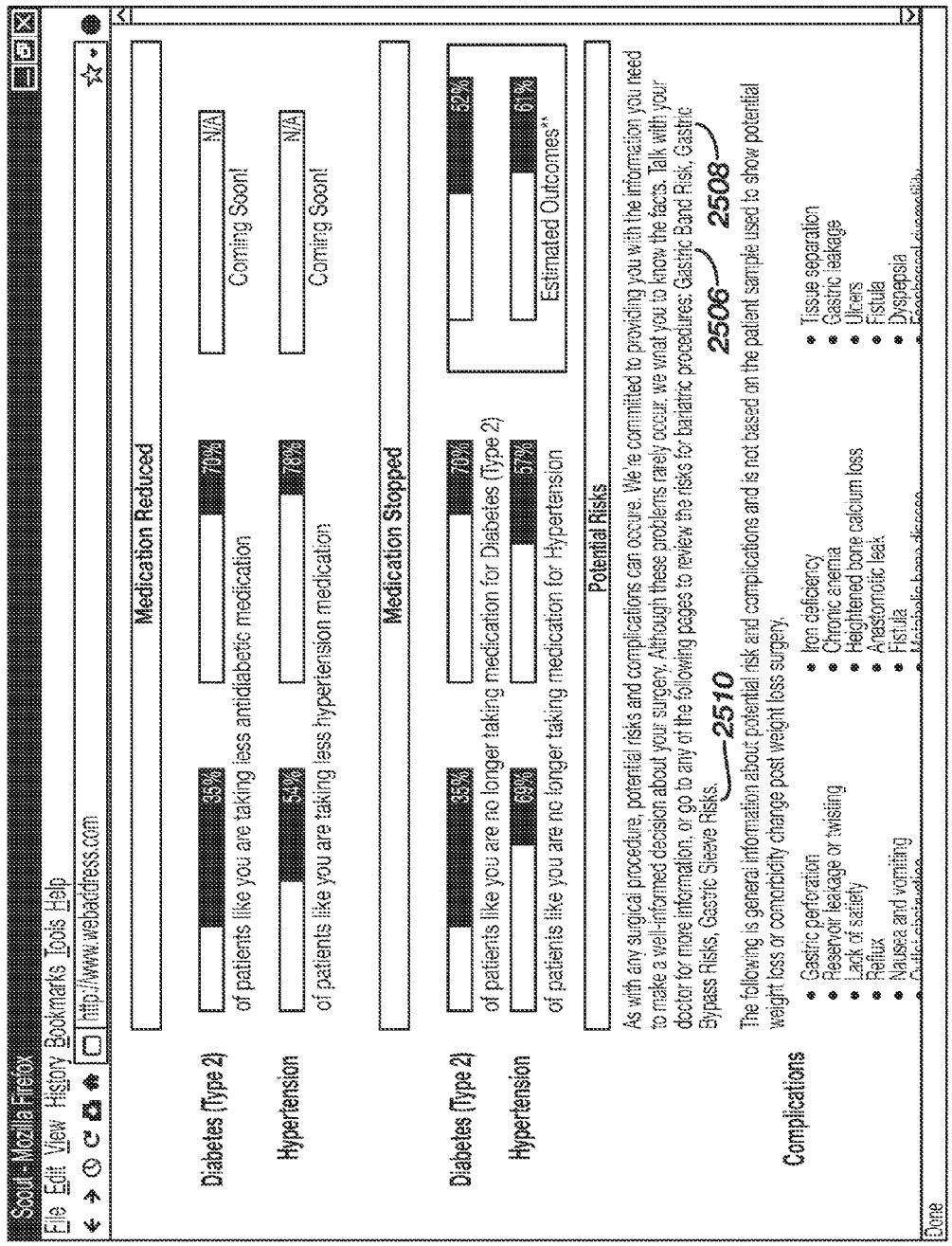
FIG. 26 is a continuation of the schematic diagram of FIG. 25.

A predicted outcome web interface 2500 of FIGS. 25-27 illustrates predicted outcomes for a plurality of different types of bariatric surgery (gastric banding, sleeve gastrectomy, and gastric bypass). FIG. 25 illustrates a top of the predicted outcome web interface 2500, FIG. 26 shows the predicted outcome web interface 2500 scrolled down from FIG. 25, and FIG. 27 shows the predicted outcome web interface 2500 scrolled down from FIG. 26.

The predicted outcome web interface 2500 of FIG. 25 shows predicted outcomes for the first patient of FIG. 9. In other words, the outcome prediction module 204 can determine the predicted outcomes shown in the predicted outcome web interface 2500 of FIG. 25 based on the patient data input for the first patient, as well as on historical data stored in the historical data database 302 determined by the outcome prediction module 204 to most closely correspond to the first patient. For non-limiting example, the outcome prediction module 204 can be configured to query the historical data stored in the historical data database 302 for data related to previously performed gastric banding, sleeve gastrectomy, and gastric bypass surgeries (or whatever bariatric surgery/surgeries are selected for analysis) on patients, at the time of their respective surgeries, having the same age as the first patient (or in an age range including the first patient's age), having the same gender as the first patient, having a same height as the first patient (or in a height range including the first patient's height), having a same weight as the first patient (or in a weight range including the first patient's weight), having the same race as the first patient, having the same ethnicity as the first patient, having the same current conditions as the first patient, and having the same current medications as the first patient. The outcome prediction module 204 can be configured to consider data for patients that are not an exact match with the first patient, e.g., patients not having the exact same age (or age range), gender, height (or height range), etc. as the first patient. Thus, the outcome prediction module 204 can be configured to account for situations in which no exact matches are found for the first patient in the historical data database 302 and can be configured to have a larger sample of data for analysis than if only exact patient data matches were considered in determining predicted outcomes.

A non-limiting example of a method to account for a situation where no exact match or matches is found is to create models and algorithms using one or more of the modeling techniques described above that model the correlations between one or more inputs and a desired output. In this way, a group of inputs can be collected as input into one or more models to calculate one or more outputs. The outputs can be displayed to the user in one or more of the ways described herein.

The predicted outcome web interface 2500 of FIG. 25 illustrates predicted outcomes at a user-selected time as entered in a post-surgery time field 2502, which in the illustrated embodiment is twelve months. The time in the post-surgery time field 2502 can be user-selected in any way, such as by drop-down menu as shown in FIGS. 25 and 28. The outcome prediction module 204 can be configured to determine predicted outcomes for each possible time period available for selection in the post-surgery time field 2502, which can allow predicted results to be quickly displayed on the predicted outcome web interface 2500 when the user selects one of the time periods. Alternatively, the outcome prediction module 204 can be configured to determine predicted outcomes for only the time period selected in the post-surgery time field 2502, which can allow for faster display of initial predicted results to the user. The outcome prediction module 204 can be configured to store, e.g., in the patient data database 200, determined predicted outcomes for a selected time, thereby allowing the outcome prediction module 204 to retrieve the stored results rather than recalculate the results, should the user switch between different time periods and re-select one or more previously selected time periods.

The predicted outcome web interface 2500 of FIG. 25 displays predicted outcomes for weight-based factors and for non-weight-based factors. The weight-based factor for which predicted outcomes are displayed in FIG. 25 includes weight lost, e.g., predicted amount of weight to be lost the selected amount of time (e.g., 12 months) after bariatric surgery. Confidence levels are also shown for each predicted weight loss. In the illustrated embodiment, the patient's predicted weight loss after twelve months is illustrated graphically for gastric banding as at least 14 lbs. at 80% confidence, at least 34 lbs. at 50% confidence, and at least 55 lbs. at 20% confidence; for sleeve gastrectomy as at least 52 lbs. at 80% confidence, at least 72 lbs. at 50% confidence, and at least 93 lbs. at 20% confidence; and for gastric bypass as at least 42 lbs. at 80% confidence, at least 67 lbs. at 50% confidence, and at least 93 lbs. at 20% confidence. Stated differently, the patient is predicted to have an 80% chance of losing at least 14 lbs., a 50% chance of losing at least 34 lbs., and a 20% chance of losing at least 55 lbs. with a gastric band twelve months after surgery; an 80% chance of losing at least 52 lbs., a 50% chance of losing at least 72 lbs., and a 20% chance of losing at least 93 lbs. with a vertical sleeve gastrectomy twelve months after surgery; and an 80% chance of losing at least 42 lbs., a 50% chance of losing at least 67 lbs., and a 20% chance of losing at least 93 lbs. with a gastric bypass twelve months after surgery.

Figure 29:
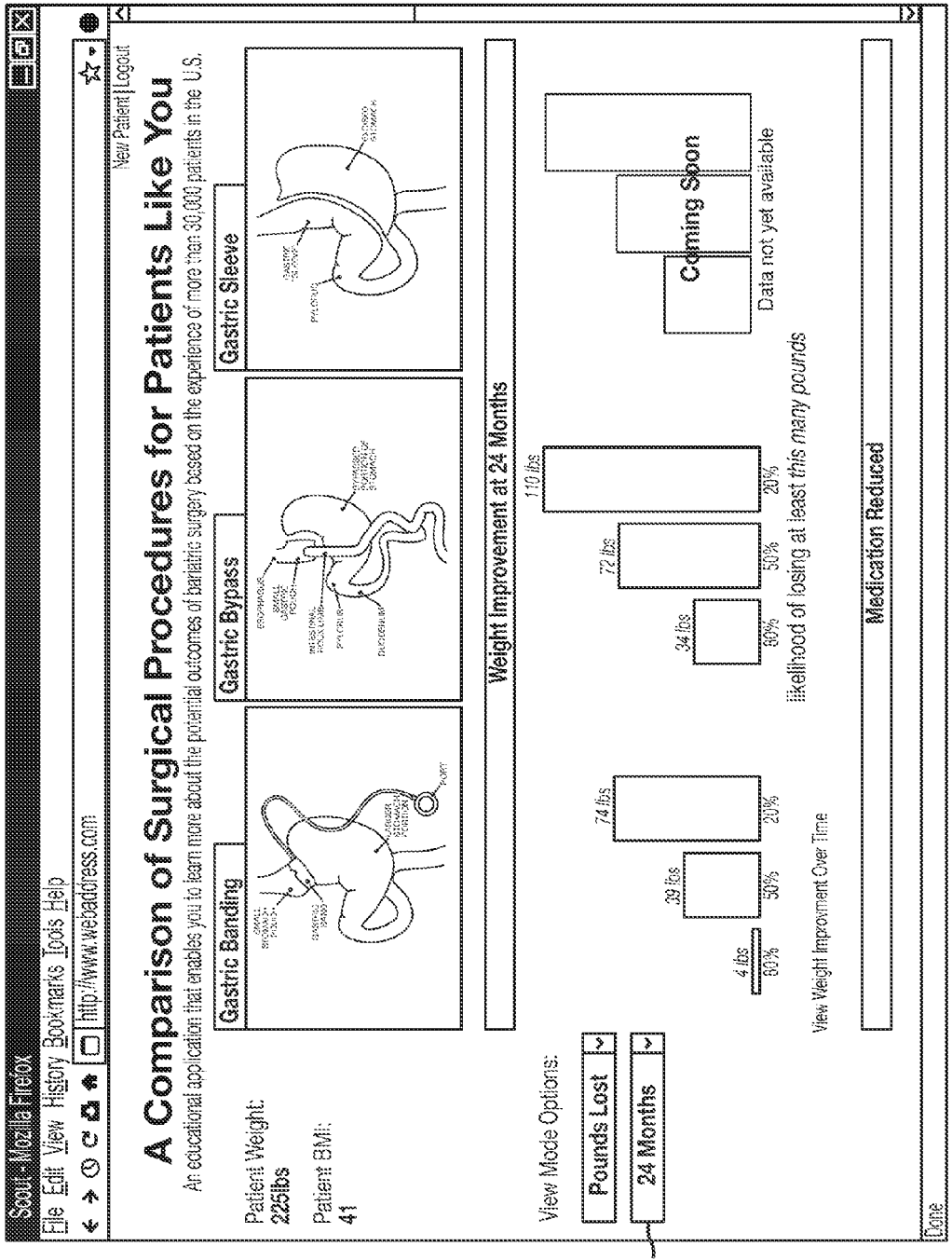
FIG. 29 is a schematic diagram of the patient data and predicted outcome web interface of FIG. 28 with the post-surgery time field being "24 months"

FIG. 29 illustrates a portion of a predicted outcome web interface 2500' displaying predicted outcomes for weight lost at a different selected post-surgery time, 24 months in this illustrated embodiment as shown in the post-surgery time field 2502. In the illustrated embodiment, the patient's predicted weight loss after 24 months is illustrated graphically for gastric banding as at least 4 lbs. at 80% confidence, at least 39 lbs. at 50% confidence, and at least 74 lbs. at 20% confidence; for sleeve gastrectomy as at least 34 lbs. at 80% confidence, at least 72 lbs. at 50% confidence, and at least 110 lbs. at 20% confidence; and for vertical sleeve gastrectomy as not being available. A predicted outcome may not be available if a threshold amount of historical data does not exist for the outcome prediction module 204 to analyze, e.g., if historical data is not available at all for a particular bariatric surgical procedure at a certain amount of time post-surgery, if historical data is not available for at least "X" number of previous surgeries performed on patients determined by the outcome prediction module 204 to correspond to the patient, if an algorithm that correlates patient inputs to patient outcomes is not sufficiently accurate or able to be validated, etc.

Figure 30:
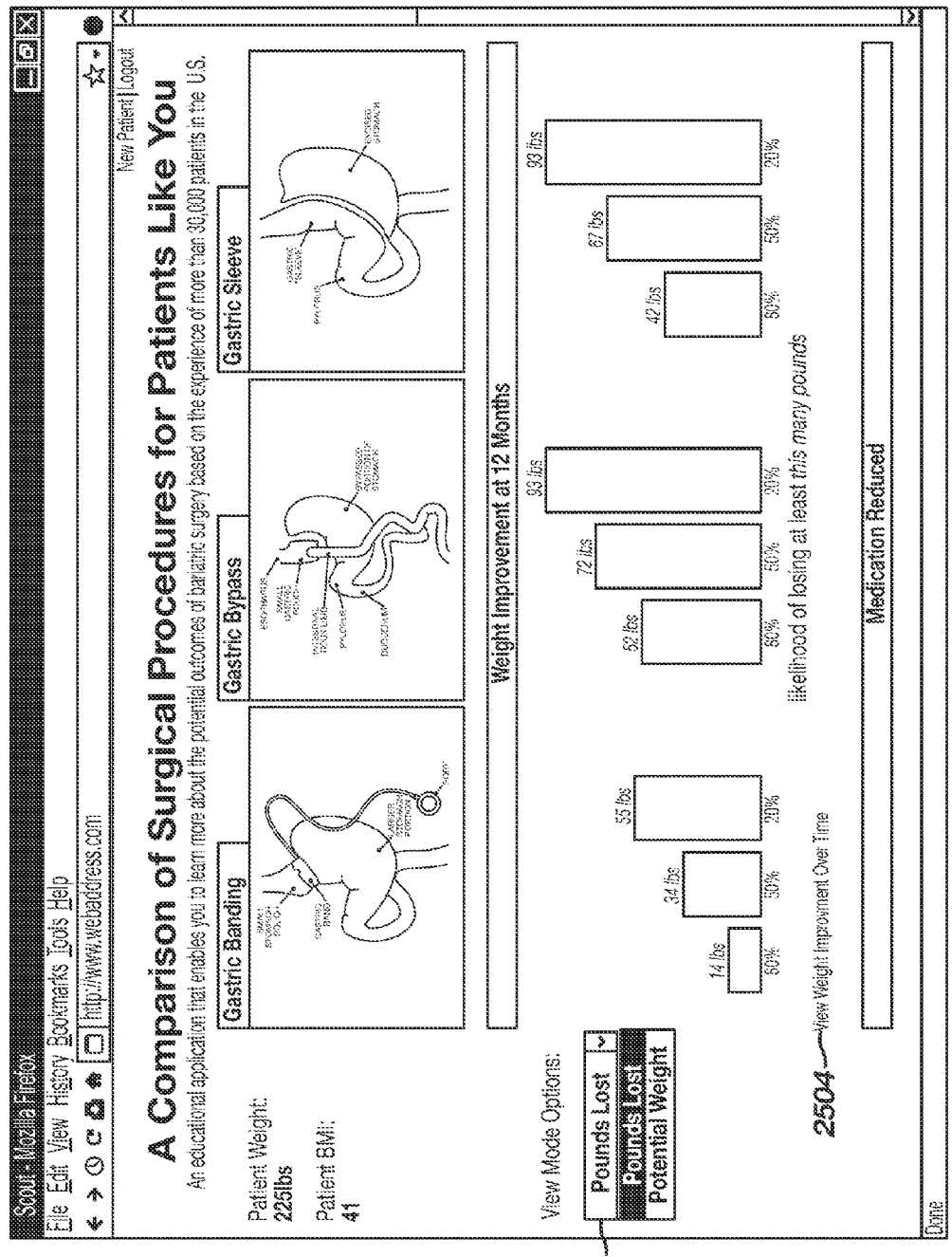
FIG. 30 is a schematic diagram of the patient data and predicted outcome web interface of FIG. 25 with weight factor field options being displayed.
Figure 31:
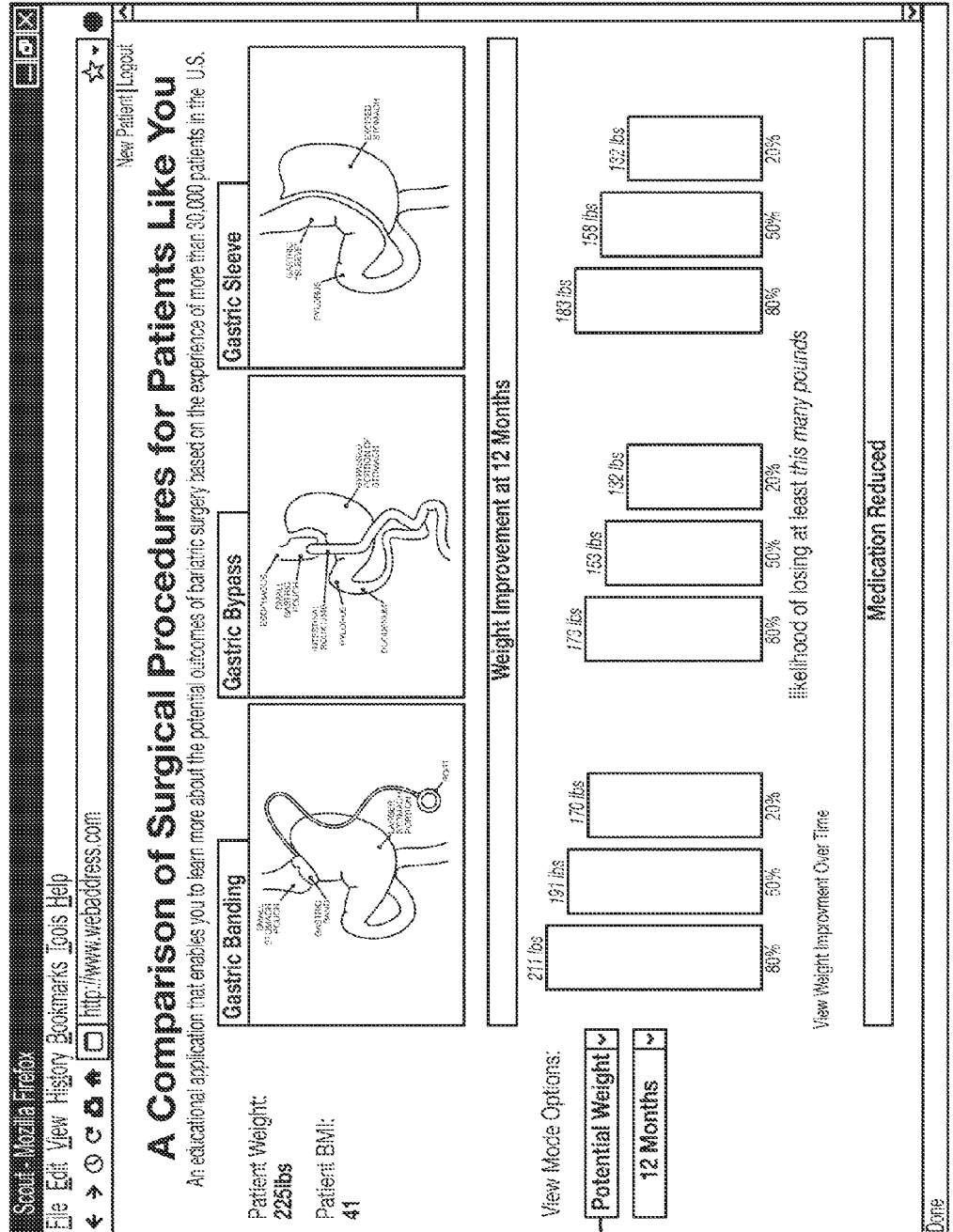
FIG. 31 is a schematic diagram of the patient data and predicted outcome web interface of FIG. 28 with the weight factor field being "potential weight"

As shown in FIGS. 25 and 30, the predicted outcome web interface 2500 can be configured to display predicted outcomes for at least one additional weight-based factor, e.g., weight improvement over time, potential weight, etc., such as by user-selection of a weight improvement link 2504 and/or by user-selection of a weight factor in a weight factor field 2512. The weight factors in the weight factor field 2512 can be user-selected in any way, such as by drop-down menu as shown in FIGS. 25 and 30. The weight factor field 2512 is selected as "Pounds Lost" in FIGS. 25-27, so the predicted outcome web interface 2500 displays predicted outcomes for weight lost as discussed above. The weight factor field 2512 is selected as "Potential Weight" in FIG. 31, so a predicted outcome web interface 2500" displays predicted outcomes for potential weight. Confidence levels are also shown for each predicted potential weight. In the illustrated embodiment, the patient's predicted potential weight after twelve months is illustrated graphically for gastric banding as not more than 211 lbs. at 80% confidence, not more than 191 lbs. at 50% confidence, and not more than 170 lbs. at 20% confidence; for gastric bypass as not more than 173 lbs. at 80% confidence, not more than 153 lbs. at 50% confidence, and not more than 132 lbs. at 20% confidence; and for sleeve gastrectomy as not more than 183 lbs. at 80% confidence, not more than 158 lbs. at 50% confidence, and not more than 132 lbs. at 20% confidence. Actual weight numbers are often used in setting post-surgery goals by patients, so displaying total weight instead of weight loss can help a user better understand how each of the procedures relates to the patient's post-surgery weight goals.

Referring again to the predicted outcome web interface 2500 of FIGS. 25-27, the non-weight based factors displayed on the predicted outcome web interface 2500 include potential post surgery reductions of one or more medications. As shown in FIG. 26, the patient's predicted medication reductions after 12 months are illustrated graphically for gastric banding as being 35% for type 2 diabetes and 54% for hypertension; for gastric bypass as being 70% for type 2 diabetes and 78% for hypertension; and for sleeve gastrectomy as not being available. The patient's predicted medication stoppage after 12 months are illustrated graphically for gastric banding as being 35% for type 2 diabetes and 34% for hypertension; for gastric bypass as being 70% for type 2 diabetes and 57% for hypertension; and for sleeve gastrectomy as being 52% for type 2 diabetes and 61% for hypertension. Any one or more predicted outcomes can be identified as being estimated based on one or more particular factors, such as the predicted medication stoppage for gastric bypass, which in the illustrated embodiment is identified as being estimated based on data collected from published literature.

As shown in FIGS. 26 and 27, the predicted outcome web interface 2500 also displays potential risks associated with each of gastric banding, vertical sleeve gastrectomy, and gastric bypass. The same types of modeling techniques can be used to calculate personalized predictions for each case.

As mentioned above, any outcome prediction web interface can be configured to allow user access to one or more educational materials stored in the educational information database 304. In the embodiment illustrated in FIG. 26, the predicted outcome web interface 2500 is configured to allow a user to select, e.g., click on, one or more of a gastric band risks link 2506, a gastric bypass risks link 2508, and a gastric sleeve risks link 2510 to learn more about various risks associated with the different procedures.

Figure 32:
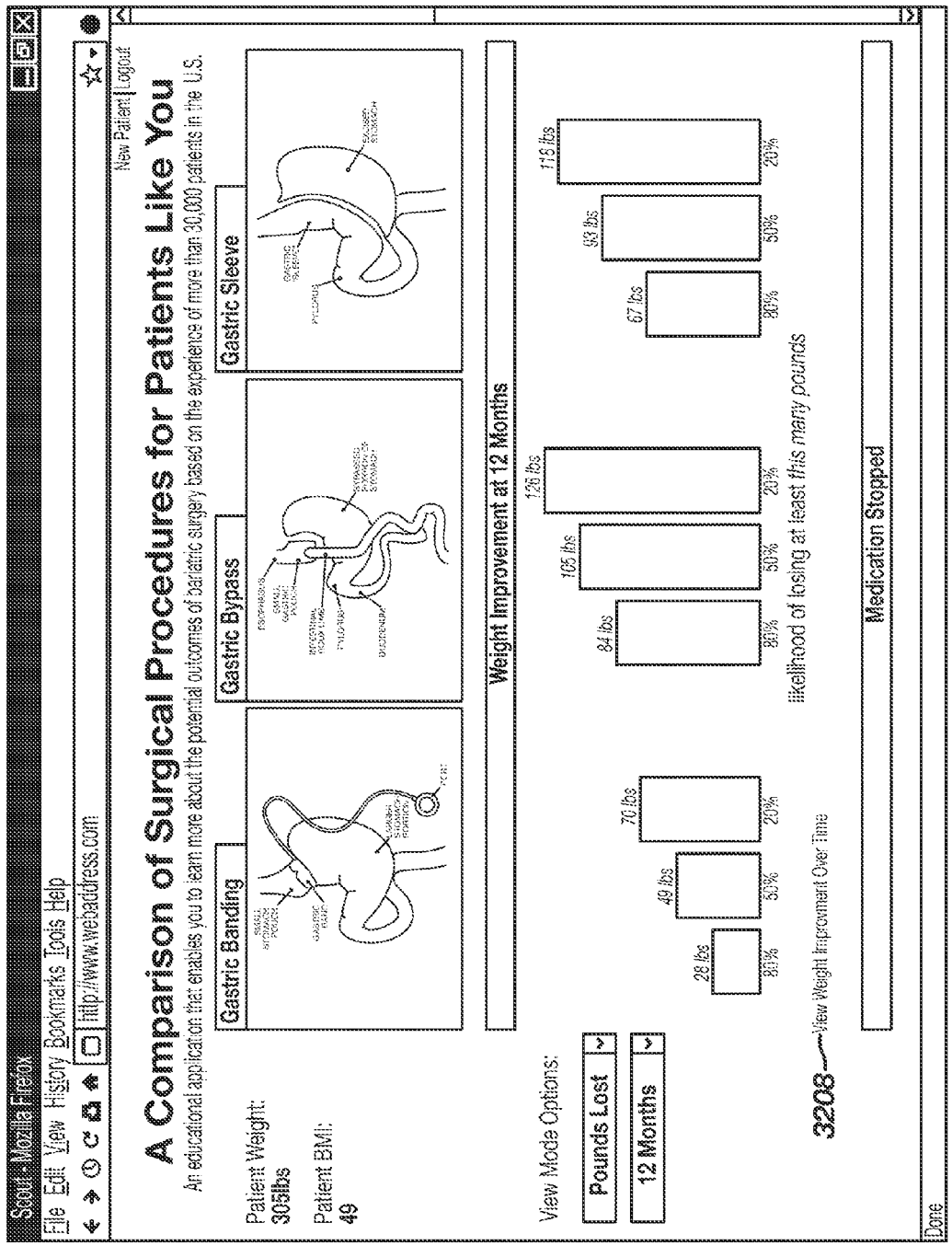
FIG. 32 is a schematic diagram of another embodiment of a patient data and predicted outcome web interface of the metabolic and bariatric surgery outcome predictive system of FIG. 2 for the second patient of FIG. 10.
Figure 33:
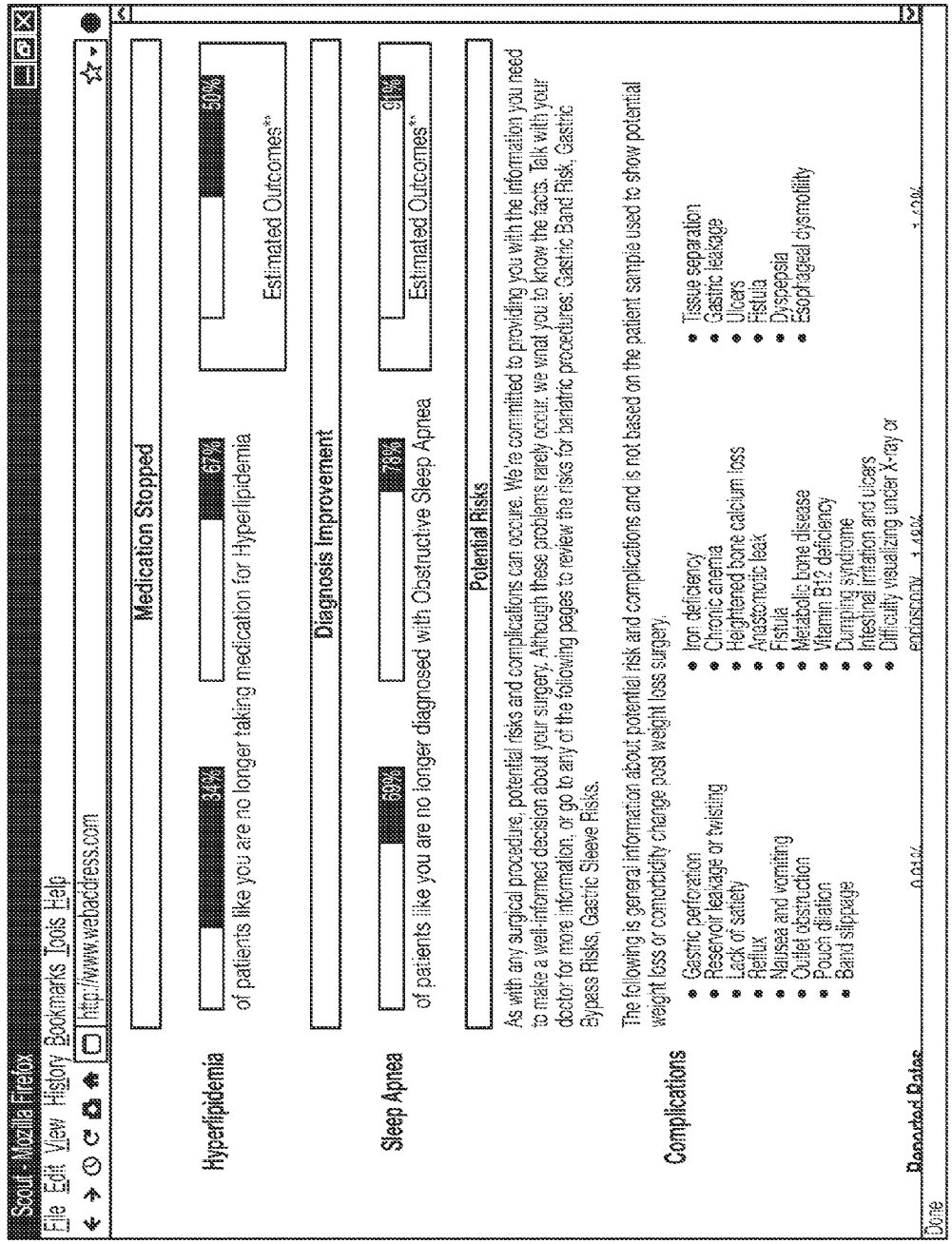
FIG. 33 is a continuation of the schematic diagram of FIG. 32.

A predicted outcome web interface 3200 of FIGS. 32-34 illustrates predicted outcomes for a plurality of different types of bariatric surgery (gastric banding, sleeve gastrectomy, and gastric bypass). FIG. 32 illustrates a top of the predicted outcome web interface 3200, FIG. 33 shows the predicted outcome web interface 3200 scrolled down from FIG. 32, and FIG. 34 shows the predicted outcome web interface 3200 scrolled down from FIG. 33. The predicted outcome web interface 3200 is similar to the predicted outcome web interface 2500 of FIGS. 25-27 except that the predicted outcome web interface 3200 of FIGS. 32-34 shows predicted outcomes for the second patient of FIG. 10. In the illustrated embodiment, the patient's predicted weight loss after twelve months is illustrated graphically for gastric banding as at least 28 lbs. at 80% confidence, at least 49 lbs. at 50% confidence, and at least 70 lbs. at 20% confidence; for gastric bypass as at least 84 lbs. at 80% confidence, at least 105 lbs. at 50% confidence, and at least 126 lbs. at 20% confidence; and for sleeve gastrectomy as at least 67 lbs. at 80% confidence, at least 93 lbs. at 50% confidence, and at least 118 lbs. at 20% confidence. As shown in FIG. 33, the patient's predicted medication reductions after 12 months are illustrated graphically for gastric banding as being 34% for hyperlipidemia; for gastric bypass as being 67% for hyperlipidemia; and for sleeve gastrectomy as being 50% for hyperlipidemia. As also shown in FIG. 33, the patient's predicted diagnosis improvements after 12 months are illustrated graphically for gastric banding as being 69% for sleep apnea; for gastric bypass as being 78% for sleep apnea; and for sleeve gastrectomy as being 91% for sleep apnea.

Figure 35:
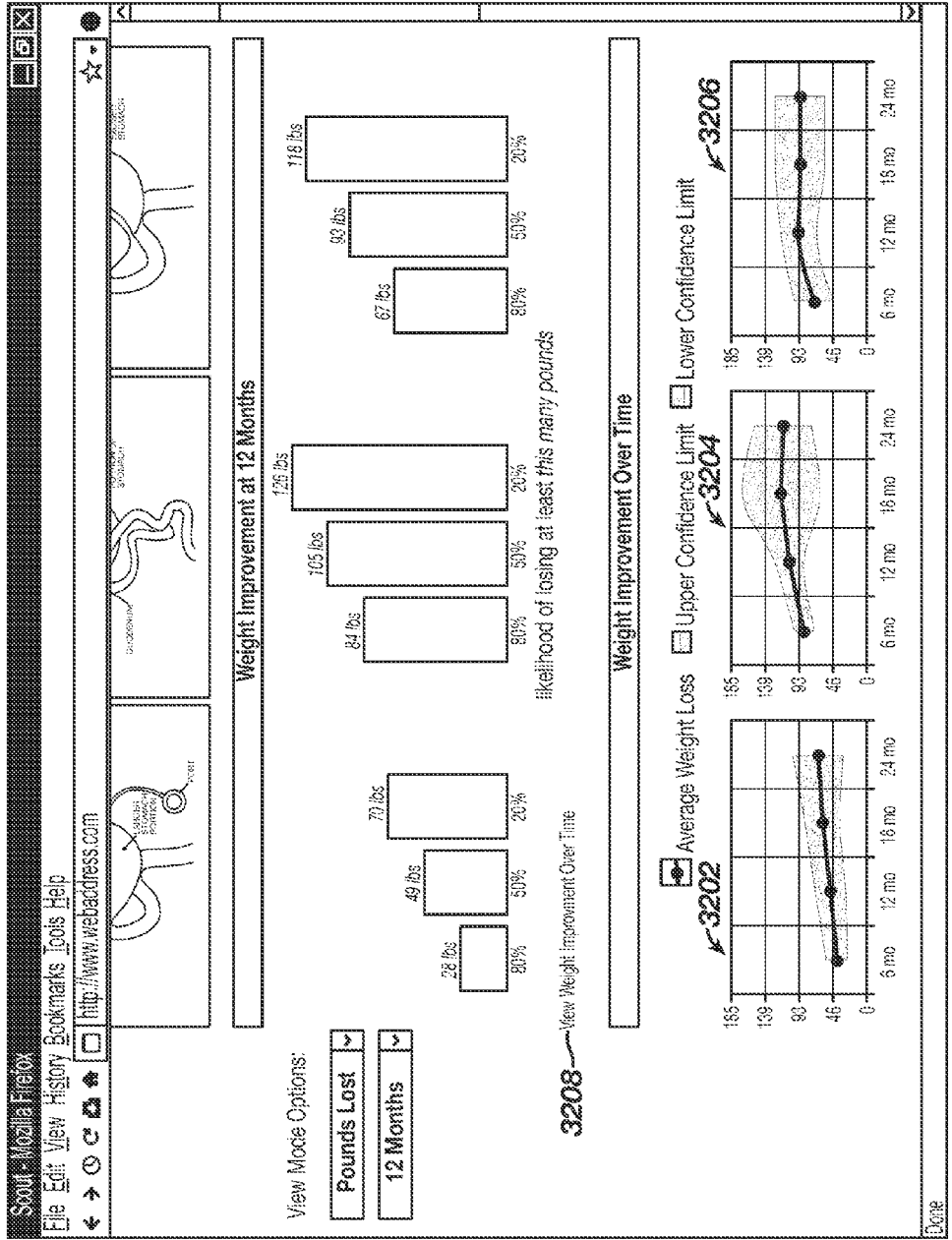
FIG. 35 is a schematic diagram of the patient data and predicted outcome web interface of FIG. 32 with weight improvement over time being displayed.

FIG. 35 illustrates predicted outcomes for an additional weight-based factor, weight improvement over time, for each of the bariatric procedures in respective graphs 3202, 3204, 3206. The additional weight-based factor can be displayed based on, e.g., user-selection of a weight improvement link 3208, and can be similarly hidden, e.g., subsequent user-selection of the weight improvement link 3208.

Medical Practitioner Locator Module

The medical practitioner locator module 206 can generally provide users of the system 10 with an interface for receiving notice of one or more medical practitioners having experience with one or more types of bariatric surgery. Determining who of many medical practitioners has experience in bariatric procedure(s) in which a patient is interested can be difficult for individuals to figure out without lengthy research. The medical practitioner locator module 206 can therefore help easily and quickly direct the user to medical practitioner(s) who may be able to provide examination, consultation, treatment, etc. for a patient. Additionally, a patient is typically interested in finding medical practitioner(s) who are geographically nearby. The medical practitioner locator module 206 can help the user identify nearby, experienced medical practitioner(s).

The medical practitioner locator module 206 can be configured to read information from and/or write information to any one or more of the databases 300, 302, 304, 306, 308. In an exemplary embodiment, the medical practitioner locator module 206 can be configured to read information from and/or write information to the medical practitioner database 306. In other words, the medical practitioner locator module 206 can be configured to store information regarding multiple medical practitioners in the medical practitioner database 306, thereby allowing identification of a subset of the medical practitioners that may be of assistance to a user of the system 10 by gathering information from the medical practitioner database 306.

Medical practitioner data can be organized in any way in the medical practitioner database 306 and/or in one or more other storage areas accessible by the system 10. The medical practitioner locator module 206 can be configured to automatically gather medical practitioner data and/or can be configured to receive manually input medical practitioner data, e.g., receive medical practitioner data submitted thereto. In an exemplary embodiment, the medical practitioner locator module 206 can be configured to automatically gather data. By automatically gathering medical practitioner data, the medical practitioner locator module 206 can help ensure that the most recent and comprehensive data is available, help ensure that only accredited or otherwise validated medical practitioners are included in the medical practitioner database 306, help account for accidental omission of manual medical practitioner data entry to the system 10, and/or help ensure that medical practitioner data is received by the system 10. The medical practitioner locator module 206 can, however, additionally or alternatively allow manual medical practitioner data entry, which can help allow data to be input and considered that is more current than data available in a storage unit automatically accessible by the medical practitioner locator module 206 and help allow input and consideration of data not accessible through automatic data gathering.

The medical practitioner locator module 206 can be configured to automatically gather medical practitioner data in a variety of ways and at a variety of times, similar to the automatic data gathering of the patient data input module 200 and the historical data input module 202 discussed above. The medical practitioner locator module 206 can be configured to receive medical practitioner data manually submitted thereto in a variety of ways, also similar to the manual data gathering of the patient data input module 200 and the historical data input module 202 discussed above.

The medical practitioner locator module 206 can be configured to receive a variety of different types of medical practitioner data regarding medical practitioners. Non-limiting examples of medical practitioner data that can be received (automatically and/or manually) by the medical practitioner locator module 206 include name, address, office hours, hospital affiliation, types of accepted insurance, types of bariatric surgical procedures previously performed, volume of bariatric surgical procedures previously performed, cost, years in practice, etc. Medical practitioners can sign up to be included in the medical practitioner database 306 and/or can be included as a result of a public search for medical practitioner information (Internet, etc.). The medical practitioners can be organized in the medical practitioners database 306 by, e.g., zip code.

The medical practitioner locator module 206 can be configured to identify medical practitioners for a user of the system 10 in a variety of ways. In an exemplary embodiment, the medical practitioner locator module 206 can be configured to receive as input a geographic location. The geographic location can be input automatically, e.g., by geographic location app on a mobile device, identification of an Internet Protocol (IP) address accessing the medical practitioner locator module 206, etc. Alternatively or additionally, the geographic location can be input manually, e.g., by user data entry onto a GUI, etc., such as in a geographic location field 706 on the patient data web interface 700 of FIG. 7. The geographic location field 706 can be configured to accept geographic location in any one or more formats, such as by zip code, state, city, street address, etc.

Based on the patient's geographic location, the medical practitioner locator module 206 can be configured to identify medical practitioners to the user of the system 10 by determining which, if any, medical practitioners stored in the medical practitioners database 306 are within a certain geographic area. As will be appreciated by a person skilled in the art, the geographic area can be defined in a variety of ways, such as within the input geographic location, within a certain number of miles, kilometers, etc. from the input geographic location, etc. If the medical practitioner locator module 206 does not identify any medical practitioners within the geographic area, the medical practitioner locator module 206 can be configured to provide alternate medical practitioners within an expanded geographic area near the input geographic location, e.g., expand the search area from within a ten mile radius to within a fifty mile radius. The alternate medical practitioners can be provided by default, or the user of the system 10 can be given an option for expanding the medical practitioners search.

In addition to considering the input geographic location, the medical practitioner locator module 206 can be configured to identify medical practitioners for the user of the system 10 based on one or more bariatric procedures the user has selected, e.g., via a patient data web interface, as being of particular interest to the user. The medical practitioners database 306 can thus determine which medical practitioners, if any, are within the geographic area and have experience in the selected bariatric procedure(s). If the medical practitioner locator module 206 does not identify any medical practitioners within the geographic area that have the selected procedure experience, the medical practitioner locator module 206 can be configured to provide alternate medical practitioners having the selected experience within an expanded geographic area near the input geographic location. The alternate medical practitioners can be provided by default, or the user of the system 10 can be given an option for expanding the medical practitioners search.

Figure 36:
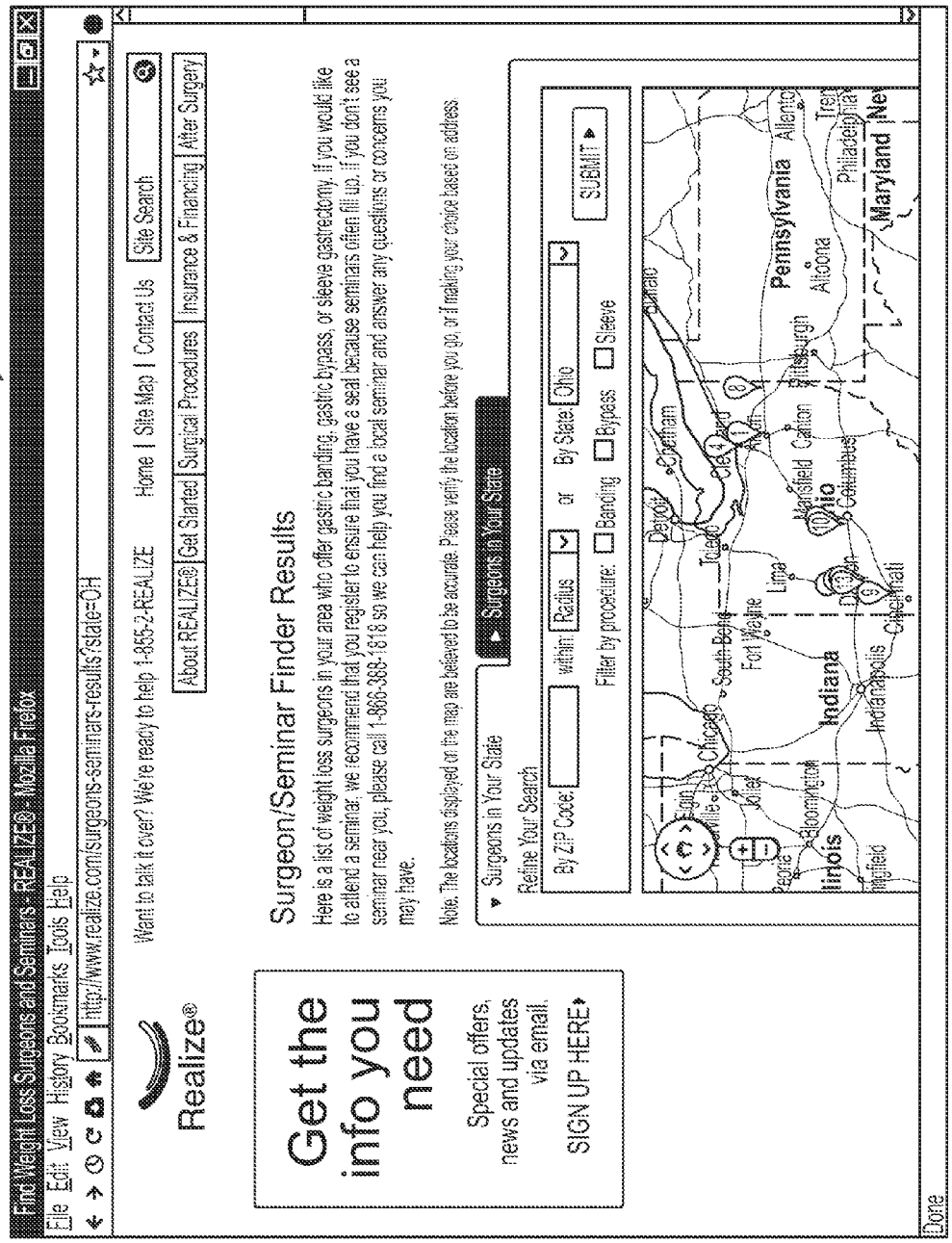
FIG. 36 is a schematic diagram of an embodiment of a medical practitioner web interface of the metabolic and bariatric surgery outcome predictive system of FIG. 2.
Figure 37:
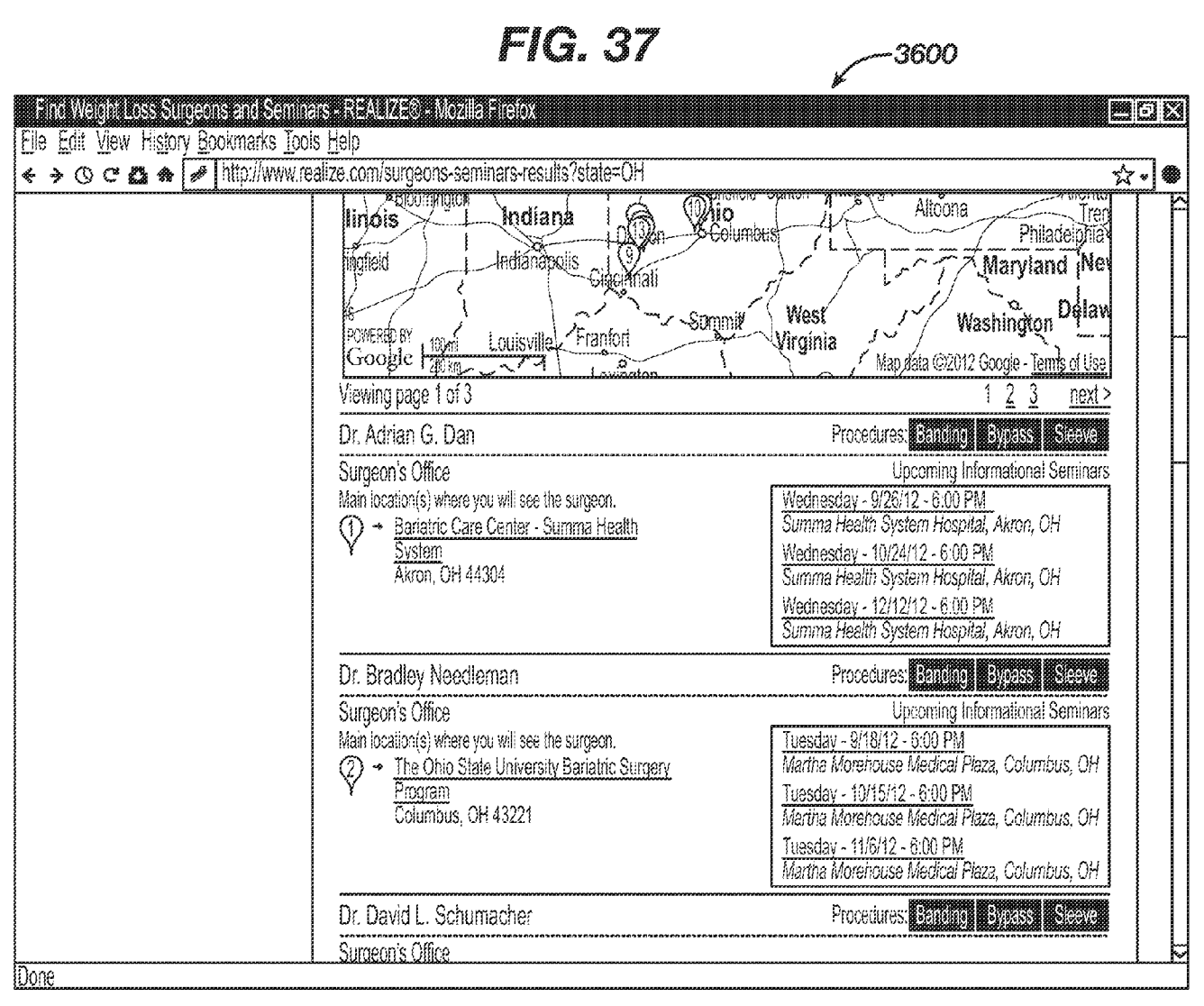
Figure 38:
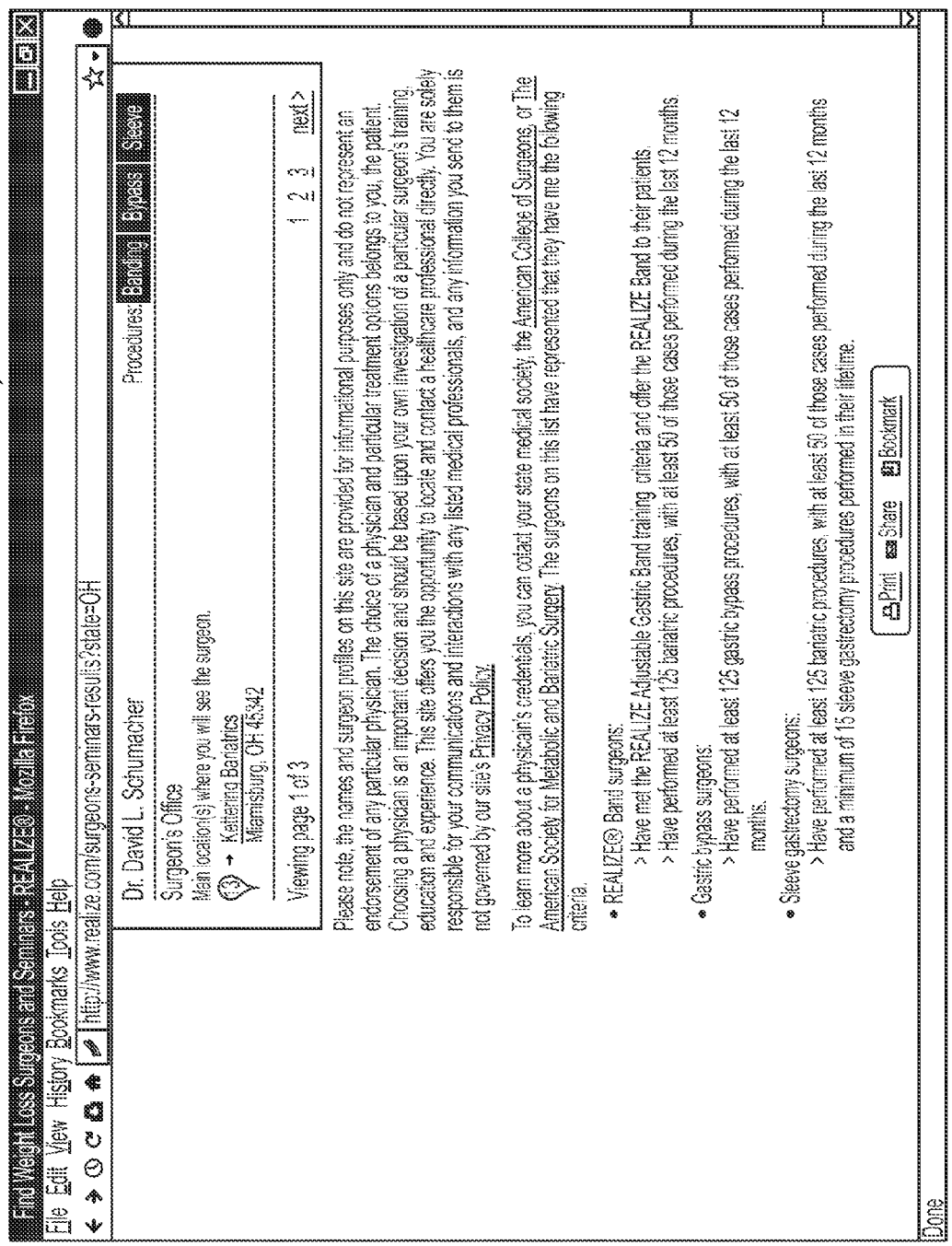
FIG. 38 is a continuation of the schematic diagram of FIG. 37.

FIGS. 36-38 illustrate one embodiment of a medical practitioner web interface 3600 configured to be displayed on a client terminal and to identify medical practitioners to a user of the system 10. FIGS. 36-38 display identified medical practitioners to a user as at <http://www.realize.com/> (accessed Sep. 19, 2012). FIG. 36 illustrates a top of the medical practitioner web interface 3600, FIG. 37 shows the medical practitioner web interface 3600 scrolled down from FIG. 36, and FIG. 38 shows the medical practitioner web interface 3600 scrolled down from FIG. 37. The medical practitioner web interface 3600 shows medical practitioners identified as being in the state of "Ohio" as entered in the geographic location field 706 on the patient data web interface 700 of FIG. 7.

Seminar Locator Module

The seminar locator module 208 can generally provide users of the system 10 with an interface for receiving notice of one or more seminars regarding bariatric surgery. Educational seminars regarding bariatric surgery are regularly scheduled in various geographic locations since bariatric surgery can be a complicated, daunting topic for untrained persons to become familiar with on their own and, sometimes, even with the assistance of their regular doctor, who may not have much or any experience with bariatric surgery. The seminar locator module 208 can help the user determine if any seminars are upcoming that the user may want to attend and/or may want to suggest to someone else to attend.

The seminar locator module 208 can be configured to read information from and/or write information to any one or more of the databases 300, 302, 304, 306, 308. In an exemplary embodiment, the seminar locator module 208 can be configured to read information from and/or write information to the seminar database 308. In other words, the seminar locator module 208 can be configured to store information regarding multiple seminars in the seminar database 308, thereby allowing identification of a subset of the seminars that may be of assistance to a user of the system 10 by gathering information from the seminar database 308.

Seminar data can be organized in any way in the seminar database 308 and/or in one or more other storage areas accessible by the system 10. The seminar locator module 208 can be configured to automatically gather seminar data and/or can be configured to receive manually input seminar data, e.g., receive seminar data submitted thereto. In an exemplary embodiment, the seminar locator module 208 can be configured to automatically gather data. By automatically gathering seminar data, the seminar locator module 208 can help ensure that the most recent and comprehensive data is available, help ensure that only accredited or otherwise validated seminars are included in the seminar database 308, help account for accidental omission of manual seminar data entry to the system 10, and/or help ensure that seminar data is received by the system 10. The seminar locator module 208 can, however, additionally or alternatively allow manual seminar data entry, which can help allow data to be input and considered that is more current than data available in a storage unit automatically accessible by the seminar locator module 208 and help allow input and consideration of data not accessible through automatic data gathering.

The seminar locator module 208 can be configured to automatically gather seminar data in a variety of ways and at a variety of times, similar to the automatic data gathering of the patient data input module 200 and the historical data input module 202 discussed above. The seminar locator module 208 can be configured to receive seminar data manually submitted thereto in a variety of ways, also similar to the manual data gathering of the patient data input module 200 and the historical data input module 202 discussed above.

The seminar locator module 208 can be configured to receive a variety of different types of seminar data regarding seminars. Non-limiting examples of seminar data that can be received (automatically and/or manually) by the seminar locator module 208 include date, time, name/title, address, types of bariatric surgical procedures planned for discussion at the seminar, cost, etc. Seminar organizers, officials, attendees, etc. can sign seminars up to be included in the seminar database 308 and/or can be included as a result of a public search for seminar information (Internet, etc.). The seminars can be organized in the seminar database 308 by, e.g., zip code.

The seminar locator module 208 can be configured to identify seminars for a user of the system 10 in a variety of ways. In an exemplary embodiment, the seminar locator module 208 can be configured to receive as input a geographic location. The geographic location can be input automatically and/or manually, similar to that discussed above regarding the medical practitioner locator module 206.

Based on the patient's geographic location, the seminar locator module 208 can be configured to identify seminars to the user of the system 10 by determining which, if any, seminars stored in the seminars database 308 are within a certain geographic area. The geographic area can be defined in a variety of ways, as discussed above regarding the medical practitioner locator module 206. If the seminar locator module 208 does not identify any medical practitioners within the geographic area, the seminar locator module 208 can be configured to provide alternate seminars within an expanded geographic area near the input geographic location, e.g., expand the search area from within a ten mile radius to within a fifty mile radius. The alternate seminars can be provided by default, or the user of the system 10 can be given an option for expanding the seminars search.

In addition to or in alternative to considering the input geographic location, the seminar locator module 208 can be configured to identify seminars for the user of the system 10 based on one or more bariatric procedures the user has selected, e.g., via a patient data web interface, as being of particular interest to the user. The seminar locator module 208 can thus determine which seminars, if any, are within the geographic area and have experience in the selected bariatric procedure(s). If the seminar locator module 208 does not identify any seminars within the geographic area that have the selected procedure experience, the seminar locator module 208 can be configured to provide alternate seminars having the selected experience within an expanded geographic area near the input geographic location. The alternate seminars can be provided by default, or the user of the system 10 can be given an option for expanding the seminars search.

In addition to or in alternative to considering the input geographic location and/or bariatric procedure relevance, the seminar locator module 208 can be configured to identify seminars for the user of the system 10 based on a date of the seminar. The seminar locator module 208 can thus determine which seminars, if any, are occurring on a specific date or within a specific date range. The specific date or specific date range can be input by the user. If the seminar locator module 208 does not identify any seminars on the specific date or within the specific date range, the seminar locator module 208 can be configured to provide alternate seminars within an expanded date range, e.g., within a certain amount of days before and/or after the specific date or the specific date range. The alternate seminars can be provided by default, or the user of the system 10 can be given an option for expanding the seminars search.

Figure 39:
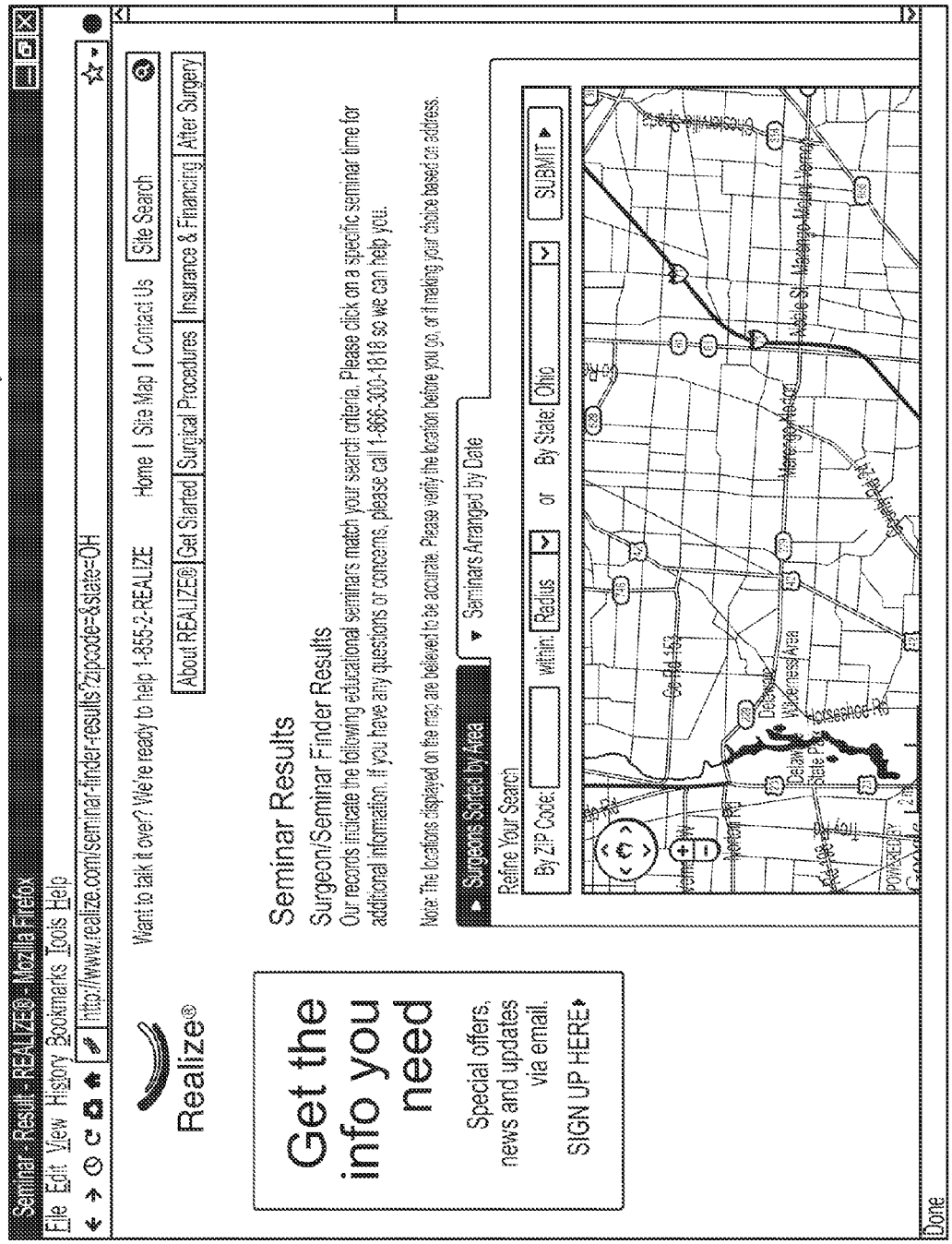
FIG. 39 is a schematic diagram of an embodiment of a seminar web interface of the metabolic and bariatric surgery outcome predictive system of FIG. 2.
Figure 40:
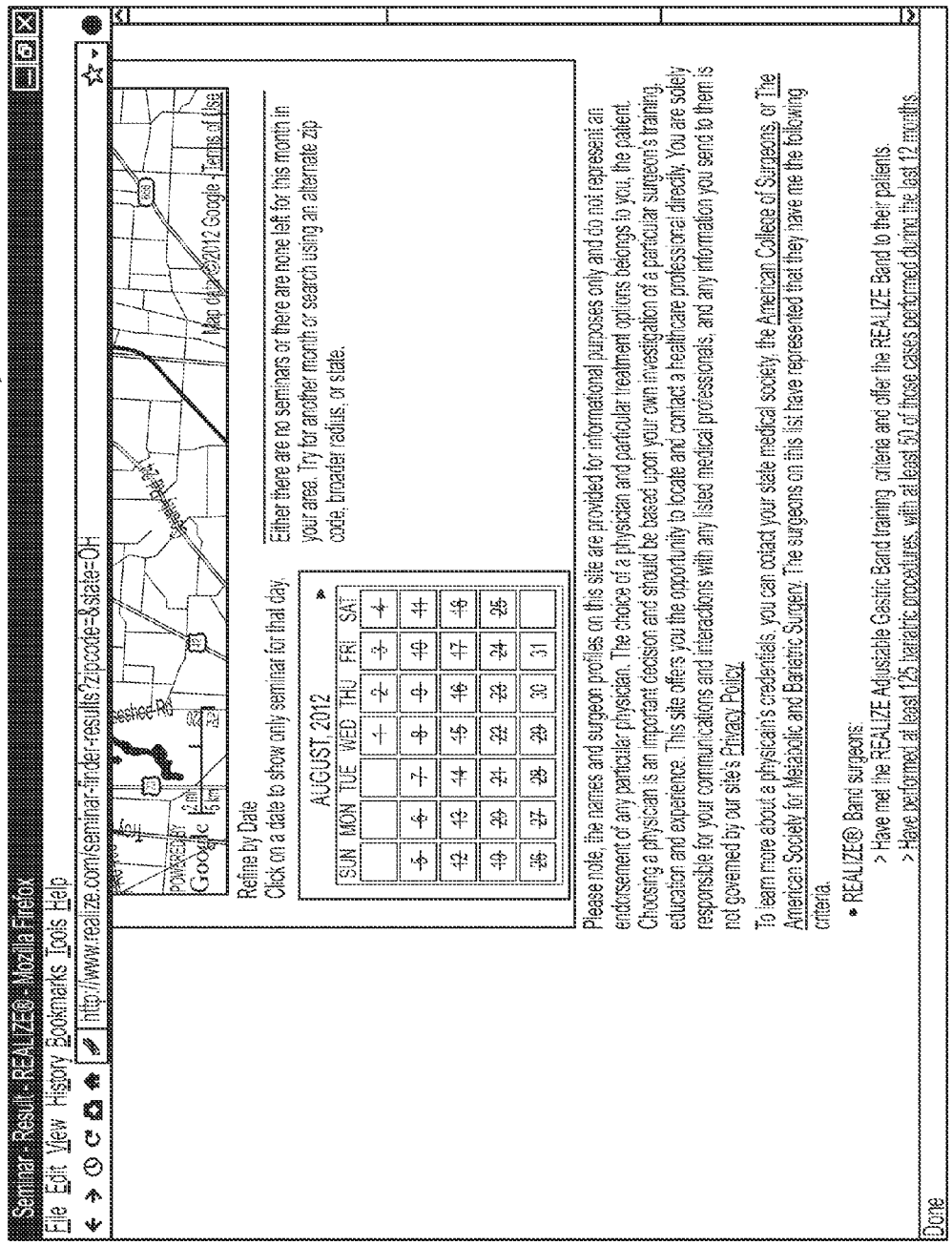
FIG. 40 is a continuation of the schematic diagram of FIG. 39.

FIGS. 39 and 40 illustrate one embodiment of a seminar web interface 3900 configured to be displayed on a client terminal and to identify seminars to a user of the system 10. FIGS. 39 and 40 display identified medical practitioners to a user as at <http://www.realize.com/> (accessed Sep. 19, 2012). FIG. 39 illustrates a top of the seminar web interface 3900, and FIG. 40 shows the seminar web interface 3900 scrolled down from FIG. 39. The seminar web interface 3900 shows seminars identified as being in the state of "Ohio" as entered in the geographic location field 706 on the patient data web interface 700 of FIG. 7. The seminar web interface 3900 shows seminars for the month the user is currently accessing the system 10, but as mentioned above, the seminar web interface 3900 can show seminars for any time period.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system, comprising:
   a non-transitory computer-readable medium having stored thereon a program that includes
      a patient data input module configured to receive data regarding a patient from a client terminal via a network, the data including two or more of a height of the patient, a weight of the patient, a gender of the patient, an age of the patient, a medical history of the patient, a medical status of the patient, a body mass index (BMI) of the patient, an ethnicity of the patient, a medical prescription history of the patient, a medical prescription status of the patient, types of medical treatments for obesity previously received by the patient, types of medical treatments for health issues other than obesity previously received by the patient, insurance information for the patient, diet information for the patient, psychological history of the patient, and a genetic indicator of the patient, and
      an outcome prediction module configured to predict an outcome of each of a plurality of different types of bariatric surgery for the patient at a specific point in time after performance of the bariatric surgery based at least on the received data regarding the patient and on historical data regarding outcomes of a plurality of bariatric surgery procedures performed on a plurality of patients, and the outcome prediction module being configured to predict a degree of confidence for each of the predicted outcomes based at least on the received data regarding the patient and on the historical data regarding outcomes of a plurality of bariatric surgery procedures performed on the plurality of patients, the degree of confidence indicating a chance that the patient will achieve the predicted outcome associated therewith at the specific point in time after performance of the bariatric surgery; and
   a processor configured to execute the program and to cause each of the predicted outcomes and each of the predicted degrees of confidence to be displayed on a display;
   wherein the outcomes of the plurality of bariatric surgery procedures performed on the plurality of patients including at least one of an amount of BMI reduction and an amount of weight loss, and
   wherein the predicted outcome of each of the plurality of bariatric surgery procedures including at least one of a predicted amount of BMI reduction and a predicted amount of weight loss.

2. The system of claim 1, wherein the different types of bariatric surgery include sleeve gastrectomy, gastric banding, and gastric bypass.

3. The system of claim 1, wherein the outcome prediction module is configured to communicate the predicted outcome of each of the plurality of bariatric surgery procedures to the client terminal via the network.

4. The system of claim 1, wherein when the outcomes of the plurality of bariatric surgery procedures performed on the plurality of patients includes at least the amount of BMI reduction, the predicted amount of BMI reduction is presented as a range of possible BMI reduction, and when the outcomes of the plurality of bariatric surgery procedures performed on the plurality of patients includes at least the amount of weight loss, the predicted amount of weight loss is presented as a range of possible amount of weight loss.

5. The system of claim 1, wherein the outcome prediction module is configured to
   compare the received data regarding the patient with corresponding data regarding the plurality of patients,
   based on the comparison, determine a subset of the plurality of patients with which the patient most closely correlates, and
   determine the predicted outcomes of each of the plurality of bariatric surgery procedures using the outcomes for the subset of the plurality of patients.

6. The system of claim 1, wherein the outcome prediction module is configured to predict the outcome using at least one of univariate analysis, multivariable regression analysis, advanced regression analysis, fully saturated regression analysis, stepwise regression analysis, and least angle regression analysis.

7. The system of claim 1, wherein the outcome prediction module is configured to cause the client terminal to graphically display the predicted outcome of each of the plurality of bariatric surgery procedures.

8. The system of claim 1, wherein the program further includes a medical practitioner locator module configured to provide a recommended medical practitioner for the patient from among a plurality of medical practitioners stored in a medical practitioner database based at least on a geographic location of the patient, the plurality of medical practitioners each being marked in the medical practitioner database as having experience with at least one of the plurality of different types of bariatric surgery.

9. The system of claim 1, wherein the program further includes a seminar locator module configured to provide a recommended seminar for the patient from among a plurality of seminars stored in a seminar database based at least on a geographic location of the patient, the plurality of seminars each being marked in the seminar database as being related to at least one of the plurality of different types of bariatric surgery.

10. The system of claim 1, wherein the outcome prediction module is configured to predict an outcome of one or more non-surgical treatments for the patient based at least on the received data regarding the patient and on historical data regarding outcomes of a plurality of non-surgical treatments received by a plurality of patients, the outcomes of the plurality of non-surgical treatments received by the plurality of patients including at least one of an amount of BMI reduction and an amount of weight loss, and the predicted outcome of each of the one or more non-surgical treatments including at least one of a predicted amount of BMI reduction and a predicted amount of weight loss.

11. The system of claim 1, wherein the outcome prediction module is configured to predict an outcome of the patient receiving no obesity treatment based at least on the received data regarding the patient and on historical data regarding outcomes of a plurality of patients who did not receive obesity treatment, the outcomes of the plurality of patients who did not receive obesity treatment received by the plurality of patients including at least one of an amount of BMI change, a change in weight, and a change in one or more comorbidities, and the predicted outcome of non-treatment for the patient including at least one of an amount of BMI change, a change in weight, and a change in the one or more comorbidities.

12. The system of claim 1, wherein the patient data input module is configured to receive user-input data selecting the specific point in time.

13. The system of claim 1, wherein the specific point in time includes a plurality of different specific points in time such that each of the predicted outcomes has a plurality of degrees of confidence associated therewith each corresponding to one of the different specific points in time.

14. A system, comprising:
a computer system configured to communicate with a client terminal via a network, the computer system comprising a processor configured to
predict an outcome of each of a plurality of different types of bariatric surgery for a patient at a specific point in time after performance of the bariatric surgery, each of the outcomes based at least on patient data and on historical data regarding outcomes of a plurality of bariatric surgery procedures performed on a plurality of patients,
the patient data including at least two or more of a height of the patient, a weight of the patient, a gender of the patient, an age of the patient, a medical history of the patient, a medical status of the patient, a body mass index (BMI) of the patient, an ethnicity of the patient, a medical prescription history of the patient, a medical prescription status of the patient, types of medical treatments for obesity previously received by the patient, types of medical treatments for health issues other than obesity previously received by the patient, insurance information for the patient, diet information for the patient, psychological history of the patient, and a genetic indicator of the patient,
the outcomes of the plurality of bariatric surgery procedures performed on the plurality of patients including at least one of an amount of BMI reduction and an amount of weight loss, and
the predicted outcome of each of the plurality of bariatric surgery procedures including at least one of a predicted amount of BMI reduction and a predicted amount of weight loss;
predict a degree of a confidence for each of the predicted outcomes indicating a chance that the patient will achieve the predicted outcome associated therewith at the specific point in time after performance of the bariatric surgery, each of the degrees of confidence based at least on the patient data and on the historical data regarding outcomes of the plurality of bariatric surgery procedures performed on the plurality of patients; and
communicate each of the predicted outcomes and each of the predicted to the client terminal via the network for display on the client terminal.

15. The system of claim 14, wherein the processor is configured to receive the patient data from the client terminal via the network.

16. The system of claim 14, wherein the processor is configured to retrieve the historical data from a historical data database.

17. The system of claim 16, wherein the processor is configured to add an actual outcome of one the plurality of different types of bariatric surgeries performed on the patient to the historical data database such that the processor is configured to predict an outcome of the one of the plurality of different types of bariatric surgery for a second patient actual based at least on the historical data including the actual outcome.

18. The system of claim 14, wherein the processor is configured to predict the outcome using at least one of univariate analysis, multivariable regression analysis, advanced regression analysis, fully saturated regression analysis, stepwise regression analysis, and least angle regression analysis.

19. A system, comprising:
a non-transitory computer-readable medium having stored thereon a program that includes
a patient data input module configured to receive data regarding a patient from a client terminal via a network, the data including two or more of a height of the patient, a weight of the patient, a gender of the patient, an age of the patient, a medical history of the patient, a medical status of the patient, a body mass index (BMI) of the patient, an ethnicity of the patient, a medical prescription history of the patient, a medical prescription status of the patient, types of medical treatments for obesity previously received by the patient, types of medical treatments for health issues other than obesity previously received by the patient, insurance information for the patient, diet information for the patient, psychological history of the patient, and a genetic indicator of the patient, and
an outcome prediction module configured to predict an outcome of each of a plurality of different types of bariatric surgery for the patient at a specific point in time after performance of the bariatric surgery based at least on the received data regarding the patient and on historical data regarding outcomes of a plurality of bariatric surgery procedures performed on a plurality of patients, and the outcome prediction module being configured to predict a degree of confidence for each of the predicted outcomes based at least on the received data regarding the patient and on the historical data regarding outcomes of a plurality of bariatric surgery procedures performed on the plurality of patients, the degree of confidence indicating a chance that the patient will achieve the predicted outcome associated therewith at the specific point in time after performance of the bariatric surgery; and a processor configured to execute the program and to cause each of the predicted outcomes and each of the predicted degrees of confidence to be displayed on a display;

wherein the outcomes of the plurality of bariatric surgery procedures performed on the plurality of patients including a change in at least one comorbidity, and wherein the predicted outcome of each of the plurality of bariatric surgery procedures including change in the at least one comorbidity.

20. The system of claim 19, wherein the different types of bariatric surgery include sleeve gastrectomy, gastric banding, and gastric bypass.

21. The system of claim 19, wherein the outcome prediction module is configured to predict the outcome using at least one of univariate analysis, multivariable regression analysis, advanced regression analysis, fully saturated regression analysis, stepwise regression analysis, and least angle regression analysis.

* * * * *